US008492562B2

(12) United States Patent
Sato et al.

(10) Patent No.: US 8,492,562 B2
(45) Date of Patent: Jul. 23, 2013

(54) (METH)ACRYLATE DERIVATIVE, INTERMEDIATE THEREOF, AND POLYMER COMPOUND

(75) Inventors: Junko Sato, Tainai (JP); Osamu Nakayama, Tainai (JP); Takashi Fukumoto, Tainai (JP)

(73) Assignee: Kuraray Co., Ltd., Kurashiki-shi (JP)

( * ) Notice: Subject to any disclaimer, the term of this patent is extended or adjusted under 35 U.S.C. 154(b) by 129 days.

(21) Appl. No.: 12/918,675

(22) PCT Filed: Feb. 20, 2009

(86) PCT No.: PCT/JP2009/052994

§ 371 (c)(1),
(2), (4) Date: Aug. 23, 2010

(87) PCT Pub. No.: WO2009/104726

PCT Pub. Date: Aug. 27, 2009

(65) Prior Publication Data

US 2010/0331508 A1 Dec. 30, 2010

(30) Foreign Application Priority Data

Feb. 22, 2008 (JP) ................................ 2008-041008

(51) Int. Cl.

| | |
|---|---|
| ***C07D 327/06*** | (2006.01) |
| ***C07D 497/00*** | (2006.01) |
| ***C07D 327/02*** | (2006.01) |
| ***C07D 339/08*** | (2006.01) |
| ***C07D 339/00*** | (2006.01) |
| ***C07D 321/02*** | (2006.01) |
| ***C07D 321/12*** | (2006.01) |
| ***C07D 319/06*** | (2006.01) |

(52) U.S. Cl.
USPC .................. 549/10; 549/11; 549/14; 549/21; 549/347; 549/378

(58) Field of Classification Search
USPC .......................... 549/10, 11, 14, 21, 347, 378
See application file for complete search history.

(56) References Cited

U.S. PATENT DOCUMENTS

| | | | | |
|---|---|---|---|---|
| 2005/0266351 | A1 * | 12/2005 | Takemoto et al. | 430/311 |
| 2007/0269741 | A1 | 11/2007 | Iijima et al. | |
| 2010/0035180 | A1 * | 2/2010 | Shimada et al. | 430/270.1 |
| 2011/0053082 | A1 * | 3/2011 | Ichikawa et al. | 430/270.1 |

FOREIGN PATENT DOCUMENTS

| | | | |
|---|---|---|---|
| EP | 1 992 651 | A1 | 11/2008 |
| JP | 2-59570 | A | 2/1990 |
| JP | 5-88367 | A | 4/1993 |
| JP | 7-295221 | A | 11/1995 |
| JP | 07295221 | A * | 11/1995 |
| JP | 9-73173 | A | 3/1997 |
| JP | 2003-246825 | A | 9/2003 |
| JP | 2004-46206 | A | 2/2004 |
| JP | 2007-308586 | A | 11/2007 |
| JP | 2008-138073 | A | 6/2008 |
| JP | 2011141527 | A * | 7/2011 |
| WO | WO 2007/094474 | A1 | 8/2007 |

OTHER PUBLICATIONS

English Translation of JP 07-295221 A; Horibe et al; Apr. 1994.*
U.S. Appl. No. 12/918,689, filed Aug. 20, 2010, Nakayama, et al.
U.S. Appl. No. 12/918,527, filed Aug. 23, 2010, Nakayama, et al.
International Search Report issued May 26, 2009 in PCT/JP2009/052994.
Satoshi Takechi et al., "Impact of 2-Methyl-2-Adamantyl Group Used for 193-nm Single-Layer Resist", Journal of Photopolymer Science and Technology, vol. 9, No. 3, 1996, pp. 475-487.
U.S. Appl. No. 13/617,023, filed Sep. 14, 2012, Nakayama, et al.

* cited by examiner

*Primary Examiner* — Karuna P Reddy
(74) *Attorney, Agent, or Firm* — Oblon, Spivak, McClelland, Maier & Neustadt, L.L.P.

(57) ABSTRACT

Provided are a polymerizable compound shown below which is useful as a raw material for a polymer having less swelling in developing, a polymer obtained by polymerizing a raw material containing the above polymerizable compound, a photoresist composition which contains the above polymer and which is improved in LWR and an efficient production process for the polymerizable compound described above:

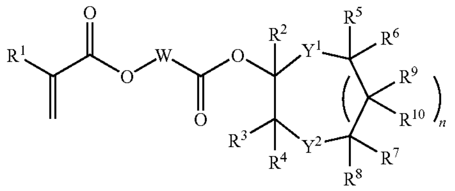

wherein n represents an integer of 0 to 2; $R^1$ represents a hydrogen atom, methyl or trifluoromethyl; $R^2$, $R^3$, $R^4$, $R^5$, $R^6$, $R^7$, $R^8$, $R^9$ and $R^{10}$ represent a hydrogen atom, an alkyl group having 1 to 6 carbon atoms or the like; W represents an alkylene group having 1 to 10 carbon atoms or the like; and $Y^1$ and $Y^2$ represent an oxygen atom or a sulfur atom.

8 Claims, No Drawings

(METH)ACRYLATE DERIVATIVE, INTERMEDIATE THEREOF, AND POLYMER COMPOUND

TECHNICAL FIELD

The present invention relates to (meth)acrylic ester derivatives, intermediates thereof (haloester derivatives), a production process for them, polymers obtained by polymerizing raw materials containing the above (meth)acrylic ester derivatives and photoresist compositions containing the above polymers.

BACKGROUND ART

In recent years, electronic devices are highly required to be increased in integration in the electronic device production field represented by integrated circuit device production, and this allows a photolithographic technique for forming fine patterns to be required.

In general, a wavelength of an exposure light source is shortened as means for obtaining fine patterns. To be specific, a UV ray represented by a g beam and an i beam has so far been used therefor, but at present, semiconductor devices in which a KrF excimer laser and an ArF excimer laser are used are initiated to be produced in an industrial scale. Further, a $F_2$ excimer laser, an electron beam, EUV (an extreme UV ray) and an X ray which have shorter wavelengths than those of the above excimer lasers are investigated.

Lithographic characteristics such as a sensitivity to the above light sources and a resolution in which patterns having a fine dimension can be reproduced are required to resist materials.

Chemically amplified photoresist compositions comprising polymers having an acid-dissociable functional group and compounds (herein referred to as "a photoacid generator") generating acid by irradiation (herein referred to as "exposure") of a radial ray are used as resist materials satisfying the above requirement.

The above polymer having an acid-dissociable functional group comprises a basic structure in which a part of an alkali-readily soluble site of an alkali-soluble polymer is protected by a suitable acid-dissociable functional group, and selection of the above acid-dissociable functional group is very important in terms of controlling the performances of the photoresist composition.

Known as the existing acid-dissociable functional group are groups having an adamantane structure (refer to a patent document 1 and a non-patent document 1), groups comprising a tetrahydropyranyl group (refer to a patent document 2) and groups comprising a lactone ring (refer to a patent document 3).

Patent document 1: Japanese Patent Application Laid-Open No. 73173/1997

Patent document 2: Japanese Patent Application Laid-Open No. 88367/1993

Patent document 3: Japanese Patent Application Laid-Open No. 46206/2004

Non-patent document 1: Journal of Photopolymer Science and Technology, Vol. 9, No. 3, p. 475 to 487 (1996)

DISCLOSURE OF THE INVENTION

Problems to be Solved by the Invention

Pattern rules are required to be further finer, and on the other hand, satisfactory performances have not yet been obtained in conventional photoresist compositions prepared by using compounds disclosed in the patent documents 1 to 3 and the non-patent document 1.

The largest problem is line width variation of formed patterns which is called a line width roughness (LWR), and an allowable value thereof is required to be less than 8% of a line width (refer to ITRS 2006 edition, the part of lithography, p. 7). It is necessary for improving LWR to inhibit patterns from being deformed by swelling. A polymer which is a component of a resist composition has to be less liable to be swollen in order to inhibit patterns from being deformed by swelling. However, resist compositions having performances of a satisfactory level are not necessarily obtained from polymers prepared according to combination of conventionally known polymerizable compounds.

An object of the present invention is to provide a polymerizable compound shown below which is useful as a raw material for a polymer having less swelling in developing, a polymer obtained by polymerizing a raw material containing the above polymerizable compound, a photoresist composition which contains the above polymer and which is improved in LWR and an efficient production process for the polymerizable compound described above.

Means for Solving the Problems

Intense investigations carried out by the present inventors in order to solve the problems described in RELATED ART have resulted in finding that a specific acid-dissociable functional group is excellent in a reactivity to acids and that a polymer obtained by polymerizing a raw material containing a compound in which an acid-dissociable functional group is introduced into a position apart from a polymerizable functional group is useful as a component for a photoresist composition which has a high dissolution rate to a developer after exposure and which inhibits swelling in developing to make it possible to form patterns having an excellent resolution.

That is, the present invention is achieved by providing:

[1] a production process for a (meth)acrylic ester derivative (hereinafter referred to as a (meth)acrylic ester derivative (1)) represented by Formula (1) shown below:

(1)

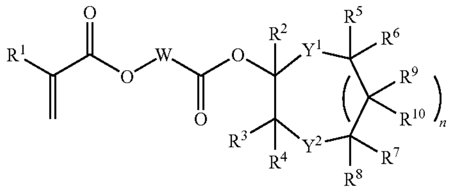

(wherein n, $R^1$, $R^2$, $R^3$, $R^4$, $R^5$, $R^6$, $R^7$, $R^8$, $R^9$, $R^{10}$, W, $Y^1$ and $Y^2$ are the same as defined below), comprising the steps of: reacting alcohol (hereinafter referred to as alcohol (2)) represented by Formula (2) shown below:

(2)

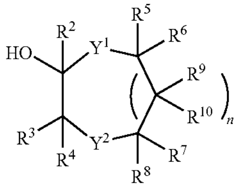

(wherein combination of $R^2$, $R^3$ and $R^4$ is any of:

1) $R^2$, $R^3$ and $R^4$ each represent independently a hydrogen atom, a linear alkyl group having 1 to 6 carbon atoms, a branched alkyl group having 3 to 6 carbon atoms or a cyclic alkyl group having 3 to 6 carbon atoms;

2) $R^2$ and $R^3$ are combined to represent an alkylene group having 3 to 6 carbon atoms, and $R^4$ represents a hydrogen atom, a linear alkyl group having 1 to 6 carbon atoms, a branched alkyl group having 3 to 6 carbon atoms or a cyclic alkyl group having 3 to 6 carbon atoms; or 3) $R^2$ represents a hydrogen atom, a linear alkyl group having 1 to 6 carbon atoms, a branched alkyl group having 3 to 6 carbon atoms or a cyclic alkyl group having 3 to 6 carbon atoms, and $R^3$ and $R^4$ are combined to represent an alkylene group having 3 to 6 carbon atoms;

in n, $R^5$, $R^6$, $R^7$, $R^8$, $R^9$ and $R^{10}$, 1) when n is 0, $R^5$ and $R^8$ each represent independently a hydrogen atom, a linear alkyl group having 1 to 6 carbon atoms, a branched alkyl group having 3 to 6 carbon atoms or a cyclic alkyl group having 3 to 6 carbon atoms; $R^6$ and $R^7$ each represent independently a hydrogen atom, a linear alkyl group having 1 to 6 carbon atoms, a branched alkyl group having 3 to 6 carbon atoms or a cyclic alkyl group having 3 to 6 carbon atoms or $R^6$ and $R^7$ are combined to represent an alkylene group having 3 to 6 carbon atoms; or 2) when n is 1 or 2, $R^5$, $R^6$, $R^7$, $R^8$, $R^9$ and $R^{10}$ each represent independently a hydrogen atom, a linear alkyl group having 1 to 6 carbon atoms, a branched alkyl group having 3 to 6 carbon atoms or a cyclic alkyl group having 3 to 6 carbon atoms; $Y^1$ and $Y^2$ each represent independently an oxygen atom or a sulfur atom) with halocarboxylic halide (hereinafter referred to as halocarboxylic halide (3)) represented by Formula (3) shown below:

(3)

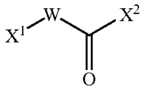

(wherein W represents a linear alkylene group having 1 to 10 carbon atoms, a branched alkylene group having 3 to 10 carbon atoms or a cyclic alkylene group having 3 to 10 carbon atoms; and $X^1$ and $X^2$ each represent independently a chlorine atom, a bromine atom or an iodine atom) in the presence of a basic substance to thereby obtain a haloester derivative (hereinafter referred to as a haloester derivative (4)) represented by Formula (4) shown below:

(4)

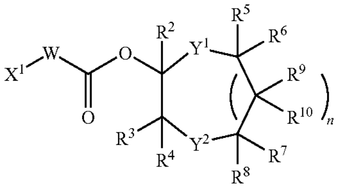

(wherein n, $R^2$, $R^3$, $R^4$, $R^5$, $R^6$, $R^7$, $R^8$, $R^9$, $R^{10}$, W, $X^1$, $Y^1$ and $Y^2$ are the same as defined above) and reacting the above haloester derivative obtained with (meth) acrylic acid (hereinafter referred to as (meth)acrylic acid (5)) represented by Formula (5) shown below:

(5)

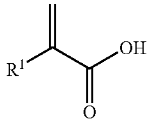

(wherein $R^1$ represents a hydrogen atom, methyl or trifluoromethyl) in the presence of a basic substance,

[2] a production process for the (meth)acrylic ester derivative (1), comprising the step of reacting the haloester derivative (4) with the (meth)acrylic acid (5) in the presence of a basic substance,

[3] a production process for the haloester derivative (4)), comprising the step of reacting the alcohol (2) with the halocarboxylic halide (3) in the presence of a basic substance,

[4] the (meth)acrylic ester derivative (1),

[5] the haloester derivative (4),

[6] the (meth)acrylic ester derivative (1) according to the above item [4], wherein W is methylene or ethane-1,1-diyl; n is 0 or 1; and $R^2$, $R^3$, $R^4$, $R^5$, $R^6$, $R^7$, $R^8$, $R^9$ and $R^{10}$ are a hydrogen atom or methyl,

[7] the haloester derivative (4) according to the above item [5], wherein $X^1$ is a chlorine atom; W is methylene or ethane-1,1-diyl; n is 0 or 1; and $R^2$, $R^3$, $R^4$, $R^5$, $R^6$, $R^7$, $R^8$, $R^9$ and $R^{10}$ are a hydrogen atom or methyl,

[8] a polymer obtained by polymerizing a raw material containing the (meth)acrylic ester derivative according to the above item [4] or [6] and

[9] a photoresist composition containing the polymer according to the above item [8].

Effect Of The Invention

According to the present invention, capable of being provided is a polymer which is excellent in a reactivity to acids and which has a high dissolution rate to a developer after exposure and is reduced in swelling in developing, and capable of being further provided are a polymerizable compound which is useful as a raw material for the above polymer, a polymer obtained by polymerizing a raw material containing the above polymerizable compound, an efficient production process for the polymerizable compound described above and a photoresist composition which contains the above polymer and which is improved in LWR.

BEST MODE FOR CARRYING OUT THE INVENTION

(Meth)Acrylic Ester Derivative (1)

$R^1$ in the (meth)acrylic ester derivative (1) represents a hydrogen atom, methyl or trifluoromethyl. $R^1$ is preferably a hydrogen atom or methyl.

Combination of $R^2$, $R^3$ and $R^4$ in the (meth)acrylic ester derivative (1) is any of 1), 2) and 3) shown below:

1) $R^2$, $R^3$ and $R^4$ each represent independently a hydrogen atom, a linear alkyl group having 1 to 6 carbon atoms, a branched alkyl group having 3 to 6 carbon atoms or a cyclic alkyl group having 3 to 6 carbon atoms;

2) $R^2$ and $R^3$ are combined to represent an alkylene group having 3 to 6 carbon atoms, and $R^4$ represents a hydrogen atom, a linear alkyl group having 1 to 6 carbon atoms, a branched alkyl group having 3 to 6 carbon atoms or a cyclic alkyl group having 3 to 6 carbon atoms; and 3) $R^2$ represents a hydrogen atom, a linear alkyl group having 1 to 6 carbon atoms, a branched alkyl group having 3 to 6 carbon atoms or a cyclic alkyl group having 3 to 6 carbon atoms, and $R^3$ and $R^4$ are combined to represent an alkylene group having 3 to 6 carbon atoms.

The above linear alkyl groups having 1 to 6 carbon atoms include, for example, methyl, ethyl, n-propyl, n-butyl, n-pentyl, n-hexyl and the like in all cases. The above branched alkyl groups having 3 to 6 carbon atoms include, for example, isopropyl, isobutyl, sec-butyl and the like in all cases. The above cyclic alkyl groups having 3 to 6 carbon atoms include, for example, cyclopropyl, cyclobutyl, cyclopentyl, cyclohexyl and the like in all cases.

The above alkylene group having 3 to 6 carbon atoms in a case where $R^2$ and $R^3$ are combined includes, for example, propane-1,3-diyl, butane-1,4-diyl, pentane-1,5-diyl, hexane-1,6-diyl and the like. Among them, butane-1,4-diyl is preferred.

The above alkylene group having 3 to 6 carbon atoms in a case where $R^3$ and $R^4$ are combined includes, for example, propane-1,3-diyl, butane-1,4-diyl, pentane-1,5-diyl, hexane-1,6-diyl and the like.

The combination of $R^2$, $R^3$ and $R^4$ is preferably the case of 1) described above, and $R^2$, $R^3$ and $R^4$ each are more preferably a hydrogen atom or methyl.

In the (meth) acrylic ester derivative (1), n, $R^5$, $R^6$, $R^7$, $R^8$, $R^9$ and $R^{10}$ are any of 1) and 2) shown below.

1) When n is 0, $R^5$ and $R^8$ each represent independently a hydrogen atom, a linear alkyl group having 1 to 6 carbon atoms, a branched alkyl group having 3 to 6 carbon atoms or a cyclic alkyl group having 3 to 6 carbon atoms; $R^6$ and $R^7$ each represent independently a hydrogen atom, a linear alkyl group having 1 to 6 carbon atoms, a branched alkyl group having 3 to 6 carbon atoms or a cyclic alkyl group having 3 to 6 carbon atoms or $R^6$ and $R^7$ are combined to represent an alkylene group having 3 to 6 carbon atoms.

2) When n is 1 or 2, $R^5$, $R^6$, $R^7$, $R^8$, $R^9$ and $R^{10}$ each represent independently a hydrogen atom, a linear alkyl group having 1 to 6 carbon atoms, a branched alkyl group having 3 to 6 carbon atoms or a cyclic alkyl group having 3 to 6 carbon atoms.

The above linear alkyl groups having 1 to 6 carbon atoms include, for example, methyl, ethyl, n-propyl, n-butyl, n-pentyl, n-hexyl and the like in all cases. The above branched alkyl groups having 3 to 6 carbon atoms include, for example, isopropyl, isobutyl, sec-butyl and the like in all cases. The above cyclic alkyl groups having 3 to 6 carbon atoms include, for example, cyclopropyl, cyclobutyl, cyclopentyl, cyclohexyl and the like in all cases.

The alkylene group having 3 to 6 carbon atoms in a case where $R^6$ and $R^7$ are combined includes, for example, propane-1,3-diyl, butane-1,4-diyl, pentane-1,5-diyl, hexane-1,6-diyl and the like. Among them, butane-1,4-diyl is preferred.

The term n is preferably 0 or 1, more preferably 0.

When n is 0, $R^5$, $R^6$, $R^7$ and $R^8$ each are preferably a hydrogen atom or methyl.

When n is 1, $R^5$, $R^6$, $R^7$, $R^8$, $R^9$ and $R^{10}$ each are preferably a hydrogen atom or methyl, and all of $R^5$, $R^6$, $R^7$, $R^8$, $R^9$ and $R^{10}$ are more preferably a hydrogen atom.

In the (meth)acrylic ester derivative (1), $Y^1$ and $Y^2$ each represent independently an oxygen atom or a sulfur atom.

W represents a linear alkylene group having 1 to 10 carbon atoms, a branched alkylene group having 3 to 10 carbon atoms or a cyclic alkylene group having 3 to 10 carbon atoms. The linear alkylene group having 1 to 10 carbon atoms includes, for example, methylene, ethane-1,2-diyl, propane-1,3-diyl, pentane-1,5-diyl, hexane-1,6-diyl and the like. The branched alkylene group having 3 to 10 carbon atoms includes, for example, ethane-1,1-diyl, propane-1,1-diyl, propane-1,2-diyl and the like. The cyclic alkylene group having 3 to 10 carbon atoms includes, for example, cyclohexane-1,4-diyl and the like. W is preferably a linear alkylene group having 1 to 10 carbon atoms or a branched alkylene group having 3 to 10 carbon atoms, more preferably methylene or ethane-1,1-diyl.

The specific examples of the (meth)acrylic ester derivative (1) include the following compounds, but they shall not specifically be restricted to these compounds.

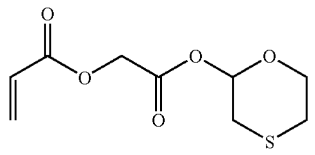

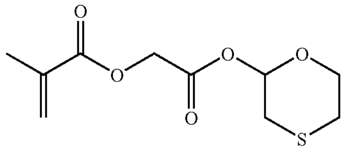

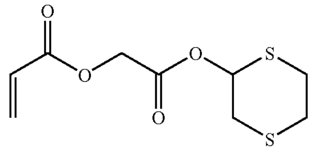

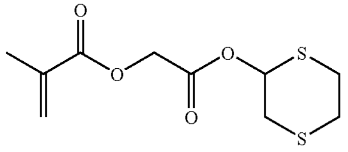

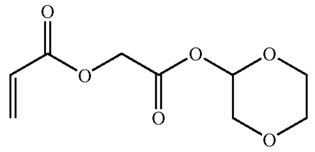

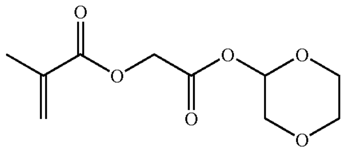

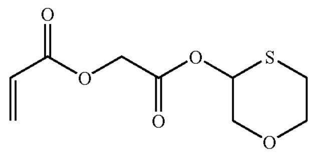

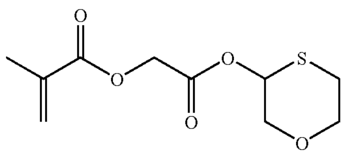

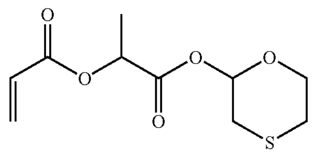

-continued
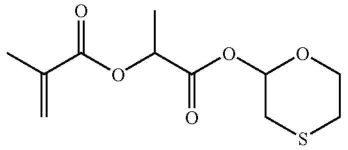
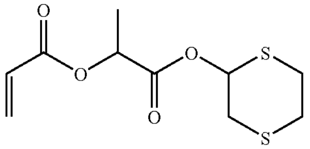
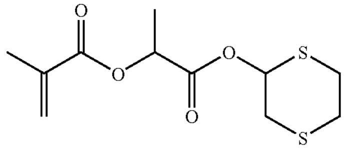
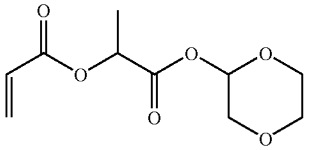
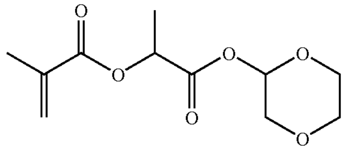
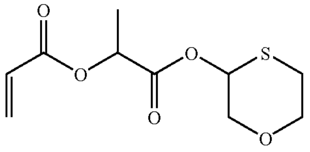
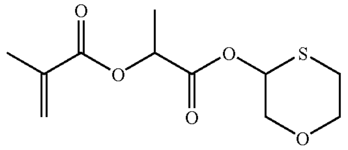
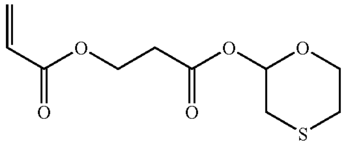
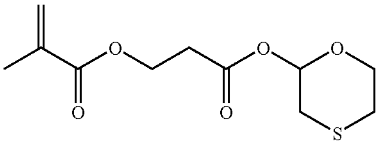
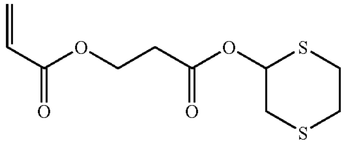
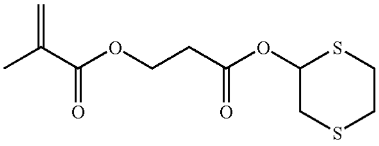
-continued
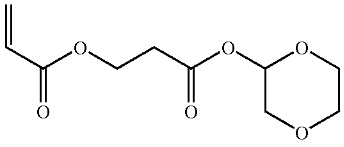
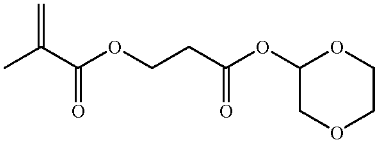
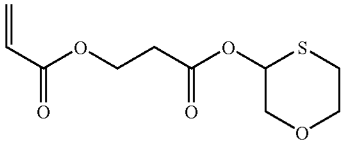
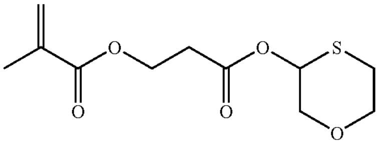
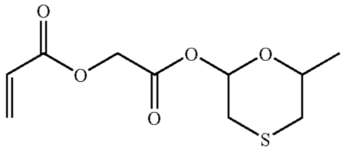
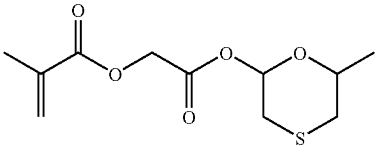
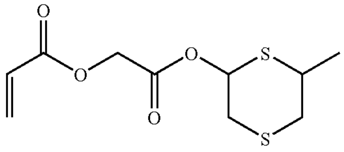
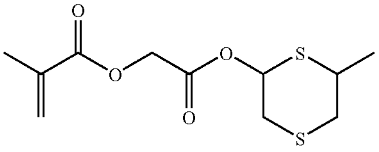
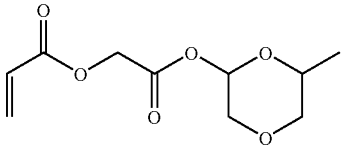
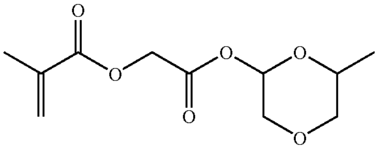
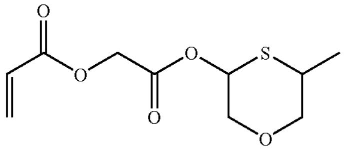

-continued
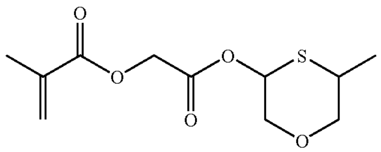
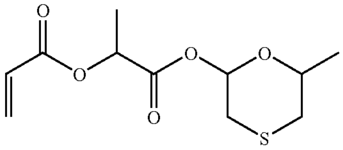
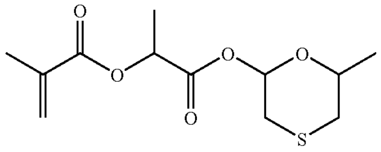
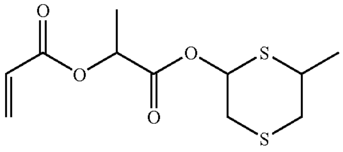
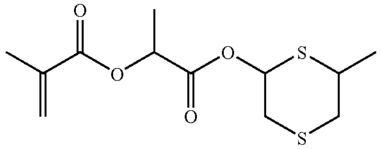
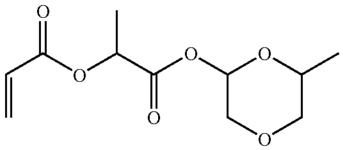
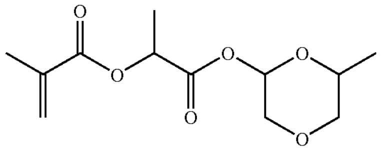
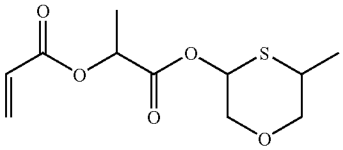
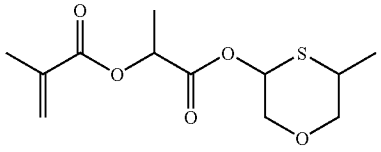
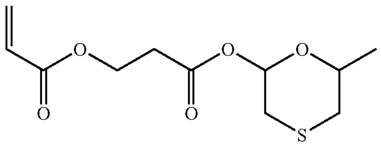
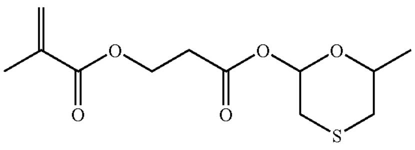
-continued
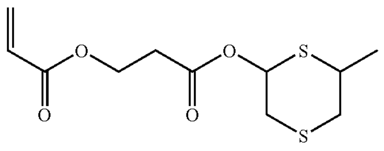
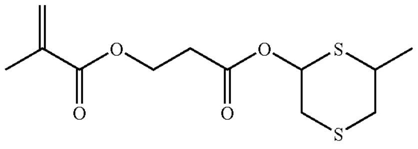
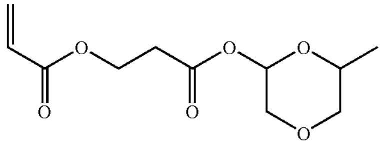
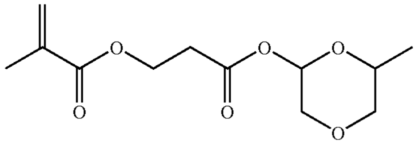
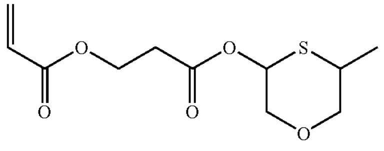
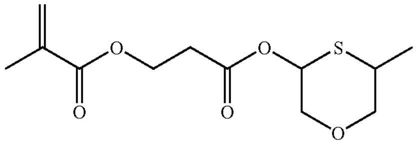
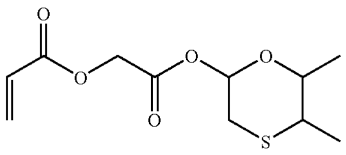
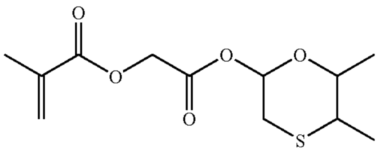
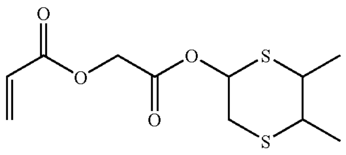
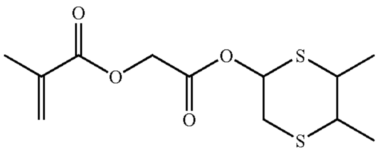
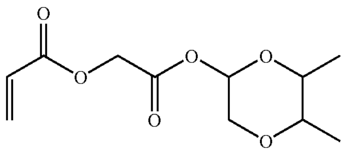

-continued
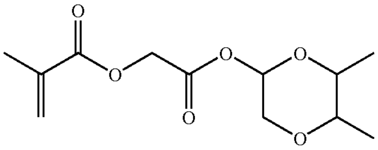
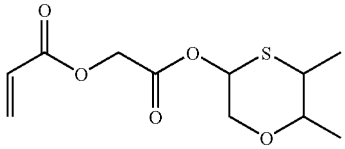
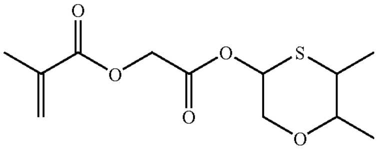
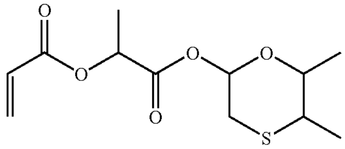
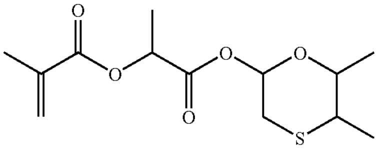
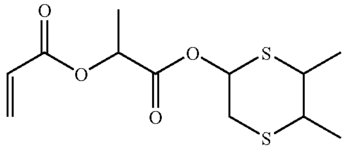
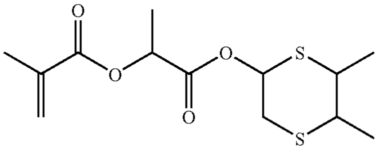
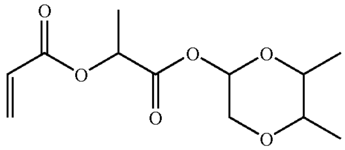
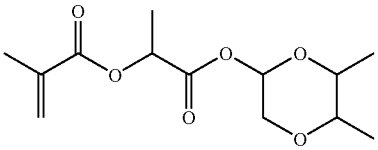
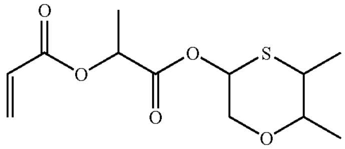
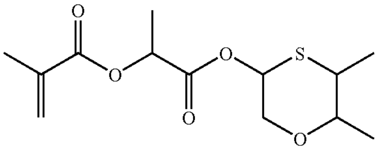
-continued
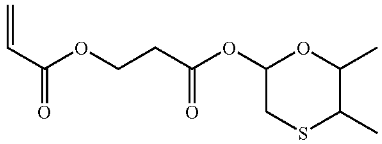
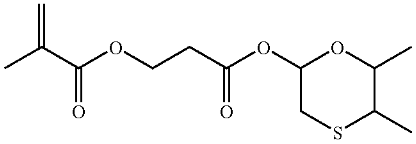
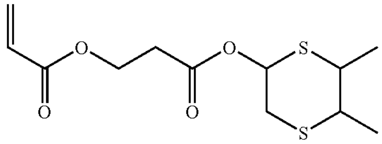
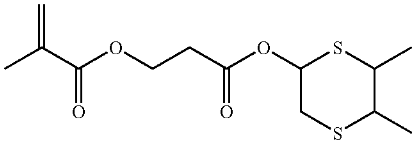
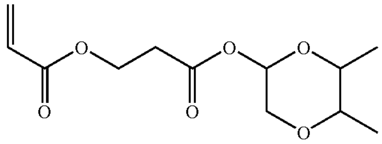
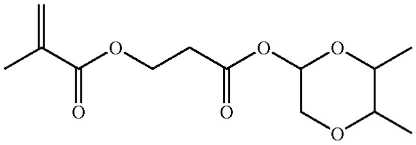
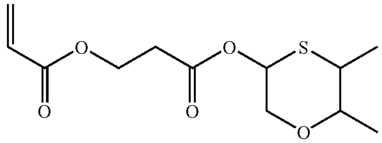
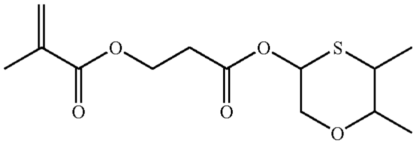
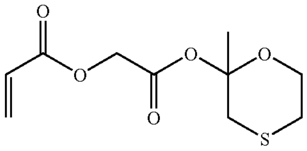
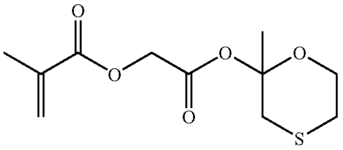
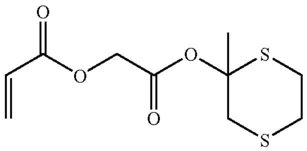

-continued
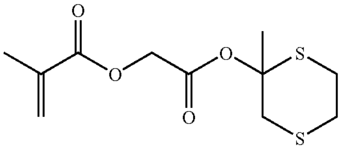
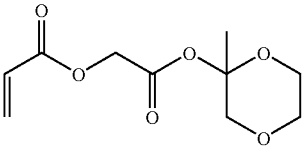
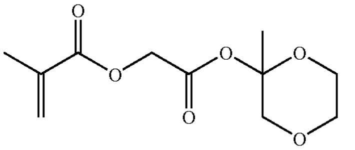
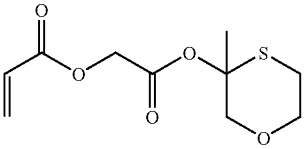
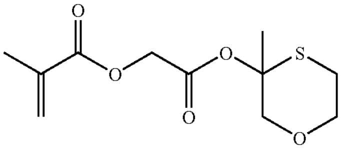
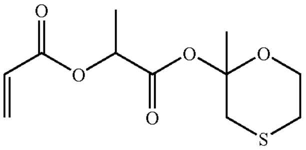
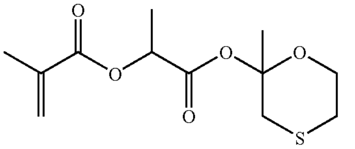
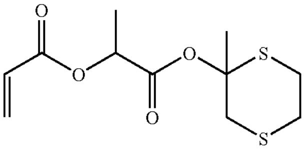
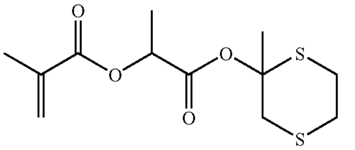
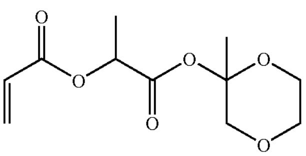
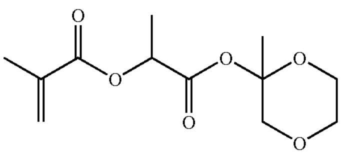
-continued
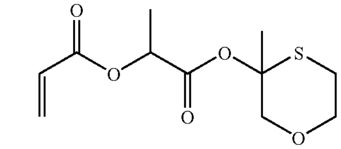
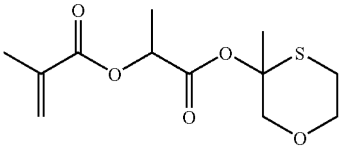
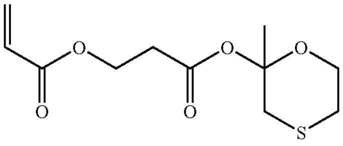
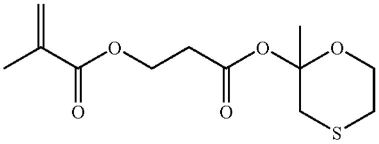
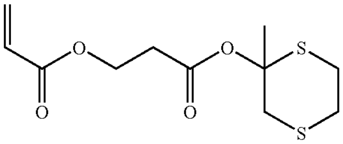
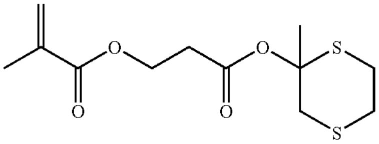
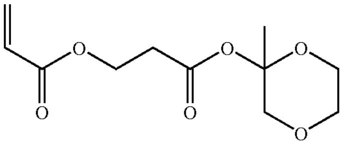
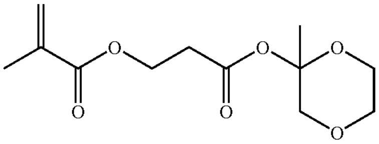
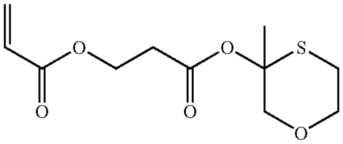
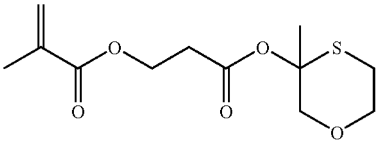
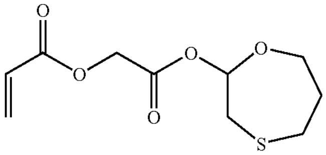

-continued
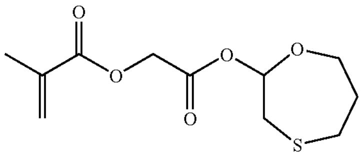
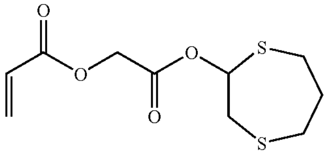
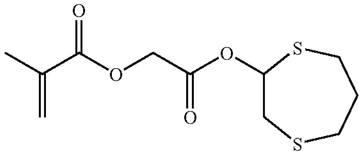
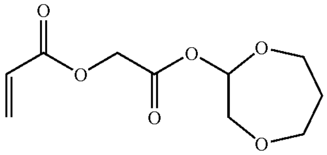
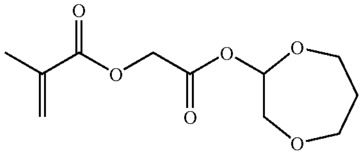
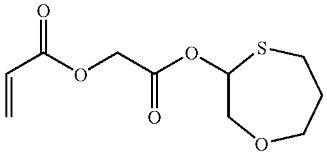
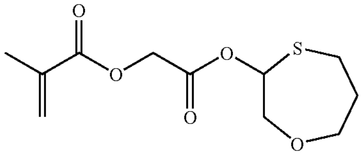
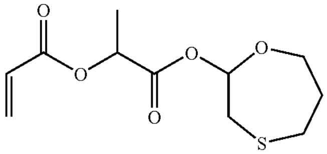
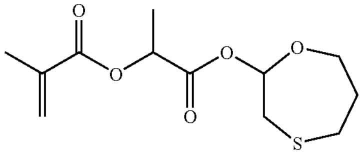
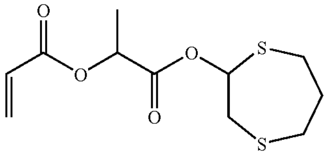
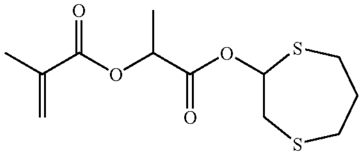
-continued
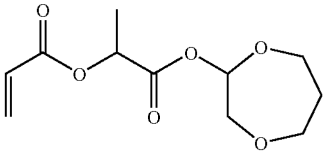
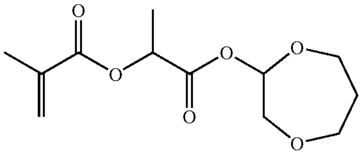
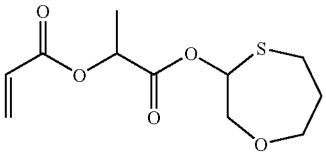
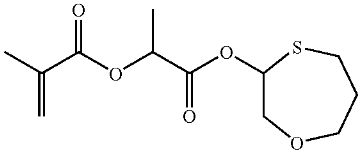
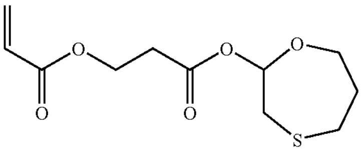
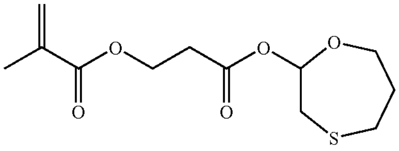
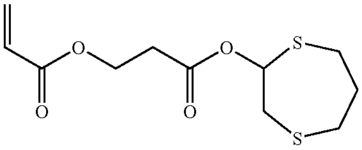
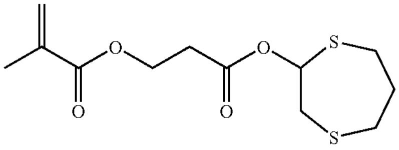
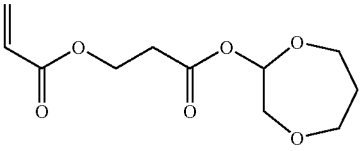
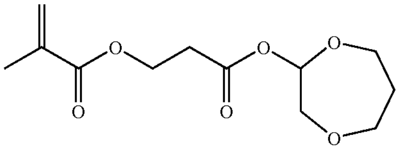
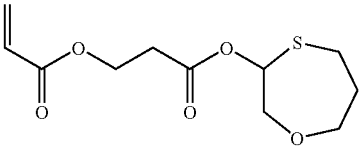

-continued
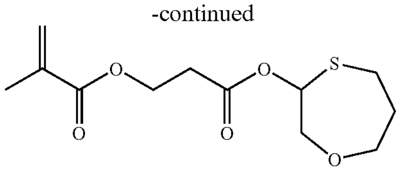
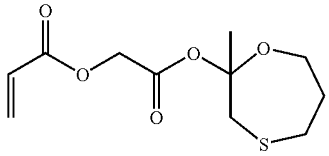
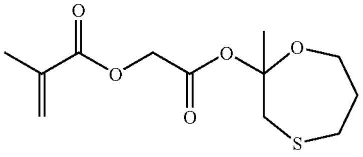
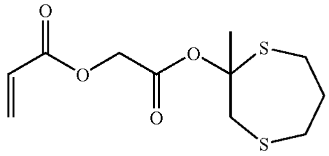
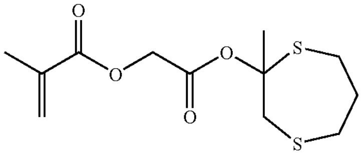
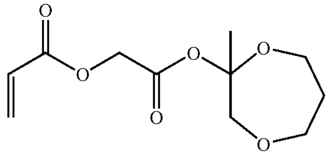
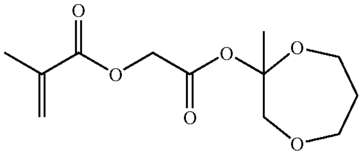
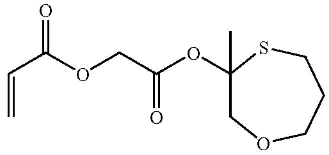
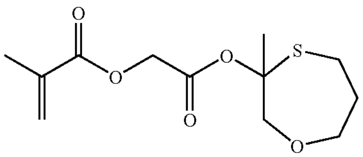
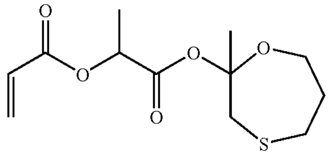
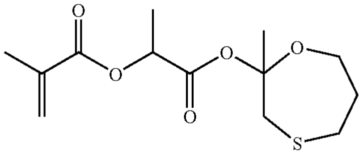
-continued
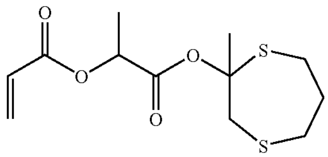
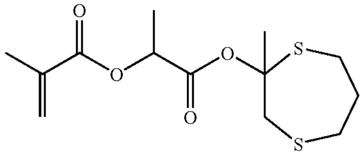
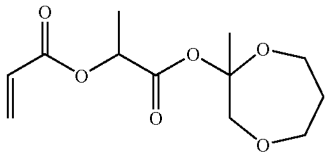
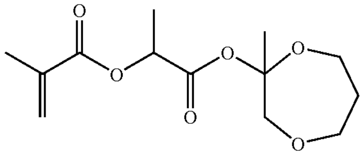
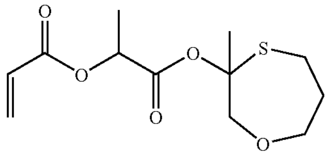
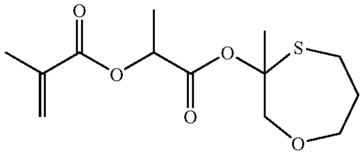
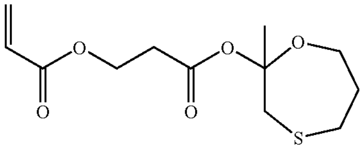
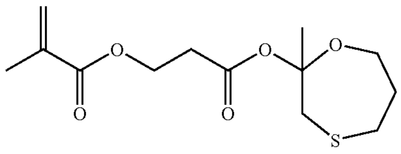
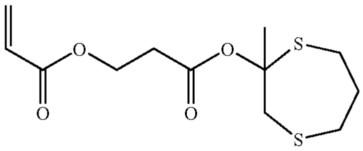
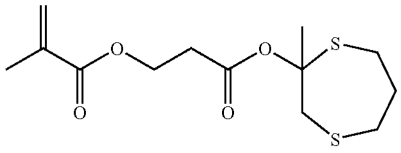
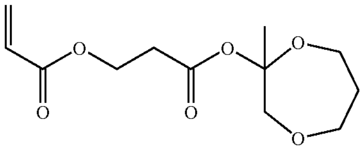

-continued
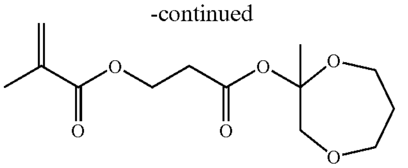
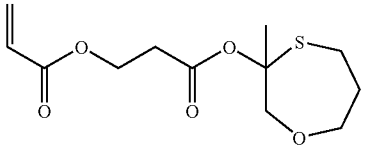
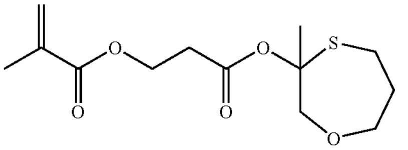
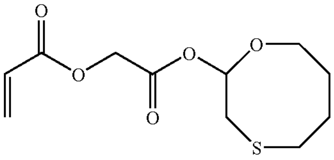
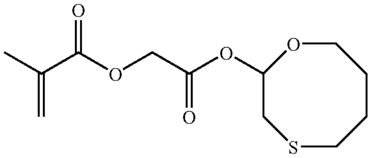
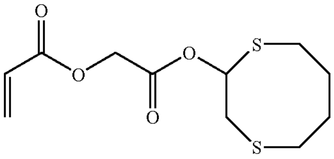
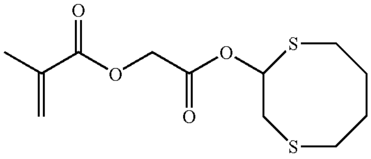
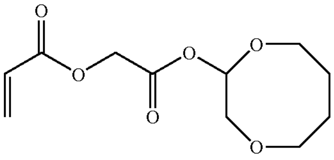
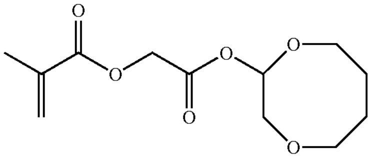
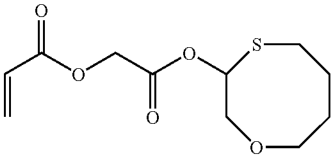
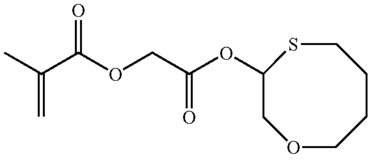
-continued
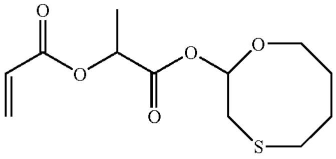
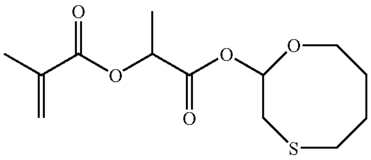
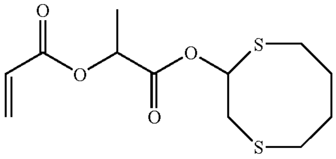
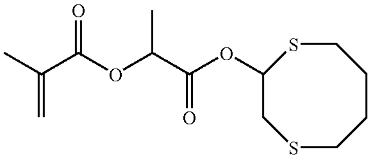
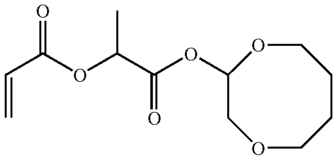
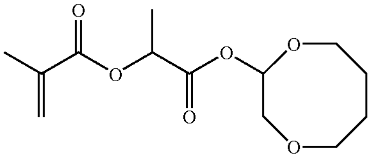
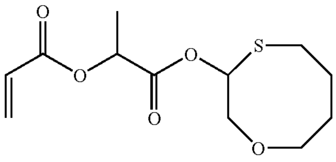
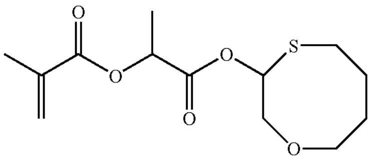
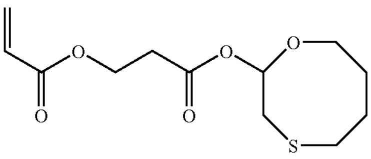
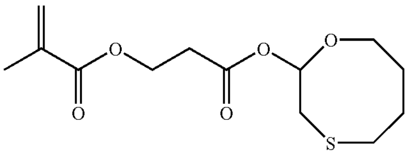

-continued
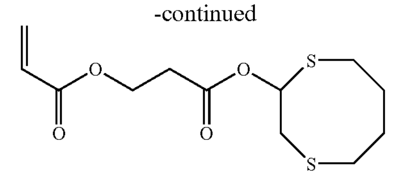
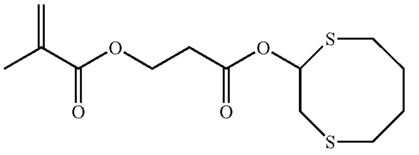
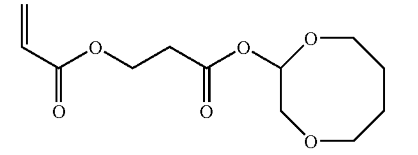
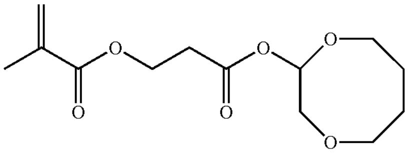
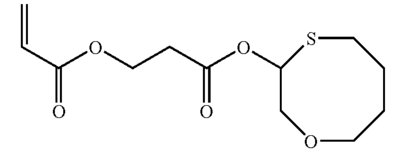
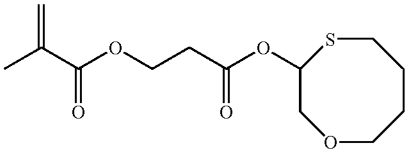
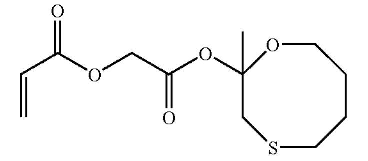
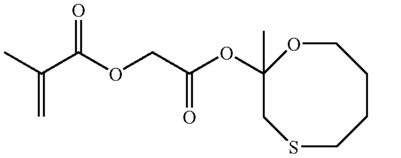
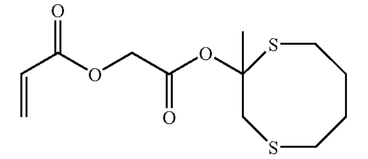
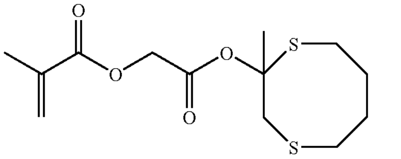
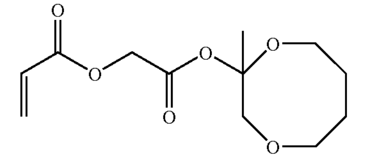
-continued
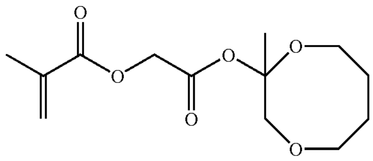
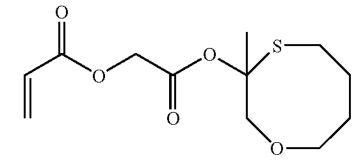
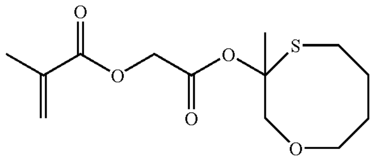
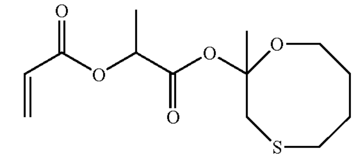
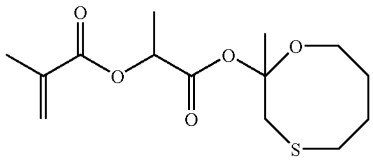
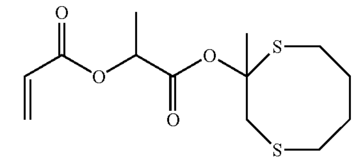
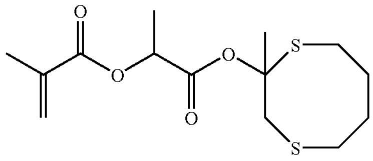
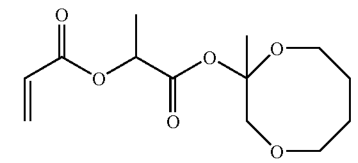
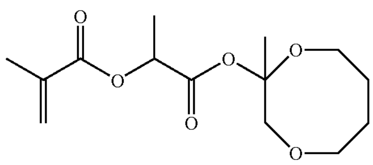
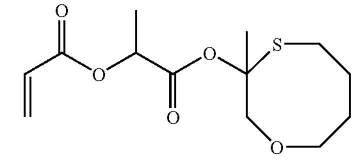

-continued

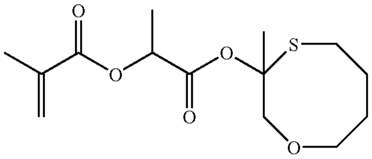

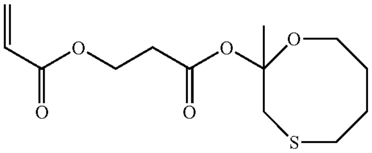

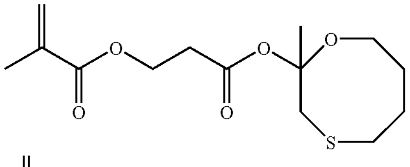

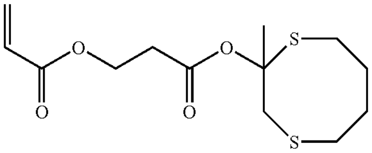

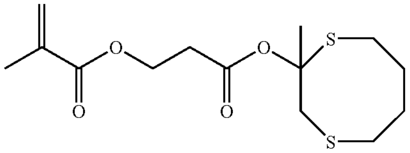

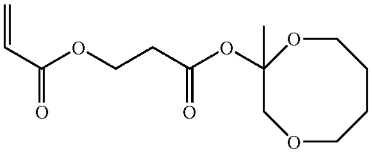

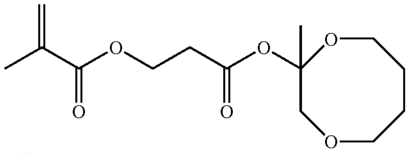

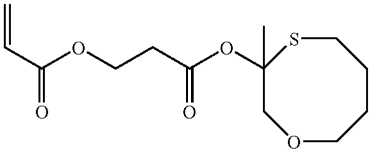

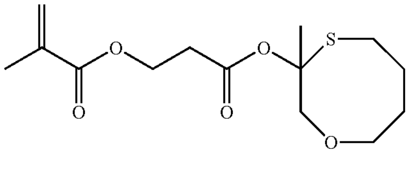

Production Process for (Meth)Acrylic Ester Derivative (1):

A production process for the (meth)acrylic derivative (1) shall not specifically be restricted, and it can be produced, for example, by reacting the alcohol (2) with the halocarboxylic halide (3) and a compound represented by a formula ($X^1$—W—CO)$_2$O, a formula $X^1$—W—COOC(=O)$R^{11}$ or a formula $X^1$—W—$COOSO_2R^{12}$ (hereinafter the above compounds shall be referred to as linking group-introducing agents) in the presence of a basic substance (hereinafter referred to as a first step) and then reacting the compound obtained above with the (meth)acrylic acid (5) in the presence of a basic substance (hereinafter referred to as a second step).

In the linking group-introducing agent described above, W is the same as defined above. $X^1$ and $X^2$ each represent independently a chlorine atom, a bromine atom or an iodine atom, and they are preferably a chlorine atom or a bromine atom. $R^{11}$ represents t-butyl or 2,4,6-trichlorophenyl. $R^{12}$ represents methyl or p-tolyl.

First Step:

Among the linking group-introducing agents used in the first step, the specific examples of the halocarboxylic halide (3) include, for example, chloroacetic chloride, bromoacetic bromide, 3-chloropropionic chloride, 3-bromopropionic chloride, 4-chlorobutyric chloride, 4-bromobutyric chloride, 5-chlorovaleric chloride, 2-chloropropionic chloride, 2-bromopropionic chloride, 2-bromopropionic bromide, 2-bromoisobutyric bromide, 3-chloropivalic chloride and the like.

The compound represented by the formula ($X^1$—W—CO)$_2$O includes, for example, chloroacetic anhydride, 2-chloropropionic anhydride and the like.

The compound represented by the formula $X^1$—W—COOC(=O)$R^{11}$ includes, for example, chloroacetic pivalic anhydride, chloroacetic 2,4,6-trichlorobenzoic anhydride, 2-chloropropionic pivalic anhydride, 2-chloropropionic 2,4,6-trichlorobenzoic anhydride and the like.

The compound represented by the formula $X^1$—W—$COOSO_2R^{12}$ includes chloroacetic methanesulfonic anhydride, chloroacetic p-toluenesulfonic anhydride, 2-chloropropionic methanesulfonic anhydride, 2-chloropropionic p-toluenesulfonic anhydride and the like.

A used amount of the linking group-introducing agent falls in a range of preferably 0.5 to 5 mole per 1 mole of the alcohol (2), and it falls in a range of more preferably 0.8 to 3 mole from the viewpoints of an economical efficiency and easiness of after-treatment.

The basic substance used in the first step includes, for example, alkali metal hydrides such as sodium hydride, potassium hydride and the like; alkali earth metal hydrides such as magnesium hydride, calcium hydride and the like; alkali metal hydroxides such as sodium hydroxide, potassium hydroxide and the like; alkali earth metal hydroxides such as magnesium hydroxide, calcium hydroxide and the like; alkali metal carbonates such as sodium carbonate, potassium carbonate and the like; alkali earth metal carbonates such as magnesium carbonate, calcium carbonate and the like; alkali metal hydrogencarbonates such as sodium hydrogencarbonate, potassium hydrogencarbonate and the like; tertiary amines such as triethylamine, tributylamine, diisopropylethylamine, 1,4-diazabicyclo[2.2.2]octane and the like; nitrogen-containing heterocyclic aromatic compounds such as pyridine, 2-picoline, 2,6-lutidine and the like.

A used amount of the basic substance falls in a range of preferably 0.5 to 5 mole per 1 mole of the alcohol (2), and it falls in a range of more preferably 0.8 to 3 mole from the viewpoints of an economical efficiency and easiness of after-treatment.

The first step can be carried out in the presence or the absence of a solvent. The solvent shall not specifically be restricted as long as the reaction is not inhibited, and it includes, for example, aliphatic hydrocarbons such as hexane, heptane, octane and the like; aromatic hydrocarbons such as benzene, toluene, xylene, mesitylene and the like; halogenated aromatic hydrocarbons such as chlorobenzene, fluorobenzene and the like, ethers such as diethyl ether, diisopropyl ether, dibutyl ether, tetrahydrofuran, dioxane, 1,2-dimethoxyethane, diglyme, triglyme, tetraglyme and the like; halogenated aliphatic hydrocarbons such as dichloromethane, chloroform, 1,2-dichloroethane and the like;

acetonitrile and the like. They may be used alone or in a mixture of two or more kinds thereof.

When the solvent is used, a used amount thereof is preferably 100 parts by mass or less, more preferably 50 parts by mass or less and further preferably 10 parts by mass or less per 1 part by mass of the alcohol (2) from the viewpoints of the reaction rate and an amount of the waste solvent.

A reaction temperature in the first step is varied depending on the kinds of the alcohol (2) used, the linking group-introducing agent and the basic substance, and it falls in a range of preferably −50 to 200° C., more preferably −30 to 100° C.

A pressure in the first step shall not specifically be restricted, and the reaction is carried out preferably at atmospheric pressure since it is simple.

A reaction time in the first step is varied depending on the kinds of the alcohol (2), the linking group-introducing agent and the basic substance and the reaction temperature, and it falls usually in a range of preferably 0.5 to 48 hours, more preferably 1 to 24 hours.

A reaction operation method in the first step shall not specifically be restricted. Further, an addition method and an addition order of the reactants shall not specifically be restricted as well, and the reactants can be added according to an optional method and an optional order. The reaction operation method is preferably a method in which a batch type reaction vessel is charged with the alcohol (2), the basic substance and, if necessary, the solvent and in which the linking group-introducing agent is added to the mixture obtained above at a prescribed temperature.

The reaction of the first step can be terminated by adding water and/or alcohol. The above alcohol includes, for example, methanol, ethanol, n-propanol, i-propanol and the like.

When the reaction is terminated by adding water and/or alcohol, a used amount thereof is preferably 1.0 mole or more per mole of the linking group-introducing agent which is excessive over the alcohol (2). The above used amount makes it possible to completely decompose the excessive linking group-introducing agent and inhibit by-products from being produced.

A method for separating and refining the haloester derivative (4) from the reaction mixture obtained by the method described above shall not specifically be restricted, and it can be carried out by a method usually used for separating and refining organic compounds. The haloester derivative (4) can be separated, for example, by adding water to the reaction mixture after finishing the reaction, then extracting it with an organic solvent and concentrating the organic layer obtained. The haloester derivative (4) having a high purity can be obtained by refining it, if necessary, by methods such as recrystallization, distillation, silica gel chromatography and the like. The haloester derivative (4) obtained in the first step can be used as well for a subsequent step (a second step described later) as it is without separating from the reaction mixture and refining it.

A method for producing the alcohol (2) used as the raw material in the first step shall not specifically be restricted, and 1,4-oxathiane-2-ol can be obtained by subjecting (2-hydroxyethylthio)acetaldehyde=dimethyl=acetal which can be produced from mercaptoethanol and chloroacetaldehyde=dimethyl=acetal to dealcoholization of methanol in the presence of an acid catalyst.

The specific examples of the haloester derivative (4) obtained in the manner described above include the following compounds but shall not specifically be restricted them.

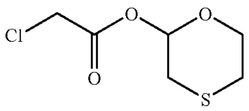
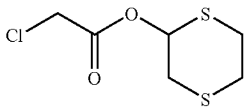
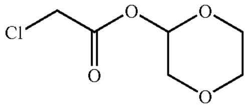
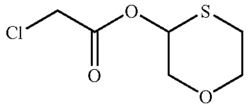
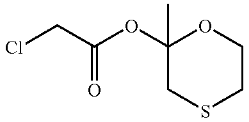
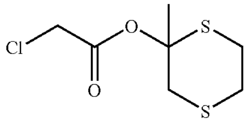
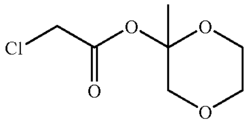
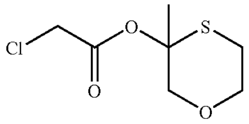
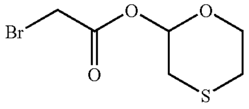
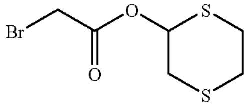
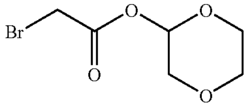
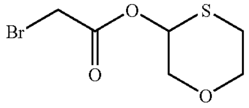
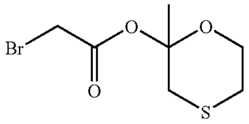
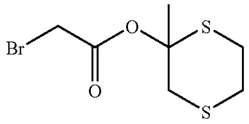
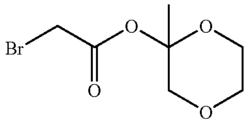
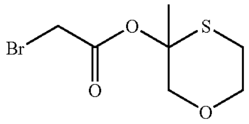
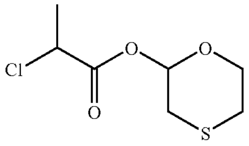
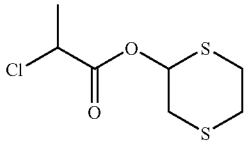
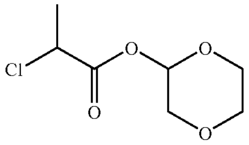
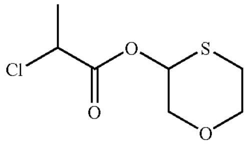
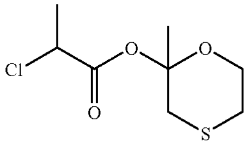
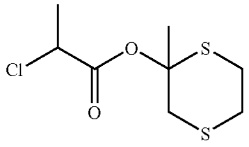
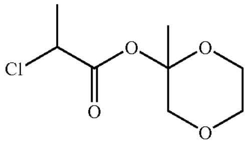
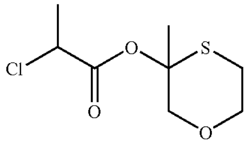
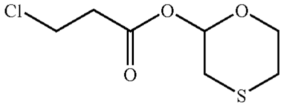
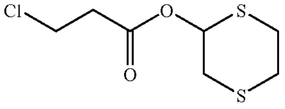
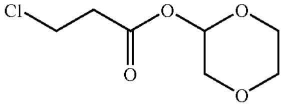
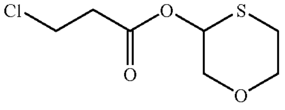

-continued
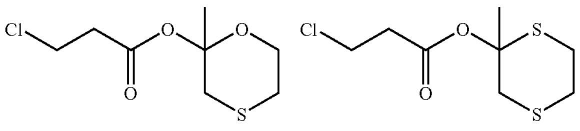
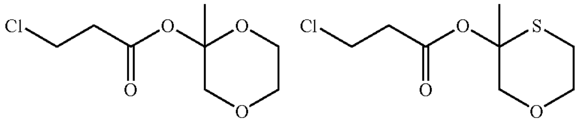
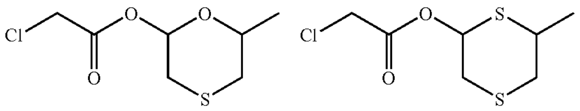
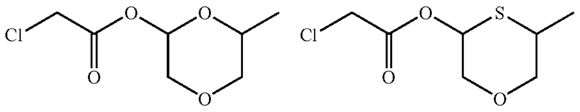
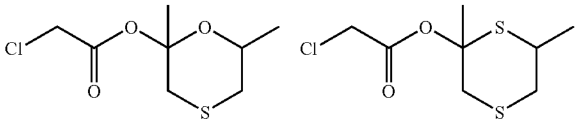
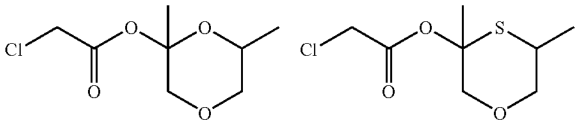
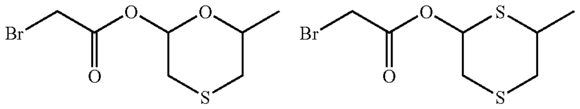
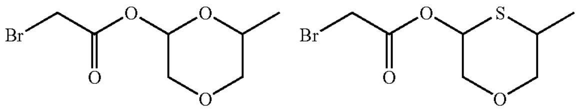
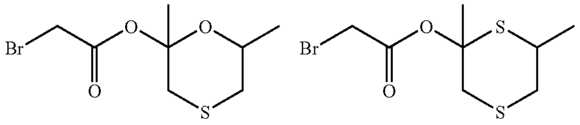
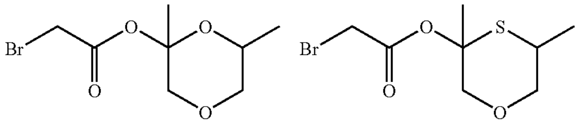
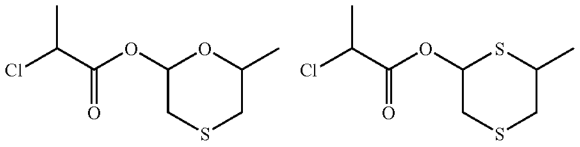
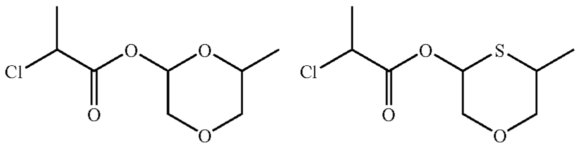
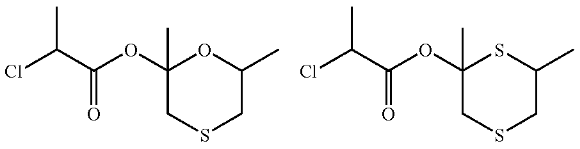
-continued
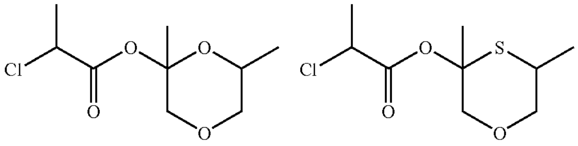
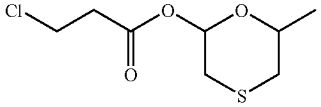
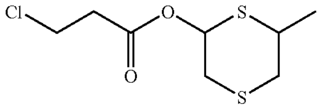
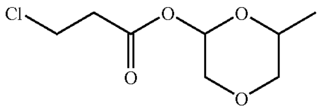
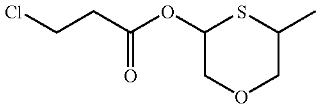
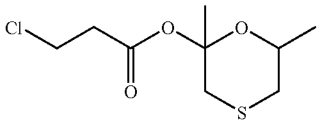
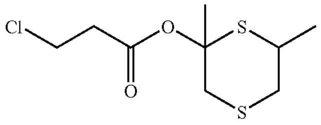
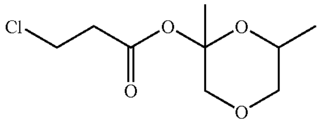
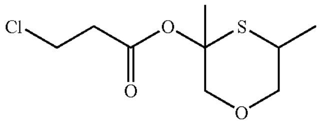
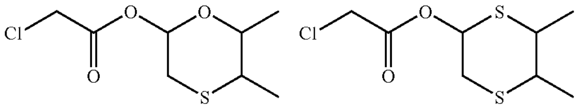
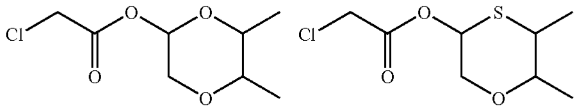
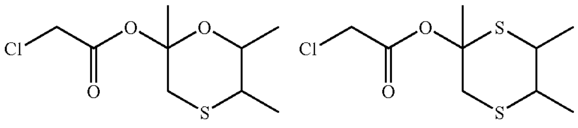
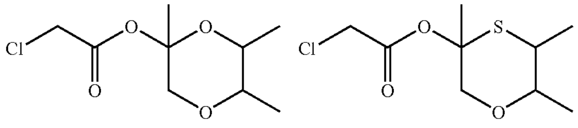
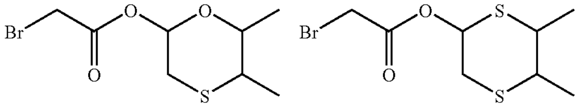

-continued
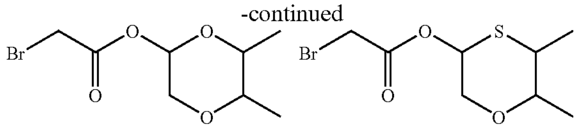
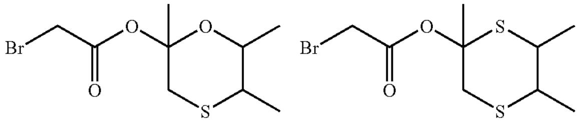
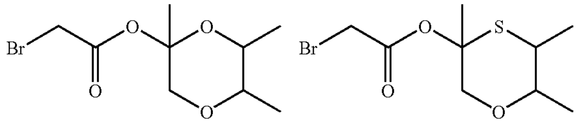
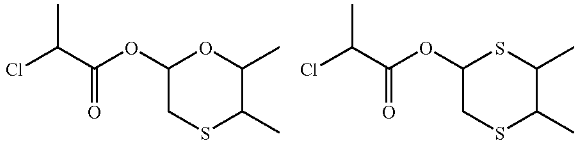
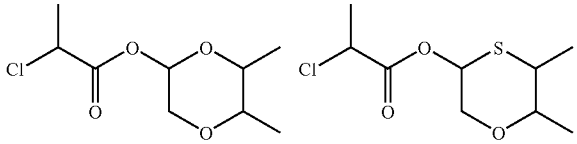
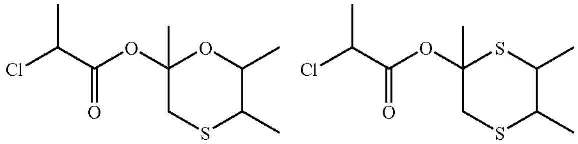
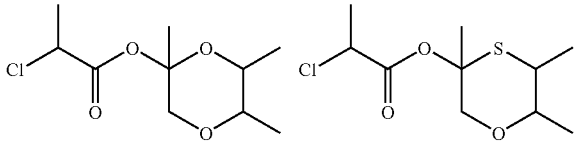
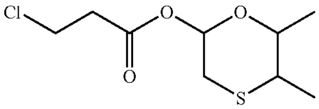
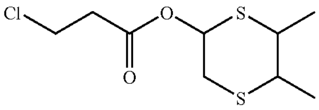
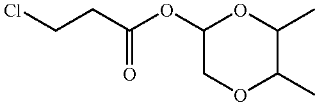
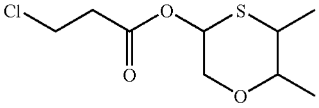
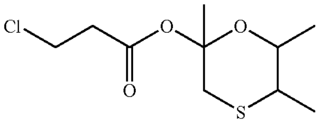
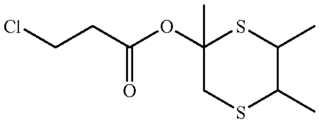
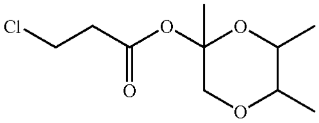
-continued
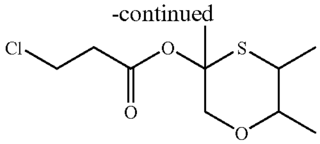
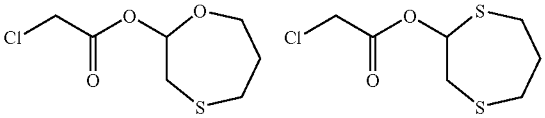
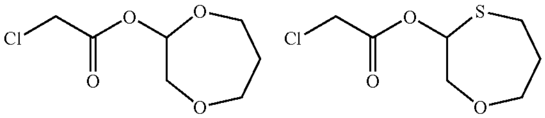
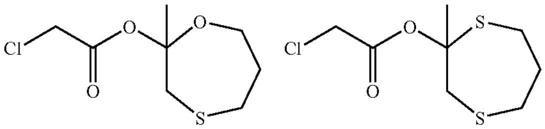
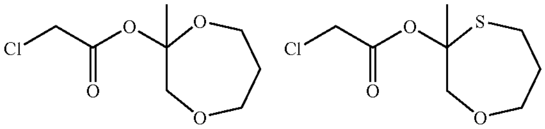
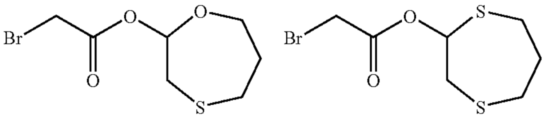
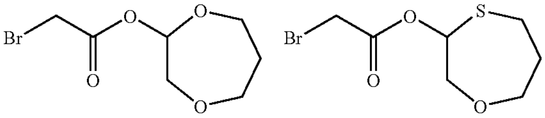
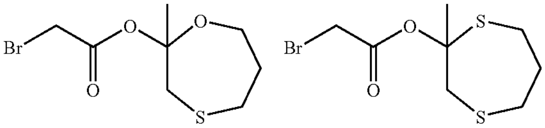
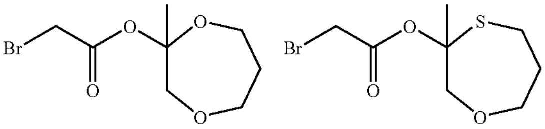
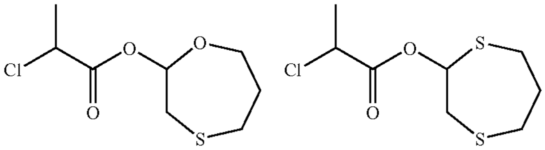
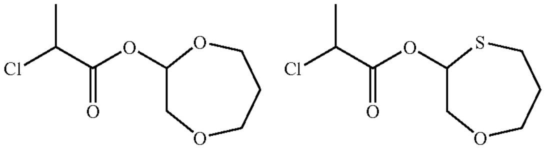
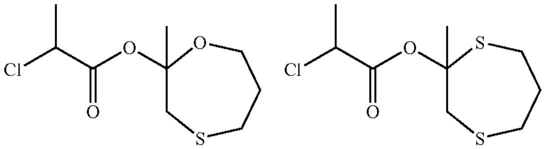
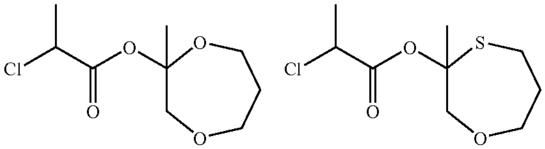

-continued
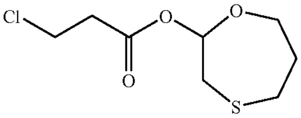
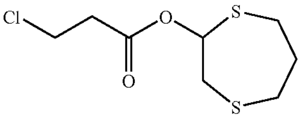
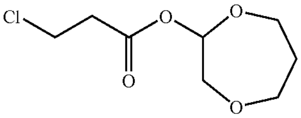
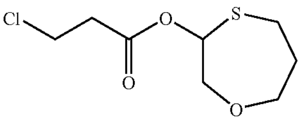
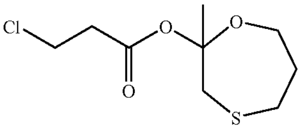
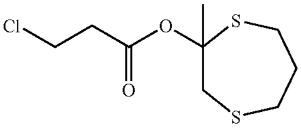
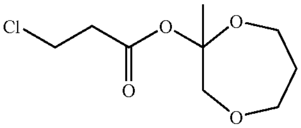
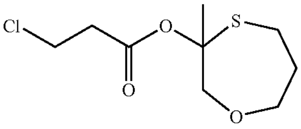
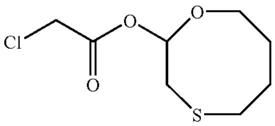
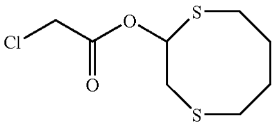
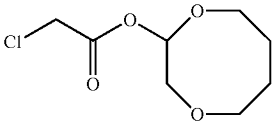
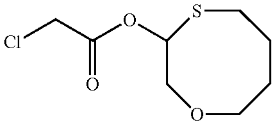
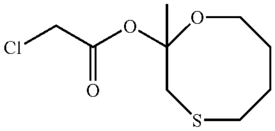
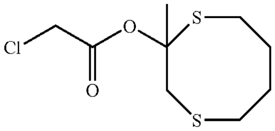
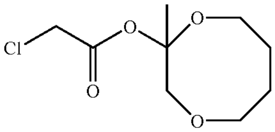
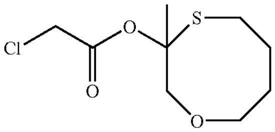
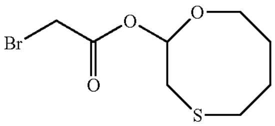
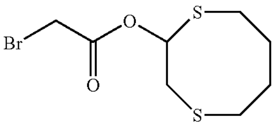
-continued
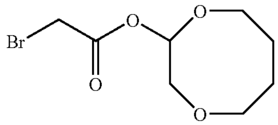
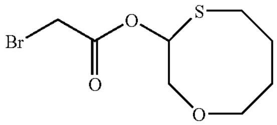
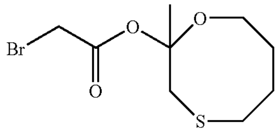
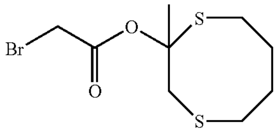
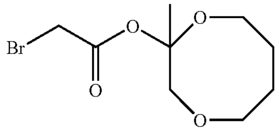
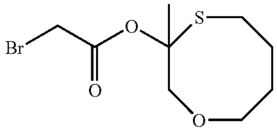
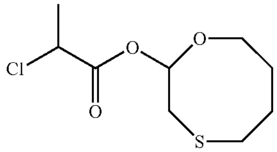
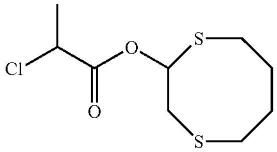
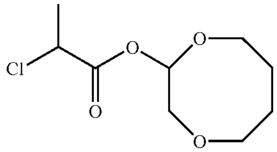
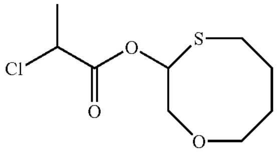
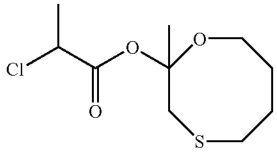
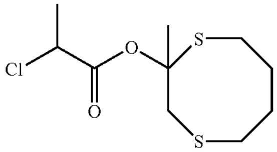
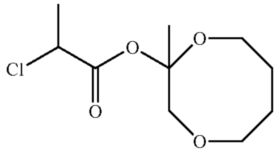
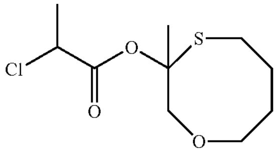
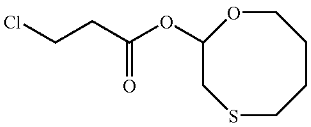
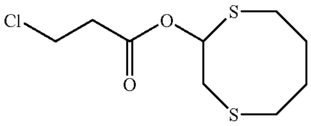
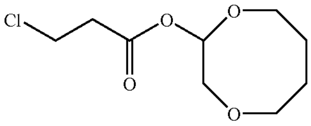
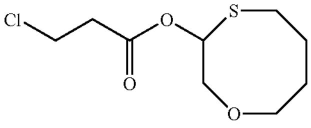
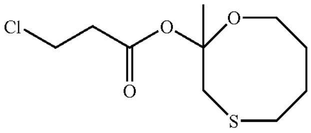

-continued

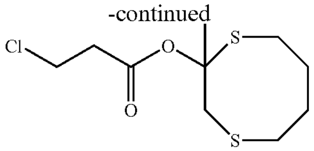

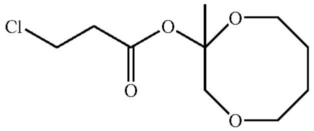

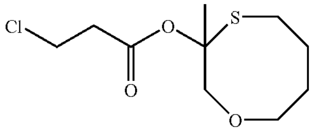

Second Step:

The second step shall be explained below.

The (meth)acrylic acid (5) used in the second step includes acrylic acid, methacrylic acid and 2-(trifluoromethyl)acrylic acid.

A used amount of the (meth)acrylic acid (5) falls in a range of preferably 0.8 to 10 mole, more preferably 1 to 5 mole per 1 mole of the haloester derivative (4).

The basic substance used in the second step includes the same compounds as the basic substances used in the first step. Among them, alkali metal or alkali earth metal carbonates such as sodium carbonate, potassium carbonate, calcium carbonate, lithium carbonate and the like and hydrides of alkali metals such as sodium hydride and the like are preferably used. They may be used, if necessary, in the form of an aqueous solution. A used amount of the basic substance falls in a range of preferably 0.5 to 10 mole, more preferably 0.7 to 3 mole per 1 mole of the haloester derivative (4).

In the second step, potassium iodide, sodium iodide, tetrabutylammonium iodide, tetrabutylammonium bromide and the like are preferably used, if necessary, as an activating agent.

A used amount of the activating agent falls in a range of preferably 0.001 to 1 mole per 1 mole of the haloester derivative (4), and it falls in a range of more preferably 0.005 to 0.5 mole from the viewpoints of easiness of after-treatment and an economical efficiency.

The second step can be carried out in the presence or the absence of a polymerization inhibitor. The polymerization inhibitor shall not specifically be restricted, and capable of being used are, for example, quinones such as hydroquinone, methoxyphenol, benzoquinone, toluquinone, p-tert-butylcatechol and the like; alkylphenols such as 2,6-di-tert-butylphenol, 2,4-di-tert-butylphenol, 2-tert-butyl-4,6-dimethylphenol and the like; amines such as phenothiazine and the like. They may be used alone or in a mixture of two or more kinds thereof.

When the polymerization inhibitor is used, a used amount thereof is preferably 5% by mass or less, more preferably 1% by mass or less and further preferably 0.5% by mass or less per the whole mass of the reaction mixture.

The second step can be carried out in the presence or the absence of a solvent. The solvent shall not specifically be restricted as long as the reaction is not inhibited. The above solvent includes, for example, aliphatic hydrocarbons such as hexane, heptane, octane and the like; aromatic hydrocarbons such as benzene, toluene, xylene, mesitylene and the like; halogenated aromatic hydrocarbons such as chlorobenzene, fluorobenzene and the like; ethers such as diethyl ether, diisopropyl ether, dibutyl ether, tetrahydrofuran, dioxane, 1,2-dimethoxyethane, diglyme, triglyme, tetraglyme and the like; halogenated aliphatic hydrocarbons such as dichloromethane, chloroform, 1,2-dichloroethane and the like; amides such as N,N-dimethylformamide, N,N-dimethylacetamide, N-methylpyrrolidone and the like. They may be used alone or in a mixture of two or more kinds thereof.

When the solvent is used, a used amount thereof is preferably 100 parts by mass or less, more preferably 50 parts by mass or less and further preferably 10 parts by mass or less per 1 part by mass of the haloester derivative (4) from the viewpoints of the reaction rate and an amount of the waste solvent.

A reaction temperature in the second step is varied depending on the kinds of the haloester derivative (4), the (meth) acrylic acid (5), the basic substance and the activating agent, and it falls in a range of preferably −50 to 180° C., more preferably −30 to 130° C.

A pressure in the second step shall not specifically be restricted, and the reaction is carried out preferably at atmospheric pressure since it is simple.

A reaction time in the second step is varied depending on the kinds of the haloester derivative (4), the (meth)acrylic acid (5), the basic substance and the activating agent and the reaction temperature, and it falls usually in a range of preferably 0.5 to 48 hours, more preferably 1 to 24 hours.

A reaction operation method in the second step shall not specifically be restricted. Further, an addition method and an addition order of the reactants shall not specifically be restricted as well, and the reactants can be added according to an optional method and an optional order. The reaction operation method is preferably a method in which a batch type reaction vessel is charged with the basic substance, the (meth) acrylic acid (5), the activating agent, the polymerization inhibitor and, if necessary, the solvent and in which the haloester derivative (4) is added to the mixture obtained above at a prescribed temperature.

A method for separating and refining the (meth)acrylic ester derivative (1) from the reaction mixture obtained in the second step can be carried out by a method usually used for separating and refining organic compounds. The (meth) acrylic ester derivative (1) can be separated, for example, by adding water to the reaction mixture after finishing the reaction, then extracting it with an organic solvent and concentrating the organic layer obtained. Further, the (meth)acrylic ester derivative (1) having a high purity can be obtained by refining it, if necessary, by methods such as recrystallization, distillation, silica gel chromatography and the like.

Further, it is possible as well to reduce, if necessary, a metal content in the (meth)acrylic ester derivative (1) by adding a chelating agent such as nitrilotriacetic acid, ethylenediaminetetraacetic acid and the like to the reaction mixture and then filtrating or subjecting it to metal removing filter treatment with Zeta Plus (trade name: manufactured by Sumitomo 3M limited), Protego (trade name: manufactured by Japan Entegris Co., Ltd.), IonClean (trade name: manufactured by Nihon Pall Ltd.) and the like.

Polymer (6):

A polymer (hereinafter referred to as a polymer (6)) is prepared by polymerizing a raw material containing at least the (meth)acrylic ester derivative (1), whereby it can be used as a component for a photoresist composition.

The polymer (6) is a polymer prepared by homopolymerizing the (meth)acrylic ester derivative (1) or a copolymer prepared by copolymerizing the (meth)acrylic ester derivative (1) with other polymerizable compounds, and it has a structural unit per the (meth)acrylic ester derivative (1). Usually, a content of the structural unit based on the (meth)acrylic ester derivative (1) in the above polymer falls in a range of preferably 10 to 80 mole %, more preferably 20 to 70 mole %.
The specific examples of the structural unit based on the (meth)acrylic ester derivative (1) include units represented by the following formulas, but they shall not be restricted to these units.
(1′-a)
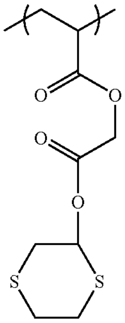
(1′-b)
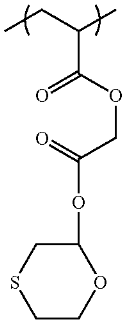
(1′-c)
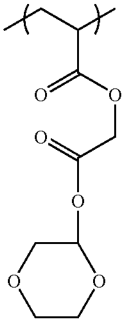
(1′-a′)
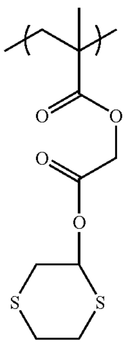
-continued
(1′-b′)
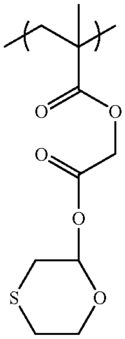
(1′-c′)
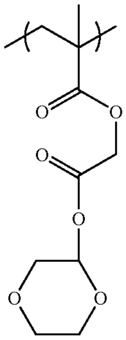
(1′-d)
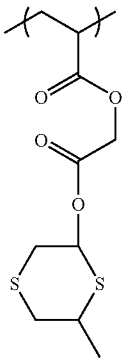
(1′-e)
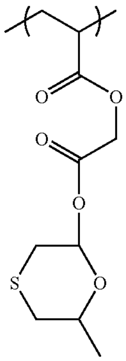

-continued
(1′-f)
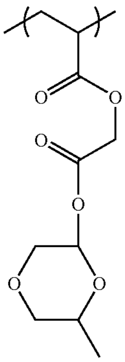
(1′-d′)
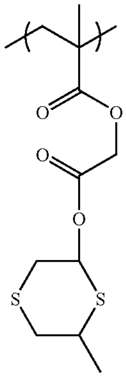
(1′-e′)
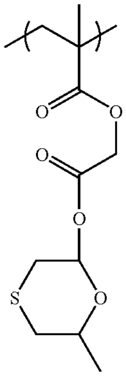
(1′-f′)
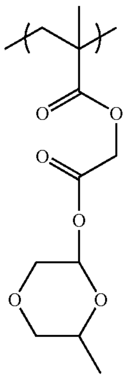
-continued
(1′-g)
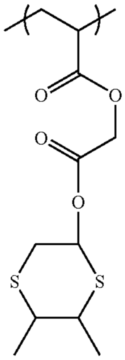
(1′-h)
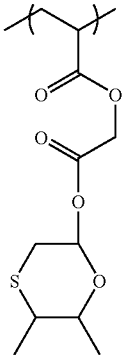
(1′-i)
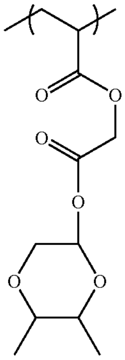
(1′-g′)
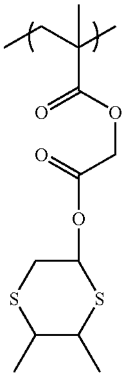

-continued
(1′-h′)
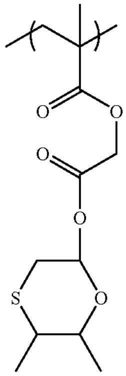
(1′-i′)
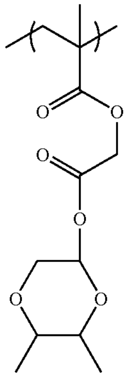
(1′-j)
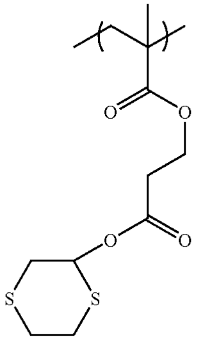
(1′-k)
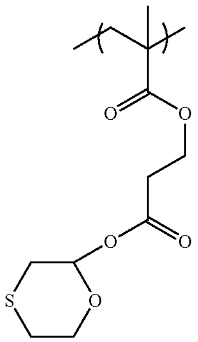
-continued
(1′-l)
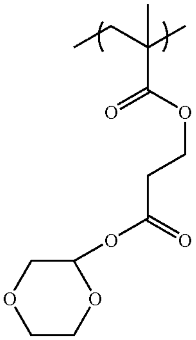
(1′-m)
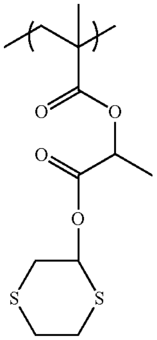
(1′-n)
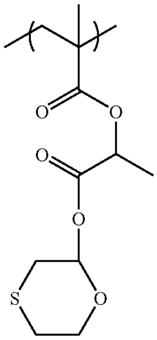
(1′-o)
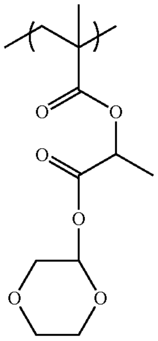

-continued
(1′-p)
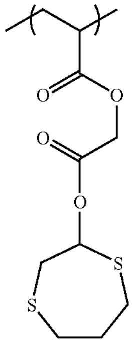
(1′-q)
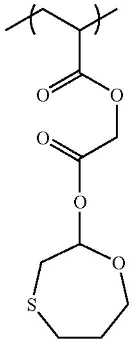
(1′-r)
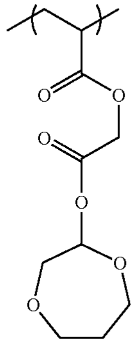
(1′-p′)
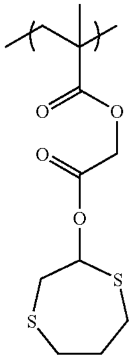
-continued
(1′-q′)
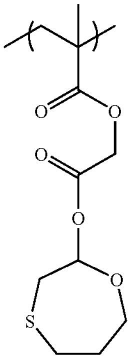
(1′-r′)
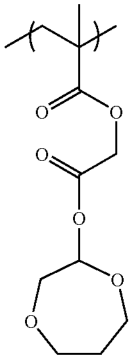
(1′-s)
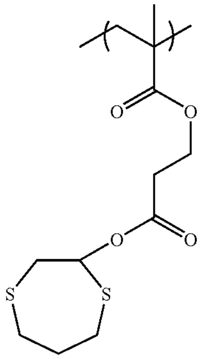
(1′-t)
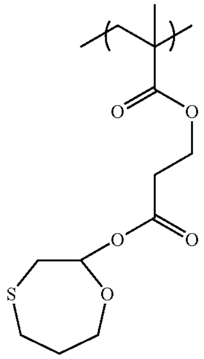

-continued
(1′-u)
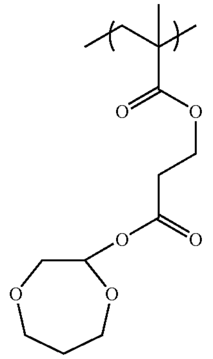
(1′-v)
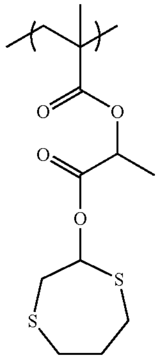
(1′-w)
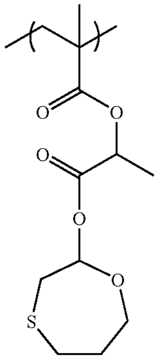
(1′-x)
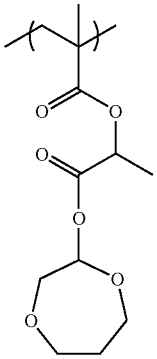
-continued
(1′-y)
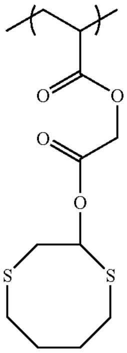
(1′-z)
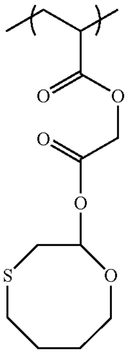
(1′-A)
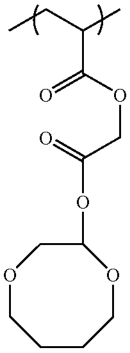
(1′-y′)
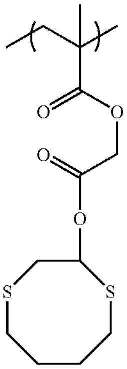

-continued
(1′-z′)
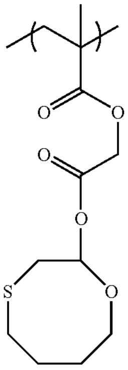
(1′-A′)
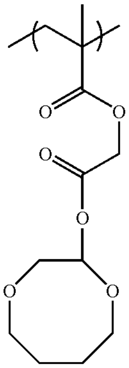
(1′-B)
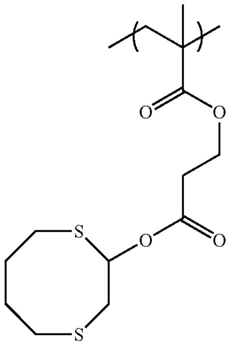
(1′-C)
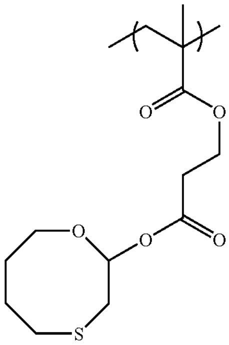
-continued
(1′-D)
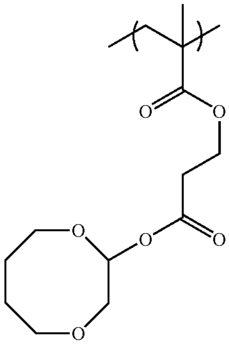
(1′-E)
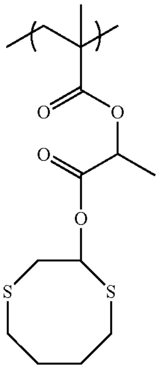
(1′-F)
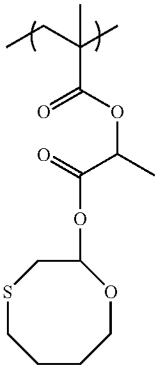
(1′-G)
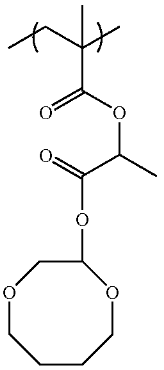
The specific examples of the other polymerizable compounds (hereinafter referred to as the copolymerization monomer (7)) which can be copolymerized with the (meth) acrylic ester derivative (1) include, for example, compounds (I) to (IX) represented by the following chemical formulas:

(I)

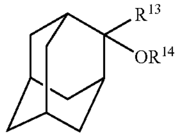

(II)

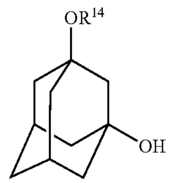

(III)

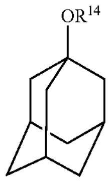

(IV)

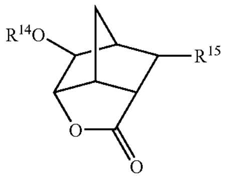

(V)

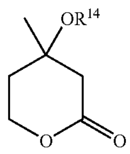

(VI)

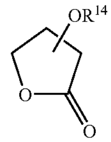

(VII)

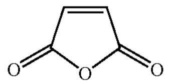

(VIII)

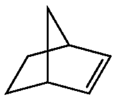

(IX)

$R^{14}$—O—$R^{17}$ (wherein $R^{13}$ represents a hydrogen atom or an alkyl group having 1 to 3 carbon atoms; $R^{14}$ represents a polymerizable group; $R^{15}$ represents a hydrogen atom or —$COOR^{16}$, and $R^{16}$ represents an alkyl group having 1 to 3 carbon atoms; and $R^{17}$ represents an alkyl group or a cycloalkyl group in which a carbon atom forming a ring may be substituted with an oxygen atom), but they shall not specifically be restricted to these compounds.

In the copolymerization monomer (7), the alkyl group having 1 to 3 carbon atoms each represented independently by $R^{13}$ and $R^{16}$ includes methyl, ethyl, n-propyl and isopropyl. The alkyl group represented by $R^{17}$ includes, for example, methyl, ethyl, n-propyl, isopropyl, n-butyl, isobutyl, s-butyl, t-butyl and the like. The cycloalkyl group represented by $R^{17}$ in which a carbon atom forming a ring may be substituted with an oxygen atom includes, for example, cyclopentyl, cyclohexyl, 1-methylcyclohexyl, cyclooctyl, tetrahydropyran-2-yl, 4-methyltetrahydropyran-4-yl and the like. The polymerizable group represented by $R^{14}$ includes, for example, acryloyl, methacryloyl, 2-(trifluoromethyl)acryloyl, vinyl, crotonoyl and the like.

$R^{13}$ is preferably a hydrogen atom, methyl, ethyl or isopropyl. $R^{14}$ is preferably acryloyl or methacryloyl. $R^{15}$ is preferably a hydrogen atom. $R^{17}$ is preferably an alkyl group having 1 to 8 carbon atoms.

The copolymerization monomer (7) is preferably the compound (I), (II), (IV), (V), (VI) or (IX) each described above, more preferably the compound (II), (IV) or (VI), Production Process for the Polymer (6):

The polymer (6) can be produced by radical polymerization according to a conventional method. In particular, living radical polymerization can be listed as a method for synthesizing a polymer having a narrow molecular weight distribution. In a conventional radical polymerization method, at least one of the (meth)acrylic ester derivatives (1) according to necessity and at least one of the copolymerization monomers (7) according to necessity are polymerized in the presence of a radical polymerization initiator, a solvent and, if necessary, a chain transfer agent. The above radical polymerization method shall be explained below.

A method for carrying out the radical polymerization shall not specifically be restricted, and conventional methods used in producing, for example, acrylic polymers, such as a solution polymerization method, an emulsion polymerization method, a suspension polymerization method, a bulk polymerization method and the like can be used.

The radical polymerization initiator used for producing the polymer (6) of the present invention includes, for example, hydroperoxides such as t-butyl hydroperoxide, cumene hydroperoxide and the like; dialkyl peroxides such as di-t-butyl peroxide, t-butyl-α-cumyl peroxide, di-α-cumyl peroxide and the like; diacyl peroxides such as benzoyl peroxide, diisobutyryl peroxide and the like; and azo compounds such as 2,2'-azobisisobutyronitrile, dimethyl-2,2'-azobisisobutylate and the like.

A used amount of the radical polymerization initiator can suitably be selected according to the polymerization conditions such as the kinds and the used amounts of the (meth) acrylic ester derivative (1), the copolymerization monomer (7), the chain transfer agent and the solvent which are used for the polymerization reaction and the polymerization temperature and the like, and it falls usually in a range of preferably 0.005 to 0.2 mole, more preferably 0.01 to 0.15 mole per 1 mole of the whole polymerizable compounds (showing a total amount of the (meth)acrylic ester derivative (1) and the copolymerization monomer (7), and hereinafter the same shall apply).

The chain transfer agent includes, for example, thiols such as dodecanethiol, mercaptoethanol, mercaptopropanol, mercaptoacetic acid, mercaptopropionic acid and the like. They may be used alone or in a mixture of two or more kinds thereof.

When the chain transfer agent is used, a used amount thereof falls in a range of usually 0.005 to 0.2 mole, preferably 0.01 to 0.15 mole per 1 mole of the whole polymerizable compounds.

The polymer (6) of the present invention is produced usually in the presence of a solvent. The solvent shall not specifically be restricted as long as the reaction is not inhibited, and it includes, for example, glycol ethers such as propylene glycol monoethyl ether, propylene glycol monomethyl ether acetate, ethylene glycol monomethyl ether, ethylene glycol monomethyl ether acetate, ethylene glycol monomethyl ether propionate, ethylene glycol monobutyl ether, ethylene glycol monobutyl ether acetate, diethylene glycol dimethyl ether and the like; esters such as ethyl lactate, methyl 3-methoxypropionate, methyl acetate, ethyl acetate, propyl acetate and the like; ketones such as acetone, methyl ethyl ketone, methyl isopropyl ketone, methyl isobutyl ketone, methyl amyl ketone, cyclopentanone, cyclohexanone and the like; and ethers such as diethyl ether, diisopropyl ether, dibutyl ether, tetrahydrofuran, 1,4-dioxane and the like. They may be used alone or in a mixture of two or more kinds thereof.

A used amount of the solvent falls in a range of usually 0.5 to 20 parts by mass per 1 part by mass of the whole polymerizable compounds, and it falls in a range of preferably 1 to 10 parts by mass from the viewpoint of an economical efficiency.

A reaction temperature in the radical polymerization is usually 40 to 150° C., and it falls in a range of preferably 60 to 120° C. from the viewpoint of a stability of the polymer produced.

A reaction time in the radical polymerization is varied according to the polymerization conditions such as the kinds and the used amounts of the (meth)acrylic ester derivative (1), the copolymerization monomer (7), the polymerization initiator and the solvent, the reaction temperature of the polymerization and the like, and it falls usually in a range of preferably 0.5 to 48 hours, more preferably 1 to 24 hours.

The polymer thus obtained can be isolated by an ordinary operation such as reprecipitation and the like.

A solvent used in the operation of the reprecipitation described above includes, for example, aliphatic hydrocarbons such as pentane, hexane and the like; cyclic hydrocarbons such as cyclohexane and the like; aromatic hydrocarbons such as benzene, xylene and the like; halogenated hydrocarbons such as methylene chloride, chloroform, chlorobenzene, dichlorobenzene and the like; nitrated hydrocarbons such as nitromethane and the like; nitriles such as acetonitrile, benzonitrile and the like; ethers such as diethyl ether, diisopropyl ether, tetrahydrofuran, 1,4-dioxane and the like; ketones such as acetone, methyl ethyl ketone and the like; carboxylic acids such as acetic acid and the like; esters such as ethyl acetate, butyl acetate and the like; carbonates such as dimethyl carbonate, diethyl carbonate, ethylene carbonate and the like; alcohols such as methanol, ethanol, propanol, isopropyl alcohol, butanol and the like; and water. They may be used alone or in a mixture of two or more kinds thereof.

A used amount of the solvent is varied depending on the kind of the polymer and the kind of the solvent, and it falls usually in a range of preferably 0.5 to 100 parts by mass per 1 part by mass of the polymer; and it falls in a range of more preferably 1 to 50 parts by mass from the viewpoint of an economical efficiency.

The polymer thus isolated can be dried by vacuum drying and the like.

The specific examples of the polymer (6) obtained by the method described above include, for example, polymers represented by the following chemical formulas (wherein $R^{18}$ to $R^{30}$ each represent independently a hydrogen atom, methyl or trifluoromethyl; a, b, c, d and e represent the mole ratios of the repetitive units; a+b is equal to 1, and c+d+e is equal to 1), but they shall not be restricted to these compounds.

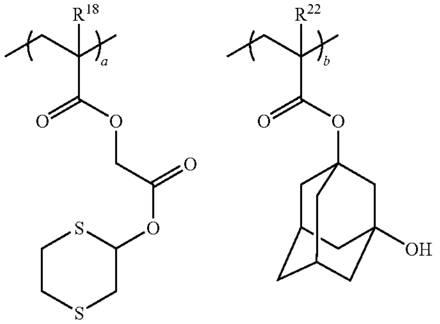

(6)-1

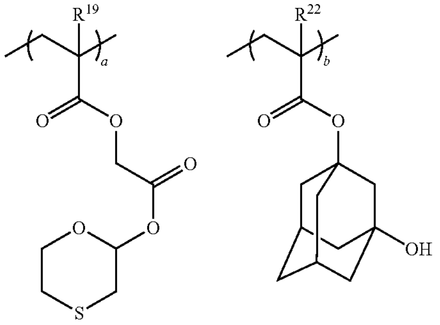

(6)-2

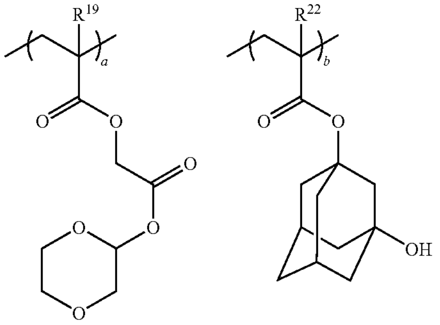

(6)-3

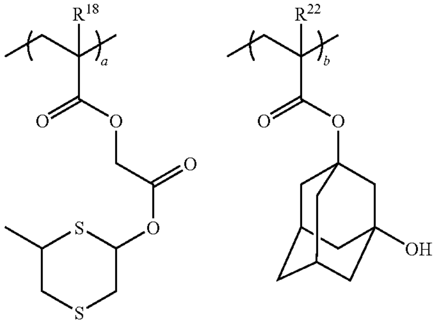

(6)-4

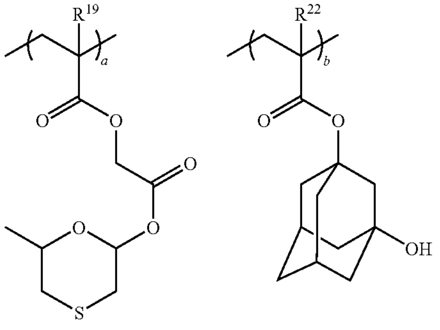

(6)-5

-continued
(6)-6
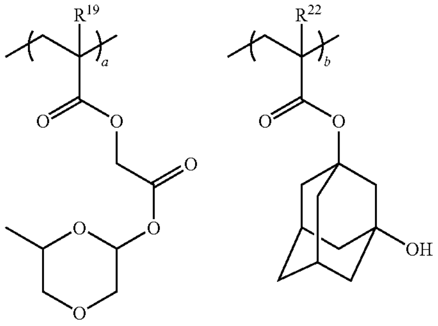
(6)-7
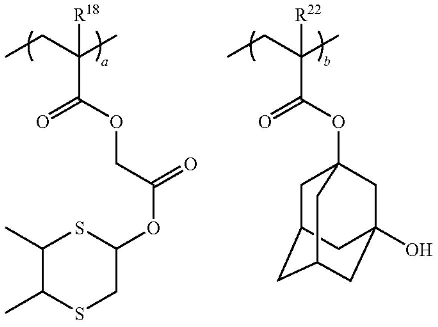
(6)-8
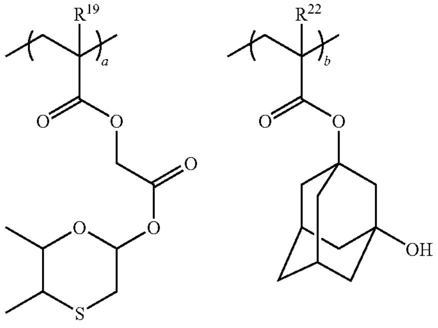
(6)-9
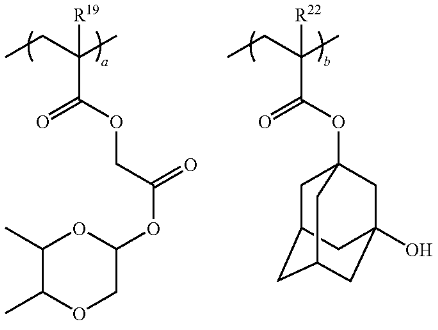
(6)-10
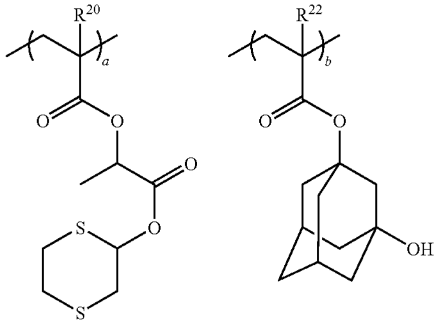
-continued
(6)-11
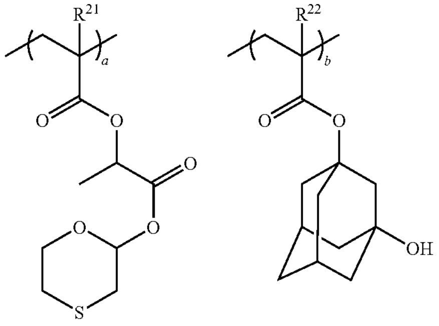
(6)-12
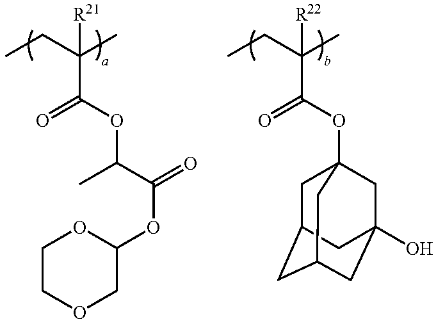
(6)-13
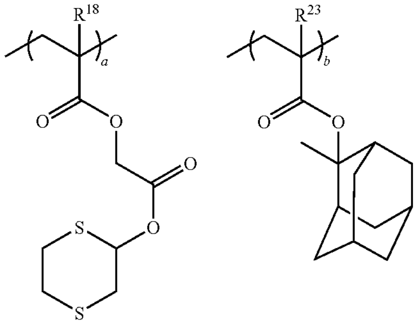
(6)-14
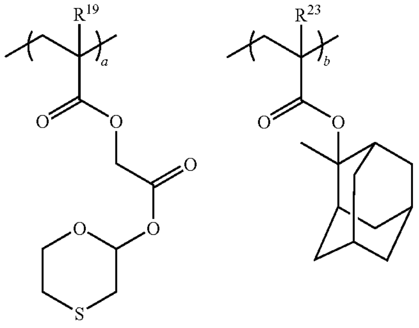
(6)-15
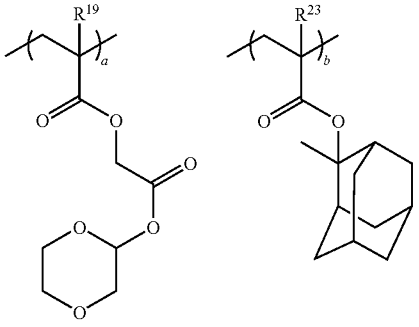

(6)-16
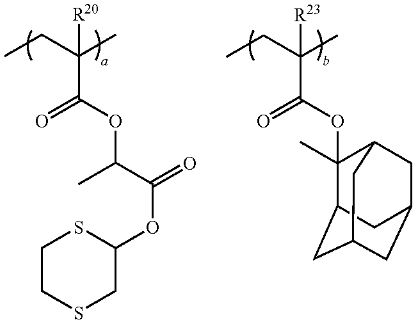
(6)-17
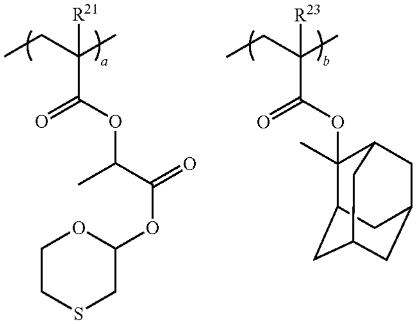
(6)-18
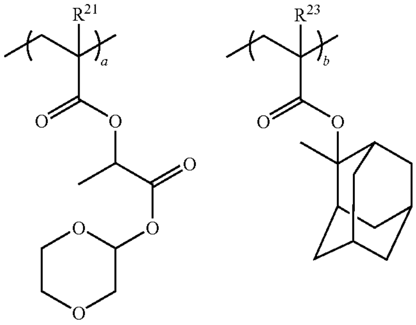
(6)-19
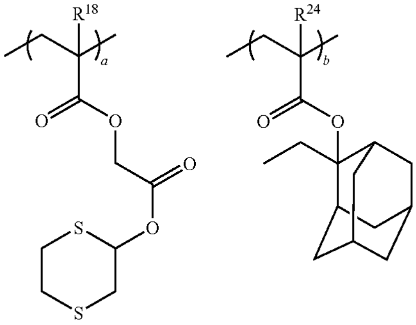
(6)-20
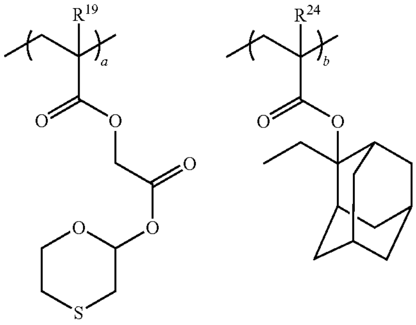
(6)-21
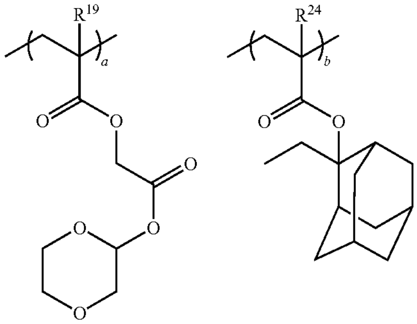
(6)-22
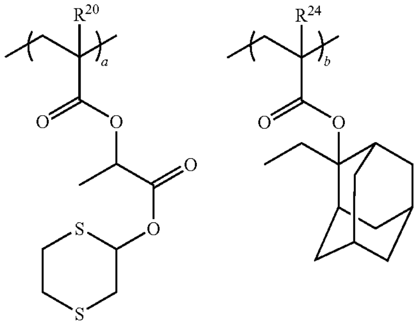
(6)-23
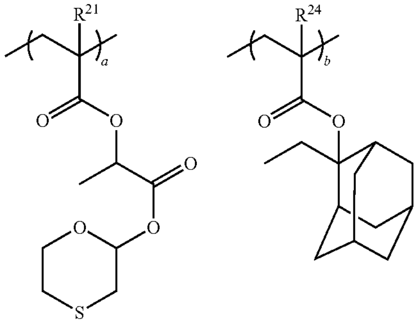
(6)-24
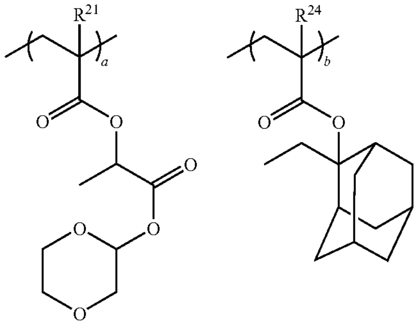

-continued
(6)-25
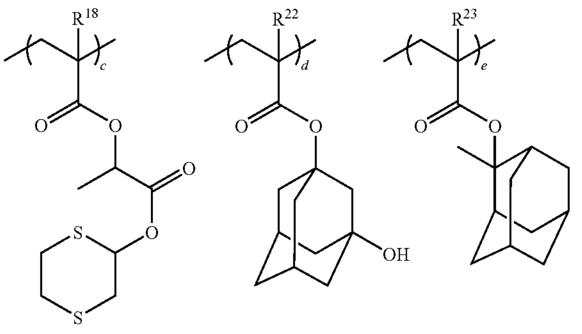
(6)-26
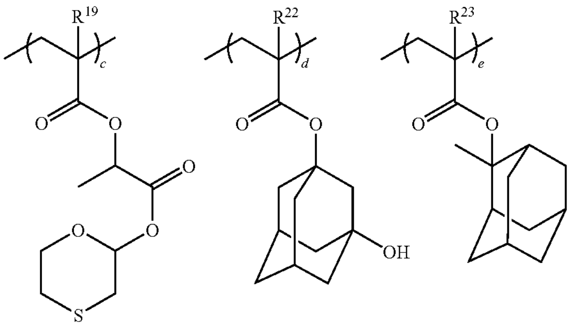
(6)-27
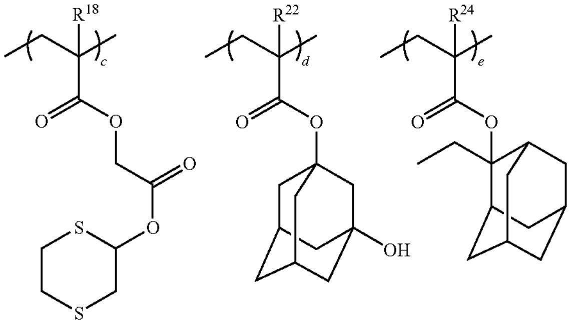
(6)-28
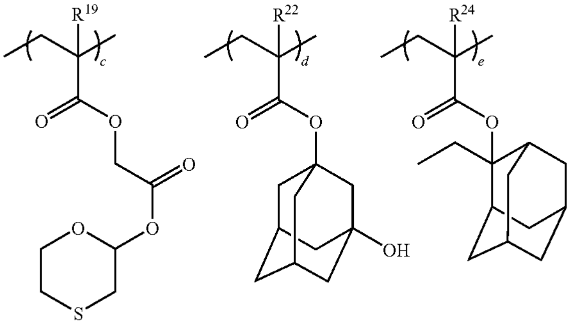
-continued
(6)-29
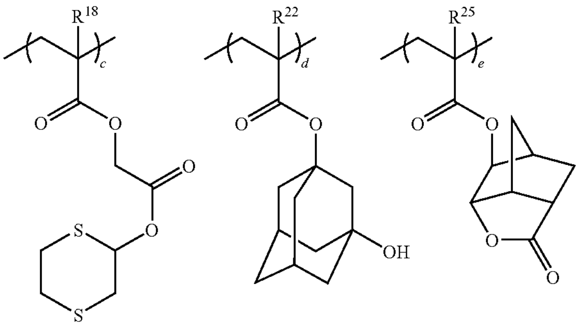
(6)-30
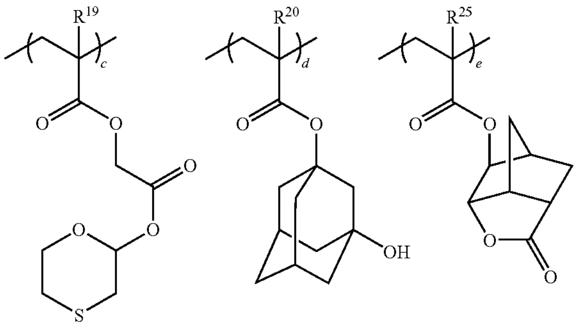
(6)-31
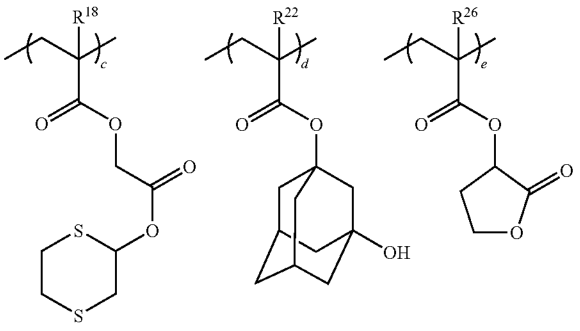
(6)-32
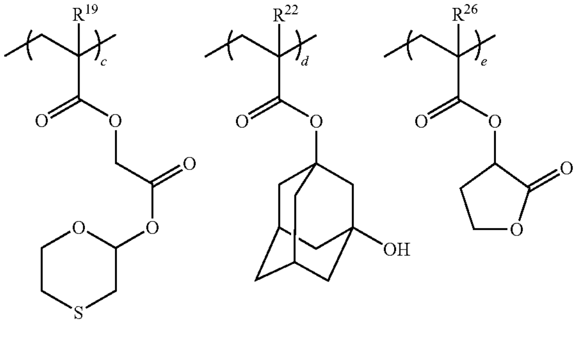

-continued
(6)-33
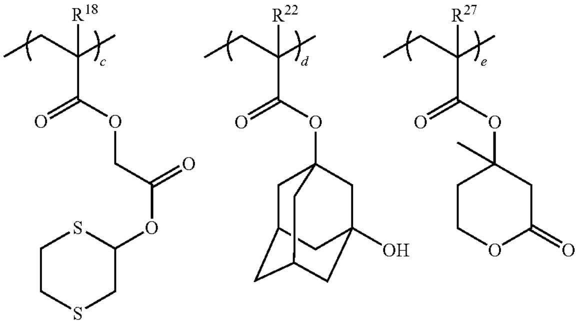
(6)-34
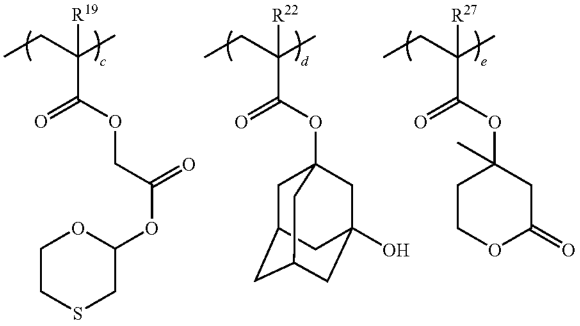
(6)-35
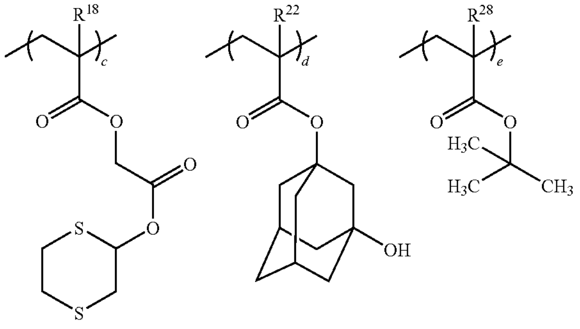
(6)-36
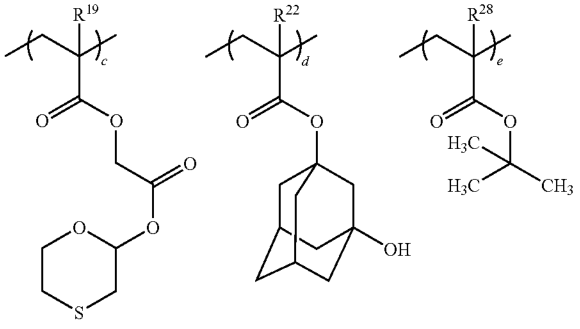
-continued
(6)-37
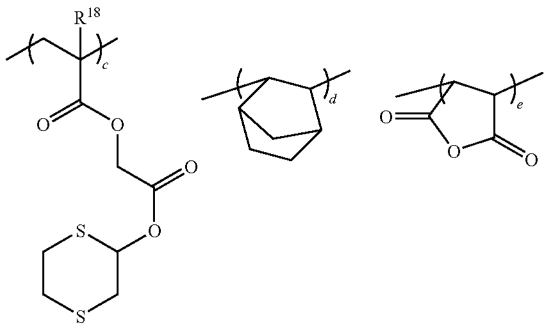
(6)-38
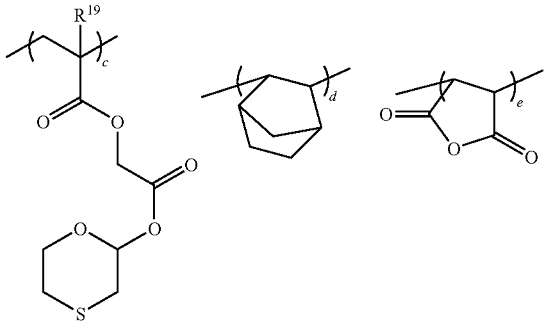
(6)-39
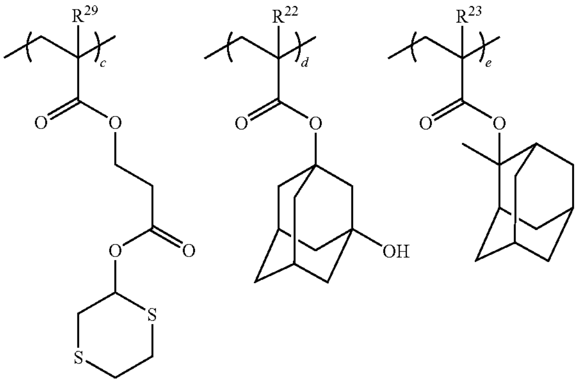
(6)-40
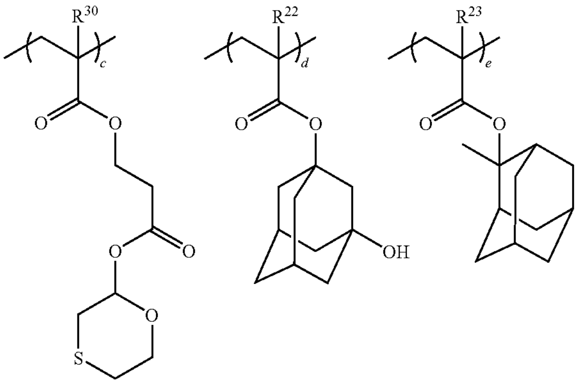

-continued
(6)-41
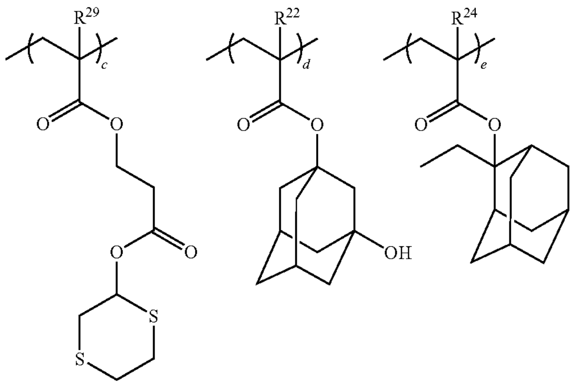
(6)-42
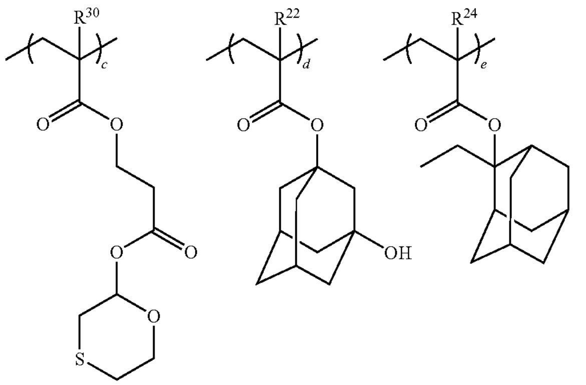
(6)-43
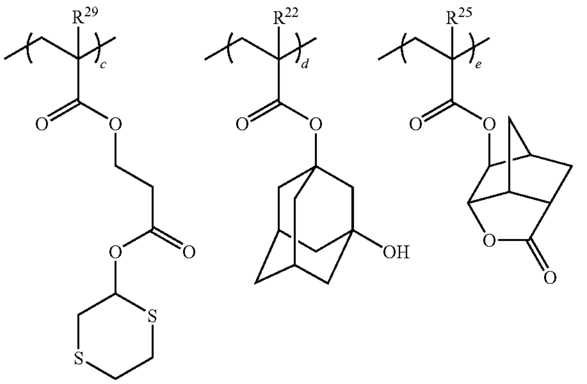
(6)-44
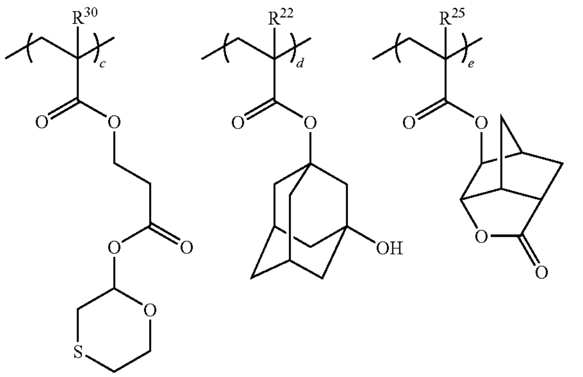
-continued
(6)-45
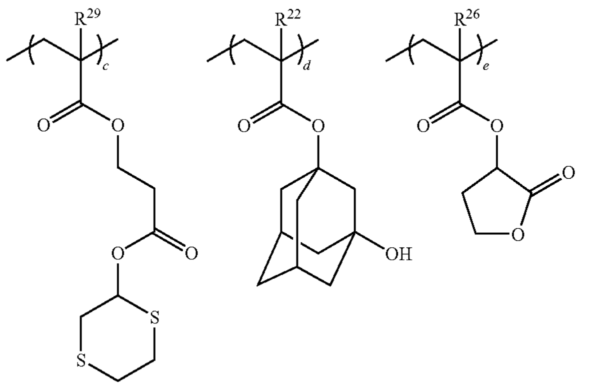
(6)-46
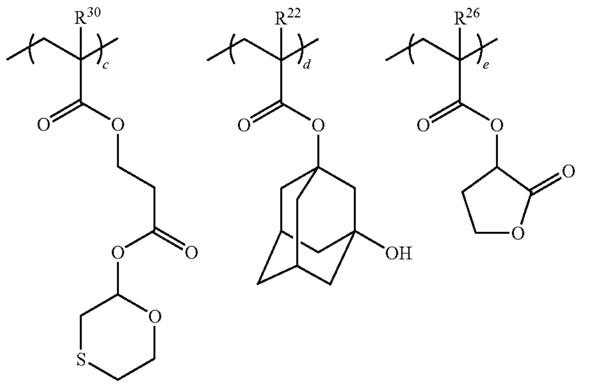
(6)-47
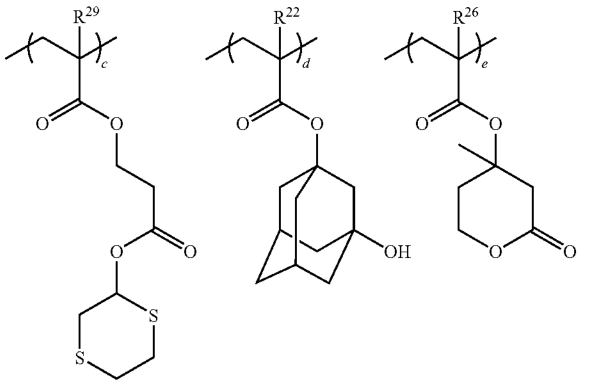
(6)-48
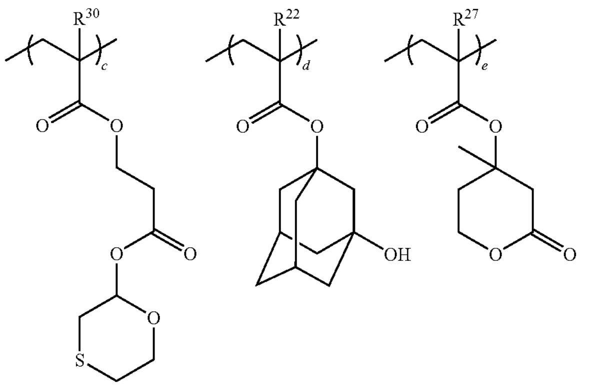

-continued (6)-49

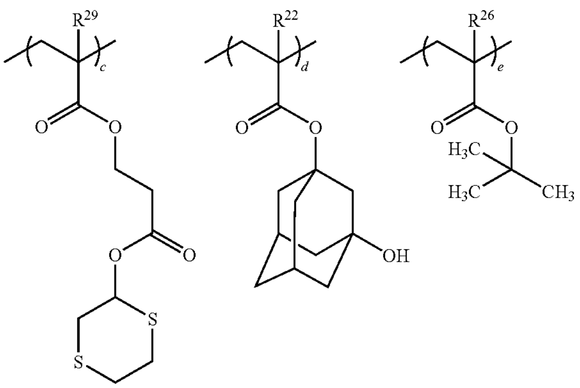

(6)-50

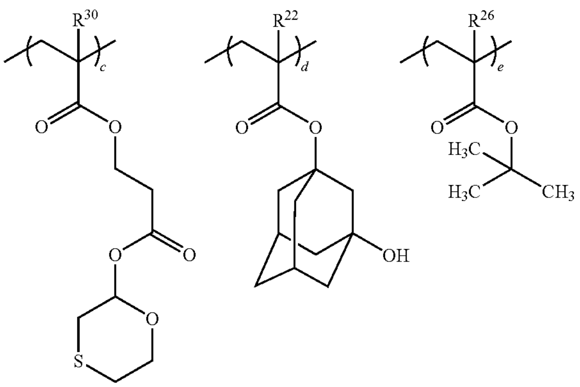

(6)-51

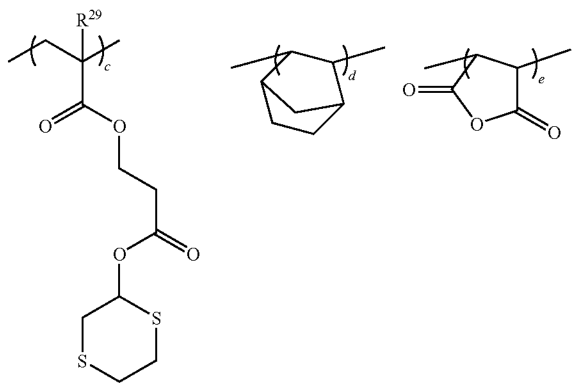

(6)-52

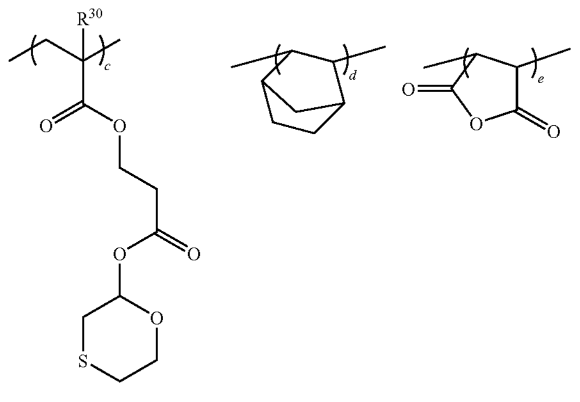

A weight average molecular weight (Mw) of the polymer (6) shall not specifically be restricted, and if it falls in a range of preferably 500 to 50,000, more preferably 1,000 to 30,000, a usefulness thereof as a component for a photoresist composition described later is high. The above weight average molecular weight (Mw) is measured in the manner described in the example.

Photoresist Composition:

A photoresist composition can be prepared by blending the polymer (6) with a solvent, a photoacid generator and, if necessary, a basic compound, a surfactant and other additives each described later.

The photoresist composition blended with the polymer (6) shall be explained below.

Solvent:

The solvent blended with the photoresist composition includes, for example, glycol ethers such as propylene glycol monoethyl ether, propylene glycol monomethyl ether acetate, ethylene glycol monomethyl ether, ethylene glycol monomethyl ether acetate, ethylene glycol monomethyl ether propionate, ethylene glycol monobutyl ether, ethylene glycol monobutyl ether acetate, diethylene glycol dimethyl ether and the like; esters such as ethyl lactate, methyl 3-methoxypropionate, methyl acetate, ethyl acetate, propyl acetate and the like; ketones such as acetone, methyl ethyl ketone, methyl isopropyl ketone, methyl isobutyl ketone, methyl amyl ketone, cyclopentanone, cyclohexanone and the like; and ethers such as diethyl ether, diisopropyl ether, dibutyl ether, tetrahydrofuran, 1,4-dioxane and the like. They may be used alone or in a mixture of two or more kinds thereof.

A blending amount of the solvent falls in a range of usually 1 to 50 parts by mass, preferably 2 to 25 parts by mass per 1 part by mass of the polymer (6).

Photoacid Generator:

The photoacid generator shall not specifically be restricted, and photoacid generators which have so far usually been used for chemically amplified photoresists can be used. The above photoacid generator includes, for example, nitrobenzyl derivatives such as 2-nitrobenzyl p-toluenesulfonate, 2,6-dinitrobenzyl p-toluenesulfonate, 2,4-dinitrobenzyl p-toluenesulfonate and the like; sulfonic esters such as 1,2,3-tris(methanesulfonyloxy)benzene, 1,2,3-tris(trifluoromethanesulfonyloxy)benzene, 1,2,3-tris(p-toluenesulfonyloxy)benzene and the like; diazomethane derivatives such as bis(benzenesulfonyl)diazomethane, bis(p-toluenesulfonyl)diazomethane, bis(2,4-dimethylphenylsulfonyl)diazomethane, bis(1,1-dimethylethysulfonyl)diazomethane, bis(cyclohexysulfonyl)diazomethane, bis(n-butylsulfonyl)diazomethane and the like; onium salts such as triphenylsulfonium trifluoromethanesulfonate, triphenylsulfonium nonafluoro-n-butanesulfonate, (p-tert-butoxyphenyl)diphenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, tris(p-tert-butoxyphenyl)sulfonium p-toluenesulfonate, trinaphthylsulfonium trifluoromethanesulfonate, cyclohexylmethyl(2-oxocyclohexyl)sulfonium trifluoromethanesulfonate, (2-norbornyl)methyl(2-oxocyclohexyl)sulfonium trifluoromethanesulfonate, 1,2'-naphthylcarbonylmethyltetrahydrothiophenium triflate and the like; glyoxime derivatives such as bis-O-(p-toluenesulfonyl)-α-dimethyl glyoxime, bis-O-(n-butanesulfonyl)-α-dimethyl glyoxime and the like; sulfonic ester derivatives of N-hydroxyimide such as N-hydroxysuccinimidemethanesulfonic ester, N-hydroxysuccinimidetrifluoromethanesulfonic ester, N-hydroxysuccinimide-1-propanesulfonic ester, N-hydroxyimide-p- toluenesulfonic ester, N-hydroxynaphthalimidemethanesulfonic ester, N-hydroxynaphthalimidebenzenesulfonic ester and the like; and halogen-containing triazines such as 2-(4-methoxyphenyl)-4,6-bis(trichloromethyl)-1,3,5-triazine, 2-(4-methoxynaphthyl)-4,6-bis(trichloromethyl)-1,3,5-triazine, 2-[2-(2-furyl)ethenyl)-4,6-bis(trichloromethyl)-1,3,5-triazine, 2-[2-(5-methyl-2-furyl)ethenyl]-4,6-bis(trichloromethyl)-1,3,5-triazine, 2-[2-(3,5-dimethoxyphenyl)ethenyl)-4,6-bis(trichloromethyl)-1,3,5-triazine and the like. They may be used alone or in a mixture of two or more kinds thereof.

A blending amount of the photoacid generator falls usually in a range of preferably 0.1 to 30 parts by mass, more preferably 0.5 to 10 parts by mass per 100 parts by mass of the polymer (6) described above from the viewpoint of securing a sensitivity and a development of the photoresist composition.

Basic Compound:

The photoresist composition can be blended, if necessary, with a basic compound in an amount of a range in which the characteristics of the photoresist composition of the present invention are not inhibited in order to inhibit a diffusion rate of acid in the photoresist film to enhance a resolution thereof.

The above basic compound includes, for example, amides such as formamide, N-methylformamide, N,N-dimethylformamide, acetamide, N-methylacetamide, N,N-dimethylacetamide, N-(1-adamantyl)acetamide, benzamide, N-acetylethanolamine, 1-acetyl-3-methylpiperidine, pyrrolidone, N-methylpyrrolidone, ϵ-caprolactam, δ-valerolactam, 2-pyrrolidinone, acrylamide, methacrylamide, t-butylacrylamide, methylenebisacrylamide, methylenebismethacrylamide, N-methylolacrylamide, N-methoxyacrylamide, diacetoneacrylamide and the like; and amines such as pyridine, 2-methylpyridine, 4-methylpyridine, nicotine, quinoline, acridine, imidazole, 4-methylimidazole, benzimidazole, pyrazine, pyrazole, pyrrolidine, N-t-butoxycarbonylpyrrolidine, piperidine, tetrazole, morpholine, 4-methylmorpholine, piperazine, 1,4-diazabicyclo[2.2.2]octane, tributylamine, tripentylamine, trihexylamine, triheptylamine, trioctylamine, triethanolamine and the like. They may be used alone or in a mixture of two or more kinds thereof.

When the basic compound is blended, a blending amount thereof is varied depending on the kind of the basic compound used and falls usually in a range of preferably 0.01 to 10 mole, more preferably 0.05 to 1 mole per 1 mole of the photoacid generator.

Surfactant:

The photoresist composition of the present invention can be further blended, if desired, with a surfactant in an amount of a range in which the characteristics of the photoresist composition of the present invention are not inhibited in order to enhance a coating property.

The above surfactant includes, for example, polyoxyethylene lauryl ether, polyoxyethylene stearyl ether, polyoxyethylene oleyl ether, polyoxyethylene n-octylphenyl ether and the like. They may be used alone or in a mixture of two or more kinds thereof.

When the surfactant is blended, a blending amount thereof is usually 2 parts by mass or less per 100 parts by mass of the polymer (6).

Other Additives:

Further, the photoresist composition of the present invention can be blended with a sensitizer, a halation inhibitor, a form-improving agent, a storage stabilizer, a defoaming agent and the like as other additives in an amount of a range in which the characteristics of the photoresist composition of the present invention are not inhibited.

Forming Method for Photoresist Pattern:

A method for forming photoresist patterns includes a step in which the photoresist composition described above is used to form a resist film on a support, a step in which the resist film described above is exposed and a step in which the resist film is developed to form a resist pattern.

The resist pattern can be formed, for example, in the following manner.

That is, the photoresist composition described above is first coated on a support by means of a spinner and pre-baked for 1 to 10 minutes on a temperature condition of 70 to 160° C., and the film is exposed selectively to an ArF excimer laser beam via a prescribed mask pattern by means of an ArF exposing equipment and then subjected to post exposure baking for 1 to 5 minutes on a temperature condition of 70 to 160° C. Then, this is subjected to developing treatment using an alkali developer, for example, a 0.1 to 10 mass % tetramethylammonium hydroxide aqueous solution, and it is rinsed preferably in purified water and dried, whereby a resist pattern can be formed.

An organic or inorganic antireflective coat can be provided between a substrate and a coated layer of the photoresist composition.

A wavelength used for exposure shall not specifically be restricted, and the exposure can be carried out by using a radiation such as, for example, an ArF excimer laser, a KrF excimer laser, a $F_2$ excimer laser, EUV (an extreme UV ray), VUV (a vacuum UV ray), EB (an electron beam), an X ray, a soft X ray and the like. The photoresist composition of the present invention is effective particularly to an ArF excimer laser. The exposure dose falls preferably in a range of 0.1 to 1,000 $mJ/cm^2$.

Liquid Immersion Lithography:

The photoresist composition comprising the polymer containing the (meth)acrylic ester derivative (1) of the present invention can be applied as well to liquid immersion lithography. The liquid immersion lithography is an exposing technique in which a liquid having a higher refractive index of light than that of the air is injected between a projector lens of an exposing equipment and a resist film to thereby enhance a resolution. In an ArF liquid immersion lithography, purified water is used as the above liquid. To be specific, when exposed with an ArF excimer laser having a wavelength of 193 nm, purified water is injected between a resist film after pre-baked and a projector lens to carry out the exposure, whereby a radiation passing through the resist film is shifted to a shorter wavelength of 135 nm, and therefore the high resolution can be obtained.

EXAMPLES

The present invention shall be explained in further details with reference to examples, but the present invention shall by no means be restricted by these examples. The measuring methods of Mw and Mn and a calculating method of the dispersion degree in the respective examples are shown below.

Measurement of Mw and Mn and Calculation of Dispersion Degree:

The weight average molecular weight (Mw) and the number average molecular weight (Mn) were measured on the following conditions by gel permeation chromatography (GPC) using tetrahydrofuran (THF) as an eluant by means of a differential refractometer used as a detector, and they were determined as values converted according to a calibration curve prepared using standard polystyrene. Further, the dispersion degree (Mw/Mn) was determined by dividing the weight average molecular weight (Mw) by the number average molecular weight (Mn).

GPC Measurement:

Used was a column obtained by connecting serially two columns of TSK-gel SUPER HZM-H (trade name, 4.6 mm×150 mm, manufactured by Tosoh Corp.) and one column of TSK-gel SUPER HZ2000 (trade name, 4.6 mm×150 mm, manufactured by Tosoh Corp.), and measurement was carried out on the conditions of a column temperature of 40° C., a differential refractometer temperature of 40° C. and a flow velocity of 0.35 mL/minute in the eluant.

Synthetic Example 1

Synthesis of 1,4-dithiane-2-ol

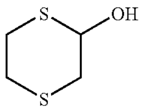

A four neck flask having a content volume of 500 mL equipped with a thermometer, a dropping funnel and a stirring device was charged with 169.3 g (1.36 mol) of chloroacetaldehyde=dimethyl=acetal and 139.3 g (1.37 mol) of acetic anhydride. The flask was cooled on a water bath, and 0.27 g of cone, sulfuric acid was slowly dropwise added thereto while stirring. The mixture was stirred at an inside temperature falling in a range of 20 to 30° C. for 50 hours and then stirred for 3 hours while heating at 50° C.

An inside temperature of the reaction solution was lowered down to room temperature, and then it was transferred into a separating funnel of 1 L. Diisopropyl ether 147.8 g was put thereunto to wash the solution twice with 59.0 g of a 7% sodium hydrogencarbonate aqueous solution, and the solvent was removed by distillation under reduced pressure to obtain 221.8 g of a crude for distillation. A molecular distillation equipment "MS-300" (manufactured by SHIBATA SCIENTIFIC TECHNOLOGY LTD.) was used for the distillation. The above crude was allowed to flow there through at a pressure of 1330 Pa and a temperature of 30° C. to obtain 188.5 g of a high boiling fraction. The above high boiling fraction was allowed to flow there through at a pressure of 1330 Pa and a temperature of 40 to 50° C. to obtain 163.5 g (1.01 mol) of 2-chloral-1-methoxyethyl=acetate showing the following physical properties as a low boiling fraction in the form of a colorless and transparent oil (purity: 94.0%, yield: 74%).

Next, a four neck flask having a content volume of 3 L equipped with a thermometer, a dropping funnel and a stirring device was charged with 1390 g of 1,2-dimethoxyethane, and an inside of the flask was substituted with nitrogen. The flask was charged with 79.0 g (1.96 mol) of sodium hydride (60%) while cooling it on a water bath, and the mixture was stirred for 30 minutes. After the flask was equipped with a reflux condenser, 181.2 g (1.92 mol) of 1,2-ethanedithiol was slowly dropwise added thereto from the dropping funnel so that the temperature was maintained in a range of 25 to 30° C.

After stirring for about 30 minutes since finishing dropwise adding, 154.3 g (0.96 mol) of 2-chloral-1-methoxyethyl=acetate was slowly dropwise added thereto from the dropping funnel so that the temperature was maintained in a range of 25 to 30° C. After finishing dropwise adding, stirring was continued at 25 to 35° C. for 3 hour. In this connection, the reaction solution was analyzed by gas chromatography to find that a conversion rate of 2-chloral-1-methoxyethyl=acetate was 99.2%.

Water 906.5 g was slowly dropwise added from the dropping funnel at a temperature falling in a range of 25 to 60° C., and after finishing dropwise adding, stirring was continued for 12 hours while maintaining the temperature at 60° C. by heating the water bath. In this connection, the reaction solution was analyzed by gas chromatography to find that a ratio of 1,4-dithiane-2-ol to 1,4-dithiane-2-yl=acetate was 1,4-dithiane-2-ol:1,4-dithiane-2-yl=acetate=85:15 (area ratio).

A 10% hydrochloric acid aqueous solution was dropwise added from the dropping funnel at a temperature falling in a range of 10 to 15° C. to adjust the pH to 8.1 (added amount: 112.6 g). The solution obtained was transferred into a separating funnel having a content volume of 5 L and extracted twice with 1670 g of diisopropyl ether. All of the extracts thus obtained was put into a separating funnel having a content volume of 5 L and washed in order with 801 g of water and 504 g of a saturated brain, and the solvent was removed by distillation under reduced pressure to obtain 285.9 g of the concentrate. Diisopropyl ether 47.5 g, n-hexane 85.2 g and a small amount of a crystal seed were added to the concentrate thus obtained, and the mixture was slowly cooled down to 0° C. The deposit was separated by filtering and transferred into a flask of 300 mL, and 320 g of n-hexane was added thereto. The mixture was stirred at 25° C. for 1 hour. The above deposit was separated again by filtering and dried at room temperature under reduced pressure to obtain 73.8 g (0.52 mol) of 1,4-dithiane-2-ol showing the following physical properties in the form of a white solid (purity: 94.1%, yield: 53%).

$^1$H-NMR (300 MHz, $CDCl_3$, TMS, ppm) δ: 2.52 to 2.62 (3H, m), 2.85 (1H, dd, J=2.1, 13.4 Hz), 3.52 to 3.64 (1H, br), 3.86 (1H, ddd, J=5.0, 5.2, 12.1 Hz), 4.28 (1H, ddd, J=4.8, 4.9, 12.1 Hz), 5.03 (1H, ddd, J=1.9, 5.8, 7.7 Hz).

Synthetic Example 2

Synthesis of 1,4-oxathiane-2-ol

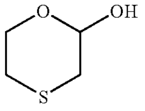

A four neck flask having a content volume of 2 L equipped with a thermometer, a stirring device and a reflux condenser was charged with 691 g of methanol. The flask was cooled on an ice bath, and 128.1 g (3.20 mol) of sodium hydroxide was added thereto little by little while stirring so that the temperature did not exceed 50° C. After finishing addition of sodium hydroxide, stirring was continued, and when the temperature was 2 to 5° C., 250.3 g (3.20 mol) of mercaptoethanol was slowly added thereto from a dropping funnel so that the temperature was controlled in a range of 5 to 10° C. After finishing dropwise adding, stirring was continued for one hour, and 295.6 g (2.37 mol) of chloroacetaldehyde=dimethyl=acetal was dropwise added from a dropping funnel at a temperature falling in a range of 5 to 10° C. After finishing dropwise adding, heating was started, and the solution was stirred for 14 hours at a temperature falling in a range of 70 to 75° C. In this connection, the reaction solution was analyzed by gas chromatography to find that a conversion rate of chloroacetaldehyde=dimethyl=acetal was 95.5%.

After a temperature of the reaction solution was lowered down to room temperature, the reaction solution was filtrated to remove salts produced, and the filtrate was concentrated under reduced pressure and subjected to simple distillation. (2-Hydroxyethylthio)acetaldehyde=dimethyl=acetal 334.0 g (1.89 mol) was obtained in the form of a pale yellow transparent oil on the conditions of a pressure of 545 Pa, a vessel inside temperature of 146° C. and a distillation temperature of 122° C. (purity: 94.3%, yield: 80%).

Next, a four neck flask having a content volume of 1 L equipped with a thermometer, a distilling head and a stirring device was charged with 672.3 g of water, 100 g (565 mol) of (2-hydroxyethylthio)acetaldehyde=dimethyl=acetal and 1.67 g of a 5.0 mass % sulfuric acid aqueous solution. The mixture was stirred for 4 hours on the conditions of a pressure of 16.0 kPa and a vessel inside temperature of 70° C. while removing water and resulting methanol by distillation. In this connection, the solution was analyzed by gas chromatography to find that a conversion rate of (2-hydroxyethylthio) acetaldehyde=dimethyl=acetal was 94.2%.

After the vessel inside temperature was lowered down to room temperature, the pH was adjusted to 8.0 by a 4.0 mass % sodium hydroxide aqueous solution, and the solution was extracted three times with 400 g of ethyl acetate. All of the extracts obtained were put together and concentrated under reduced pressure to obtain 63.3 g of the concentrate. The above concentrate was dissolved in 158 g of diisopropyl ether, and the solution was slowly cooled down to 8° C., followed by separating a white crystal deposited by filtering, whereby 35.1 g (287 mol) of 1,4-oxathiane-2-ol was obtained in the form of a white crystal (purity: 98.2%, yield: 51%).

Synthetic Example 3

Synthesis of 1,4-dioxane-2-ol

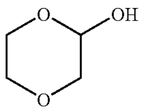

A four neck flask having a content volume of 1 L equipped with a thermometer, a stirring device and a reflux condenser was charged with 350.0 g (5.64 mol) of 1,2-ethanediol. The flask was cooled on an ice bath, and 237.0 g (4.23 mol) of potassium hydroxide was added thereto little by little while stirring so that the temperature did not exceed 50° C.

After finishing addition of potassium hydroxide, 351.2 g (2.82 mol) of chloroacetaldehyde=dimethyl=acetal was dropwise added thereto at a temperature falling in a range of 40 to 50° C. After finishing dropwise adding, heating was started, and stirring was continued for 22 hours at a temperature falling in a range of 110 to 112° C. In this connection, the reaction solution was analyzed by gas chromatography to find that a conversion rate of chloroacetaldehyde=dimethyl==acetal was 78.6%.

After a temperature of the reaction solution was lowered down to room temperature, the reaction solution was filtrated to remove salts produced, and the filtrate was subjected to simple distillation. A transparent oil was obtained on the conditions of a pressure of 533 to 933 Pa, a vessel inside temperature of 105 to 119° C. and a distillation temperature of 96 to 102° C. The above oil was analyzed by gas chromatography to find that a purity of 2-(2,2-dimethoxyethyloxy)ethanol was 50.0%. Next, the oil obtained was distilled by means of a distillation column filled with packing McMahon. 2-(2,2-Dimethoxyethyloxy)ethanol 101.8 g was obtained in the form of a colorless and transparent oil on the conditions of a pressure of 133 to 493 Pa, a vessel inside temperature of 113 to 137° C. and a distillation temperature of 82.5 to 87.0° C. (purity: 97.5%, yield: 23.5% based onchloroacetaldehyde=dimethyl=acetal).

Next, a four neck flask having a content volume of 200 mL equipped with a thermometer, a distilling head and a stirring device was charged with 137.4 g of water, 42.2 mg of sulfuric acid and 20.0 g (130 mol) of 2-(2,2-dimethoxyethyloxy)ethanol. The mixture was stirred for 11 hours on the conditions of a pressure of 18.0 kPa and a vessel inside temperature of 60° C. while removing water and resulting methanol by distillation. In this connection, the reaction solution was analyzed by gas chromatography to find that a conversion rate of 2-(2,2-dimethoxyethyloxy)ethanol was 99.6%.

After the vessel inside temperature was lowered down to room temperature, the pH was adjusted to 8.3 by a 10.0 mass % sodium hydroxide aqueous solution, and the reaction solution was extracted three times with 300 g of ethyl acetate. All of the extracts obtained were put together and concentrated under reduced pressure, and 17.41 g of the concentrate obtained was subjected to simple distillation. 1,4-Dioxane-2-ol 8.50 g (75.6 mol) was obtained in the form of a colorless and transparent oil on the conditions of a pressure of 1.60 kPa, a vessel inside temperature of 97 to 115° C. and a distillation temperature of 92 to 96° C. (purity: 92.5%, yield: 58.1% based on 2-(2,2-dimethoxyethyloxy)ethanol).

Synthetic Example 4

Production of 1,4-dithiepane-2-ol

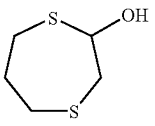

A four neck flask of 3 L equipped with a thermometer, a dropping funnel and a stirring device was charged with 1390 g of 1,2-dimethoxyethane, and an inside of the flask was substituted with nitrogen. The flask was charged with 79.0 g (1.96 mol) of sodium hydride (60%) while cooling it on a water bath, and the mixture was stirred for 30 minutes. The flask was equipped with a reflux condenser, and then 209.9 g (1.92 mol) of 1,3-propanedithiol was slowly dropwise added thereto from the dropping funnel so that the temperature was maintained in a range of 25 to 30° C.

After stirring for 30 minutes since finishing dropwise adding, 154.3 g (0.96 mol) of 2-chloral-1-methoxyethyl-acetate was slowly dropwise added thereto from the dropping funnel so that the temperature was maintained in a range of 25 to 30° C. After finishing dropwise adding, stirring was continued at 25 to 35° C. for 5 hours. In this connection, the reaction solution was analyzed by gas chromatography to find that a conversion rate of 2-chloral-1-methoxyethyl=acetate was 98.9%. Water 906.0 g was slowly dropwise added from the dropping funnel at a temperature falling in a range of 25 to 60° C., and after finishing dropwise adding, stirring was continued for 12 hours while maintaining the temperature at 60° C. by heating the water bath. In this connection, the reaction solution was analyzed by gas chromatography to find that a ratio of 1,4-dithiepane-2-ol to 1,4-dithiepane-2-yl=acetate was 1,4-dithiepane-2-ol:1,4-dithiepane-2-yl=acetate=82:18 (area ratio).

A 10% hydrochloric acid aqueous solution was dropwise added from the dropping funnel at a temperature falling in a range of 10 to 15° C. to adjust the pH to 8.2. The solution obtained was transferred into a separating funnel having a content volume of 5 L and extracted twice with 1650 g of diisopropyl ether. All of the extracts thus obtained were put into a separating funnel having a content volume of 5 L and washed in order with 800 g of water and 500 g of a saturated brain, and the solvent was removed by distillation under reduced pressure. The concentrate was refined by silica gel chromatography to thereby obtain 40.8 g (0.26 mol) of 1,4-dithiepane-2-ol (purity: 97.1%, yield: 27.5%).

Synthetic Example 5

Synthesis of 1,4-oxathiepane-2-ol

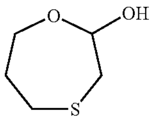

A four neck flask having a content volume of 500 mL equipped with a thermometer, a stirring device and a reflux condenser was charged with 138 g of methanol. The flask was cooled on an ice bath, and 20.6 g (515 mol) of sodium hydroxide was added thereto little by little while stirring so that the temperature did not exceed 50° C. After finishing addition of sodium hydroxide, stirring was continued, and when the temperature was 2 to 5° C., 50.0 g (515 mol) of 3-mercapto-1-propanol was slowly added thereto from a dropping funnel so that the temperature was controlled in a range of 5 to 10° C. After finishing dropwise adding, stirring was continued for one hour, and 47.5 g (381 mol) of chloroacetaldehyde=dimethyl=acetal was dropwise added from a dropping funnel at a temperature falling in a range of 5 to 10° C. After finishing dropwise adding, heating was started, and stirring was continued for 15 hours at a temperature falling in a range of 75 to 80° C. In this connection, the reaction solution was analyzed by gas chromatography to find that a conversion rate of chloroacetaldehyde=dimethyl=acetal was 92.0%.

After a temperature of the reaction solution was lowered down to room temperature, the reaction solution was filtrated to remove salts produced, and the filtrate was concentrated under reduced pressure and subjected to simple distillation to obtain 55.3 g of 3-(2,2-dimethoxyethylthio)-1-propanol in the form of a pale yellow transparent oil (purity: 94.2%, yield: 75.9% based on chloroacetaldehyde=dimethyl=acetal).

Next, a four neck flask having a content volume of 200 mL equipped with a thermometer, a distilling head and a stirring device was charged with 137.4 g of water, 42.2 mg of sulfuric acid and 24.9 g (130 mol) of 3-(2,2-dimethoxyethylthio)-1-propanol. The mixture was stirred for 11 hours on the conditions of a pressure of 18.0 kPa and a vessel inside temperature of 60° C. while removing water and resulting methanol by distillation. In this connection, the reaction solution was analyzed by gas chromatography to find that a conversion rate of 3-(2,2-dimethoxyethylthio)-1-propanol was 99.6%.

After the vessel inside temperature was lowered down to room temperature, the pH was adjusted to 8.0 by a 10.0 mass % sodium hydroxide aqueous solution, and the reaction solution was extracted three times with 300 g of ethyl acetate. All of the extracts obtained were put together and concentrated under reduced pressure, and the concentrate obtained was refined by silica gel chromatography to obtain 5.90 g (43.8 mol) of 1,4-oxathiepane-2-ol (purity: 98.5%, yield: 33.3% based on 3-(2,2-dimethoxyethylthio)-1-propanol).

Synthetic Example 6

Synthesis of 1,4-dioxepane-2-ol

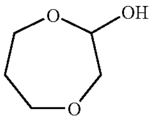

A four neck flask having a content volume of 2 L equipped with a thermometer, a stirring device and a reflux condenser was charged with 429.1 g (5.64 mol) of 1,3-propanediol. The flask was cooled on an ice bath, and 237.0 g (4.23 mol) of potassium hydroxide was added thereto little by little while stirring so that the temperature did not exceed 50° C. After finishing addition of potassium hydroxide, 351.2 g (2.82 mol) of chloroacetaldehyde=dimethyl=acetal was dropwise added at a temperature falling in a range of 40 to 50° C. After finishing dropwise adding, heating was started, and stirring was continued for 22 hours at a temperature falling in a range of 110 to 112° C. In this connection, the reaction solution was analyzed by gas chromatography to find that a conversion rate of chloroacetaldehyde=dimethyl=acetal was 69.2%.

After a temperature of the reaction solution was lowered down to room temperature, the reaction solution was filtrated to remove salts produced, and the filtrate was distilled to obtain 103.3 g of 3-(2,2-dimethoxyethyloxy)-1-propanol in the form of a colorless and transparent oil (purity: 97.0%, yield: 21.6% based on chloroacetaldehyde=dimethyl=acetal).

Next, a four neck flask having a content volume of 200 mL equipped with a thermometer, a distilling head and a stirring device was charged with 137.4 g of water, 42.2 mg of sulfuric acid and 22.0 g (130 mol) of 3-(2,2-dimethoxyethyloxy)-1-propanol. The mixture was stirred for 11 hours on the conditions of a pressure of 18.0 kPa and a vessel inside temperature of 60° C. while removing water and resulting methanol by distillation. In this connection, the reaction solution was analyzed by gas chromatography to find that a conversion rate of 3-(2,2-dimethoxyethyloxy)-1-propanol was 99.6%. After the vessel inside temperature was lowered down to room temperature, the pH was adjusted to 8.3 by a 10.0 mass % sodium hydroxide aqueous solution, and the reaction solution was extracted three times with 300 g of ethyl acetate. All of the extracts obtained were put together and concentrated under reduced pressure, and the concentrate obtained was refined by silica gel chromatography to obtain 5.40 g (44.7 mol) of 1,4-dioxepane-2-ol (purity: 97.9%, yield: 34.4% based on 3-(2,2-dimethoxyethyloxy)-1-propanol).

Synthetic Example 7

Production of 5,6-dimethyl-1,4-dithiane-2-ol

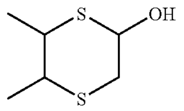

A four neck flask having a content volume of 300 mL equipped with a thermometer, a dropping funnel and a stirring device was charged with 139 g of 1,2-dimethoxyethane, and an inside of the flask was substituted with nitrogen. The flask was charged with 7.90 g (197 mol) of sodium hydride (60%) while cooling it on a water bath, and the mixture was stirred for 30 minutes. The flask was equipped with a reflux condenser, and then 24.2 g (192 mol) of 2,3-butanedithiol was slowly dropwise added thereto from the dropping funnel so that the temperature was maintained in a range of 25 to 30° C.

After stirring for 30 minutes since finishing dropwise adding, 15.4 g (94.9 mol) of 2-chloral-1-methoxyethyl=acetate was slowly dropwise added thereto from the dropping funnel so that the temperature was maintained in a range of 25 to 30° C. After finishing dropwise adding, stirring was continued at 25 to 35° C. for 5 hours. In this connection, the reaction solution was analyzed by gas chromatography to find that a conversion rate of 2-chloral-1-methoxyethyl=acetate was 98.9%.

Water 90.0 g was slowly dropwise added from the dropping funnel at a temperature falling in a range of 25 to 60° C., and after finishing dropwise adding, stirring was continued for 12 hours while maintaining the temperature at 60° C. by heating the water bath. In this connection, the reaction solution was analyzed by gas chromatography to find that a ratio of 5,6-dimethyl-1,4-dithiane-2-ol to 5,6-dimethyl-1,4-dithiane-2-yl=acetate was 5,6-dimethyl-1,4-dithiane-2-ol:5,6-dimethyl-1,4-dithiane-2-yl=acetate=88:12 (area ratio).

A 10% hydrochloric acid aqueous solution was dropwise added from the dropping funnel at a temperature falling in a range of 10 to 15° C. to adjust the pH to 8.2. The solution obtained was transferred into a separating funnel having a content volume of 500 mL and extracted twice with 160 g of diisopropyl ether. All of the extracts thus obtained were put into a separating funnel having a content volume of 500 mL and washed in order with 10 g of water and 20 g of a saturated brain, and the solvent was removed by distillation under reduced pressure. The concentrate was refined by silica gel chromatography to thereby obtain 9.09 g (54.1 mol) of 5,6-dimethyl-1,4-dithiane-2-ol (purity: 97.8%, yield: 57.0%).

Synthetic Example 8

Synthesis of 6-methyl-1,4-oxathiane-2-ol

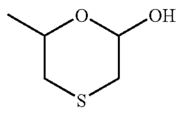

A four neck flask having a content volume of 500 mL equipped with a thermometer, a stirring device and a reflux condenser was charged with 138 g of methanol. The flask was cooled on an ice bath, and 20.6 g (515 mol) of sodium hydroxide was added thereto little by little while stirring so that the temperature did not exceed 50° C. After finishing addition of sodium hydroxide, stirring was continued, and when the temperature was 2 to 5° C., 50.0 g (515 mol) of 1-mercapto-2-propanol was slowly added thereto from a dropping funnel so that the temperature was controlled in a range of 5 to 10° C.

After finishing dropwise adding, stirring was continued for one hour, and 47.5 g (381 mol) of chloroacetaldehyde=dimethyl=acetal was dropwise added from a dropping funnel at a temperature falling in a range of 5 to 10° C. After finishing dropwise adding, heating was started, and stirring was continued for 15 hours at a temperature falling in a range of 75 to 80° C. In this connection, the reaction solution was analyzed by gas chromatography to find that a conversion rate of chloroacetaldehyde=dimethyl=acetal was 90.9%.

After a temperature of the reaction solution was lowered down to room temperature, the reaction solution was filtrated to remove salts produced, and the filtrate was concentrated under reduced pressure and subjected to simple distillation to obtain 51.1 g of 1-(2,2-dimethoxyethylthio)-2-propanol in the form of a pale yellow transparent oil (purity: 92.9%, yield: 69.1% based on chloroacetaldehyde=dimethyl=acetal).

Next, a four neck flask having a content volume of 200 mL equipped with a thermometer, a distilling head and a stirring device was charged with 137.4 g of water, 42.2 mg of sulfuric acid and 25.2 g (130 mol) of 1-(2,2-dimethoxyethylthio)-2-propanol. The mixture was stirred for 11 hours on the conditions of a pressure of 18.0 kPa and a vessel inside temperature of 60° C. while removing water and resulting methanol by distillation. In this connection, the reaction solution was analyzed by gas chromatography to find that a conversion rate of 1-(2,2-dimethoxyethylthio)-2-propanol was 99.6%.

After the vessel inside temperature was lowered down to room temperature, the pH was adjusted to 8.1 by a 10.0 mass % sodium hydroxide aqueous solution, and the reaction solution was extracted three times with 300 g of ethyl acetate. All of the extracts obtained were put together and concentrated under reduced pressure, and the concentrate obtained was refined by silica gel chromatography to obtain 11.2 g (82.6 mol) of 6-methyl-1,4-oxathiane-2-ol (purity: 99.0%, yield: 63.6% based on 1-(2,2-dimethoxyethylthio)-2-propanol).

Synthetic Example 9

Synthesis of 5,6-dimethyl-1,4-dioxane-2-ol

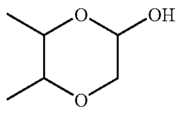

A four neck flask having a content volume of 2 L equipped with a thermometer, a stirring device and a reflux condenser was charged with 518.6 g (5.64 mol) of 2,3-butanediol. The flask was cooled on an ice bath, and 237.0 g (4.23 mol) of potassium hydroxide was added thereto little by little while stirring so that the temperature did not exceed 50° C. After finishing addition of potassium hydroxide, 351.2 g (2.82 mol) of chloroacetaldehyde=dimethyl=acetal was dropwise added at a temperature falling in a range of 40 to 50° C. After finishing dropwise adding, heating was started, and stirring was continued for 22 hours at a temperature falling in a range of 110 to 112° C. In this connection, the reaction solution was analyzed by gas chromatography to find that a conversion rate of chloroacetaldehyde=dimethyl=acetal was 57.9%.

After a temperature of the reaction solution was lowered down to room temperature, the reaction solution was filtrated to remove salts produced, and the filtrate was distilled to obtain 94.4 g of 3-(2,2-dimethoxyethyloxy)-2-butanol in the form of a colorless and transparent oil (purity: 95.9%, yield: 18.0% based on chloroacetaldehyde=dimethyl=acetal).

Next, a four neck flask having a content volume of 200 mL equipped with a thermometer, a distilling head and a stirring device was charged with 137.4 g of water, 42.2 mg of sulfuric acid and 24.2 g (130 mol) of 3-(2,2-dimethoxyethyloxy)-2-butanol. The mixture was stirred for 11 hours on the conditions of a pressure of 18.0 kPa and a vessel inside temperature of 60° C. while removing water and resulting methanol by distillation. In this connection, the reaction solution was analyzed by gas chromatography to find that a conversion rate of 3-(2,2-dimethoxyethyloxy)-2-butanol was 99.6%.

After the vessel inside temperature was lowered down to room temperature, the pH was adjusted to 8.0 by a 10.0 mass % sodium hydroxide aqueous solution, and the reaction solution was extracted three times with 300 g of ethyl acetate. All of the extracts obtained were put together and concentrated under reduced pressure, and the concentrate obtained was refined by silica gel chromatography to obtain 9.66 g (72.2 mol) of 5,6-dimethyl-1,4-dioxane-2-ol in the form of a colorless and transparent oil (purity: 98.8%, yield: 55.5% based on 3-(2,2-dimethoxyethyloxy)-2-butanol).

Example 1

Production of 1,4-dithiane-2-yl=chloroacetate

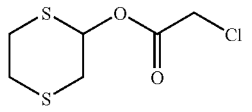 [SMILES: O=C(CCl)OC1CSCCS1]

A three neck flask having a content volume of 50 mL equipped with a thermometer, a dropping funnel and a stirring device was charged with 0.68 g (5 mol) of 1,4-dithiane-2-ol obtained in Synthetic Example 1 and 5 g of tetrahydrofuran and subsequently charged with 0.48 g (6 mol) of pyridine, and the mixture was stirred at room temperature for 30 minutes. Then, 0.64 g (97%, 5.5 mol) of chloroacetyl chloride was dropwise added thereto while stirring at room temperature, and the reaction mixture was stirred at room temperature for 4 hours. Distilled water 3.5 g was added to the reaction mixture to separate it into an organic layer and an aqueous layer, and the organic layer was concentrated. Toluene 10 g and water 5 g were added to the concentrated residue and stirred, and then it was separated into an organic layer and an aqueous layer. The organic layer was washed with 5 g of a 8% sodium hydrogencarbonate aqueous solution and then with 6 g of distilled water, and then it was concentrated to obtain 0.89 g (3.9 mol) of crude 1,4-dithiane-2-yl=chloroacetate (yield: 77.8%).

$^1$H-NMR (300 MHz, $CDCl_3$, TMS, ppm) δ: 5.89 (1H, t), 4.18 (2H, s), 3.35 (2H, m), 3.07 (1H, m), 2.92 (1H, m), 2.73 (2H, m)

Example 2

Production of 2-(1,4-dithiane-2-yloxy)-2-oxoethyl=methacrylate

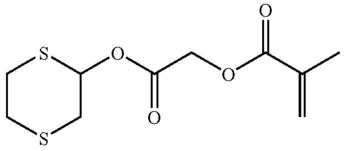 [SMILES: C=C(C)C(=O)OCC(=O)OC1CSCCS1]

A three neck flask having a content volume of 50 mL equipped with a thermometer, a dropping funnel and a stirring device was charged with 12.5 mg of p-methoxyphenol, 0.45 g (3.3 mol) of potassium carbonate, 5.0 g of toluene and 0.41 g (4.8 mol) of methacrylic acid, and the mixture was stirred at room temperature for one hour. Then, a solution prepared by dissolving 0.88 g (3.8 mol) of 1,4-dithiane-2-yl=chloroacetate obtained in Example 1 in 7 g of toluene was added thereto while stirring at room temperature, and 18.5 mg (0.05 mol) of tetrabutylammonium iodide was added thereto, followed by heating the mixture up to 80° C. The reaction mixture was stirred at an inside temperature of 80° C. for 3 hours and then cooled down to room temperature. Distilled water 10 g was added to the reaction mixture and stirred, and then it was separated into an organic layer and an aqueous layer, followed by washing the organic layer with 10 g of distilled water. The organic layer was concentrated, and the residue obtained was refined by silica gel chromatography (eluant: n-hexane/ethyl acetate=3/1) to obtain 0.90 g (3.4 mol) of 2-(1,4-dithiane-2-yloxy)-2-oxoethyl=methacrylate (yield: 89.5%).

$^1$H-NMR (300 MHz, $CDCl_3$, TMS, ppm) δ: 6.25 (1H, s), 5.89 (1H, t), 5.68 (1H, m), 4.78 (2H, d), 3.32 (2H, m), 3.06 (1H, m), 2.92 (1H, m), 2.71 (2H, m), 2.00 (3H, s).

Example 3

Production of 1,4-oxathiane-2-yl=chloroacetate

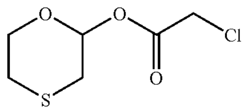 [SMILES: O=C(CCl)OC1CSCCO1]

A three neck flask having a content volume of 50 mL equipped with a thermometer, a dropping funnel and a stirring device was charged with 3.64 g (30 mol) of 1,4-oxathiane-2-ol obtained in Synthetic Example 2 and 15 g of tetrahydrofuran and subsequently charged with 2.85 g (36 mol) of pyridine, and the mixture was stirred at room temperature for 30 minutes. Then, 3.89 g (97%, 33 mol) of chloroacetyl chloride was dropwise added thereto while stirring at room temperature, and the reaction mixture was stirred at room temperature for 5 hours. Distilled water 13 g was added to the reaction mixture to separate it into an organic layer and an aqueous layer, and the organic layer was concentrated. Toluene 15 g and water 10 g were added to the concentrated residue and stirred, and then it was separated into an organic layer and an aqueous layer. The organic layer was washed with 7 g of a 10% sodium carbonate aqueous solution and then two times with 10 g of distilled water, and then it was concentrated to obtain 5.54 g (23.6 mol) of crude 1,4-oxathiane-2-yl=chloroacetate (yield: 78.5%).

$^1$H-NMR (300 MHz, $CDCl_3$, TMS, ppm) δ: 5.98 (1H, m), 4.26 (1H, m), 4.13 (2H, s), 3.95 (1H, m), 2.85 (1H, m), 2.70 (1H, m), 2.60 (2H, m)

Example 4

Production of 2-(1,4-oxathiane-2-yloxy)-2-oxoethyl=methacrylate

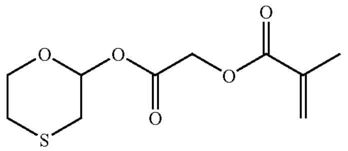 [SMILES: C=C(C)C(=O)OCC(=O)OC1CSCCO1]

A three neck flask having a content volume of 50 mL equipped with a thermometer, a stirring device and a reflux condenser was charged with 33.4 mg of p-methoxyphenol, 2.09 g (15 mol) of potassium carbonate, 20 g of toluene and 1.89 g (22 mol) of methacrylic acid, and the mixture was stirred at room temperature for 30 minutes. Then, a solution prepared by dissolving 4.80 g (20.4 mol) of 1,4-oxathiane-2-yl-chloroacetate obtained in Example 3 in 6 g of toluene was added thereto, and 75.0 mg (0.2 mol) of tetrabutylammonium iodide was added thereto, followed by heating the mixture up to 80° C. The reaction mixture was stirred at an inside temperature of 80° C. for 3 hours and then cooled down to room temperature. Distilled water 20 g was added to the reaction mixture and stirred, and then it was separated into an organic layer and an aqueous layer, followed by washing the organic layer twice with 20 g of distilled water. The organic layer was concentrated, and the residue obtained was refined by silica gel chromatography (eluant: n-hexane/ethyl acetate=3/1) to obtain 4.18 g (17.0 mol) of 2-(1,4-oxathiane-2-yloxy)-2-oxoethyl=methacrylate (yield: 83.3%).

$^1$H-NMR (300 MHz, $CDCl_3$, TMS, ppm) δ: 6.22 (1H, s), 6.01 (1H, m), 5.66 (1H, m), 4.75 (2H, d), 4.24 (1H, m), 3.94 (1H, m), 2.85 (1H, m), 2.68 (1H, m), 2.60 (2H, m), 1.98 (3H, s)

Example 5

Production of 1,4-dioxane-2-yl=chloroacetate

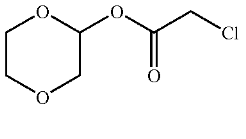 [SMILES: O=C(CCl)OC1COCCO1]

The reaction was carried out in the same charged amounts on the same conditions as in Example 3, except that in Example 3, 3.38 g (30 mol) of 1,4-dioxane-2-ol obtained in Synthetic Example 3 was used in place of 3.64 g (30 mol) of 1,4-oxathiane-2-ol.

Distilled water 13 g was added to the reaction mixture obtained, and it was separated into an organic layer and an aqueous layer. The organic layer was concentrated, and the residue obtained was refined by silica gel chromatography to obtain 4.15 g (22.7 mol) of 1,4-dioxane-2-yl=chloroacetate (yield: 75.7%).

$^1$H-NMR (300 MHz, $CDCl_3$, TMS, ppm) δ: 5.90 to 5.92 (1H, m), 4.07 to 4.21 (3H, m), 3.74 to 3.87 (4H, m), 3.65 (1H, dt, J=11.7, 2.7 Hz)

Example 6

Production of 2-(1,4-dioxane-2-yloxy)-2-oxoethyl=methacrylate

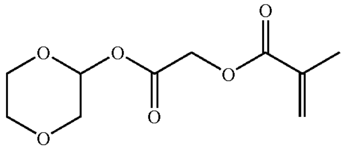 [SMILES: C=C(C)C(=O)OCC(=O)OC1COCCO1]

The reaction was carried out in the same charged amounts on the same conditions as in Example 4, except that in Example 4, 3.73 g (20.4 mol) of 1,4-dioxane-2-yl=chloroacetate obtained in Example 5 was used in place of 4.80 g (20.4 mol) of 1,4-oxathiane-2-yl=chloroacetate.

Distilled water 20 g was added to the reaction mixture obtained and stirred, and then it was separated into an organic layer and an aqueous layer, followed by washing the organic layer twice with 20 g of distilled water. The organic layer was concentrated, and the residue obtained was refined by silica gel chromatography to obtain 4.06 g (17.3 mol) of 2-(1,4-dioxane-2-yloxy)-2-oxoethyl=methacrylate (yield: 84.8%).

$^1$H-NMR (300 MHz, $CDCl_3$, TMS, ppm) δ:6.24 (1H, s), 5.90 to 5.92 (1H, m), 5.65 to 5.68 (1H, m), 4.74 (2H, d), 4.07 to 4.21 (1H, m), 3.74 to 3.87 (4H, m), 3.65 (1H, dt, J=11.7, 2.7 Hz), 1.99 (3H, s)

Example 7

Production of 1,4-dithiepane-2-yl=chloroacetate

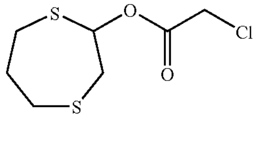 [SMILES: O=C(CCl)OC1CSCCCS1]

The reaction was carried out in the same charged amounts on the same conditions as in Example 3, except that in Example 3, 4.64 g (30 mol) of 1,4-dithiepane-2-ol obtained in Synthetic Example 4 was used in place of 3.64 g (30 mol) of 1,4-oxathiane-2-ol.

Distilled water 13 g was added to the reaction mixture obtained, and it was separated into an organic layer and an aqueous layer. The organic layer was concentrated, and the residue obtained was refined by silica gel chromatography to obtain 5.65 g (24.7 mol) of 1,4-dithiepane-2-yl=chloroacetate (yield: 82.3%).

Example 8

Production of 2-(1,4-dithiepane-2-yloxy)-2-oxoethyl=methacrylate

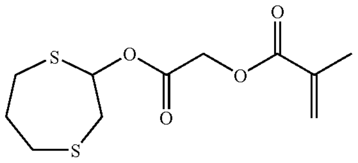 [SMILES: C=C(C)C(=O)OCC(=O)OC1CSCCCS1]

The reaction was carried out in the same charged amounts on the same conditions as in Example 4, except that in Example 4, 4.67 g (20.4 mol) of 1,4-dithiepane-2-yl=chloroacetate obtained in Example 7 was used in place of 4.80 g (20.4 mol) of 1,4-oxathiane-2-yl=chloroacetate.

Distilled water 20 g was added to the reaction mixture obtained and stirred, and then it was separated into an organic layer and an aqueous layer, followed by washing the organic layer twice with 20 g of distilled water. The organic layer was concentrated, and the residue obtained was refined by silica gel chromatography to obtain 4.91 g (17.5 mol) of 2-(1,4-dithiepane-2-yloxy)-2-oxoethyl=methacrylate (yield: 85.8%).

Example 9

Production of 1,4-oxathiepane-2-yl=chloroacetate

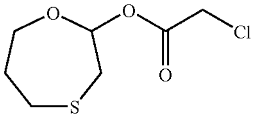 [SMILES: O=C(CCl)OC1CSCCCO1]

The reaction was carried out in the same charged amounts on the same conditions as in Example 3, except that in Example 3, 4.09 g (30 mol) of 1,4-oxathiepane-2-ol obtained in Synthetic Example 5 was used in place of 3.64 g (30 mol) of 1,4-oxathiane-2-ol.

Distilled water 13 g was added to the reaction mixture obtained, and it was separated into an organic layer and an aqueous layer. The organic layer was concentrated, and the residue obtained was refined by silica gel chromatography to obtain 4.98 g (23.1 mol) of 1,4-oxathiepane-2-yl=chloroacetate (yield: 77.0%).

Example 10

Production of 2-(1,4-oxathiepane-2-yloxy)-2-oxoethyl=methacrylate

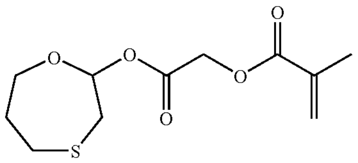 [SMILES: C=C(C)C(=O)OCC(=O)OC1CSCCCO1]

The reaction was carried out in the same charged amounts on the same conditions as in Example 4, except that in Example 4, 4.40 g (20.4 mol) of 1,4-oxathiepane-2-yl=chloroacetate obtained in Example 9 was used in place of 4.80 g (20.4 mol) of 1,4-oxathiane-2-yl=chloroacetate.

Distilled water 20 g was added to the reaction mixture obtained and stirred, and then it was separated into an organic layer and an aqueous layer, followed by washing the organic layer twice with 20 g of distilled water. The organic layer was concentrated, and the residue obtained was refined by silica gel chromatography to obtain 5.01 g (19.0 mol) of 2-(1,4-oxathiepane-2-yloxy)-2-oxoethyl=methacrylate (yield: 93.1%).

Example 11

Production of 1,4-dioxepane-2-yl=chloroacetate

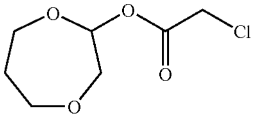 [SMILES: O=C(CCl)OC1COCCCO1]

The reaction was carried out in the same charged amounts on the same conditions as in Example 3, except that in Example 3, 3.62 g (30 mol) of 1,4-dioxepane-2-ol obtained in Synthetic Example 6 was used in place of 3.64 g (30 mol) of 1,4-oxathiane-2-ol.

Distilled water 13 g was added to the reaction mixture obtained, and it was separated into an organic layer and an aqueous layer. The organic layer was concentrated, and the residue obtained was refined by silica gel chromatography to obtain 4.96 g (25.3 mol) of 1,4-dioxepane-2-yl=chloroacetate (yield: 84.3%).

Example 12

Production of 2-(1,4-dioxepane-2-yloxy)-2-oxoethyl=methacrylate

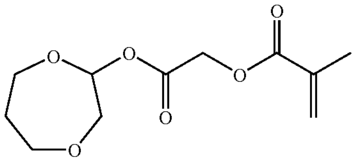 [SMILES: C=C(C)C(=O)OCC(=O)OC1COCCCO1]

The reaction was carried out in the same charged amounts on the same conditions as in Example 4, except that in Example 4, 4.00 g (20.4 mol) of 1,4-dioxepane-2-yl=chloroacetate obtained in Example 11 was used in place of 4.80 g (20.4 mol) of 1,4-oxathiane-2-yl=chloroacetate.

Distilled water 20 g was added to the reaction mixture obtained and stirred, and then it was separated into an organic layer and an aqueous layer, followed by washing the organic layer twice with 20 g of distilled water. The organic layer was concentrated, and the residue obtained was refined by silica gel chromatography to obtain 4.44 g (17.8 mol) of 2-(1,4-dioxepane-2-yloxy)-2-oxoethyl=methacrylate (yield: 87.3%).

Example 13

Production of 5,6-dimethyl-1,4-dithiane-2-yl=chloroacetate

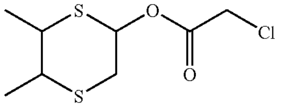

The reaction was carried out in the same charged amounts on the same conditions as in Example 3, except that in Example 3, 5.04 g (30 mol) of 5,6-dimethyl-1,4-dithiane-2-ol obtained in Synthetic Example 7 was used in place of 3.64 g (30 mol) of 1,4-oxathiane-2-ol.

Distilled water 13 g was added to the reaction mixture obtained, and it was separated into an organic layer and an aqueous layer. The organic layer was concentrated, and the residue obtained was refined by silica gel chromatography to obtain 5.55 g (22.8 mol) of 5,6-dimethyl-1,4-dithiane-2-yl=chloroacetate (yield: 76.0%).

Example 14

Production of 2-(5,6-dimethyl-1,4-dithiane-2-yloxy)-2-oxoethyl=methacrylate

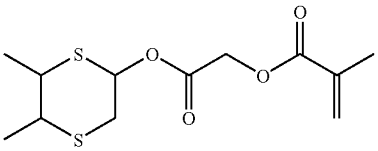 [SMILES: C=C(C)C(=O)OCC(=O)OC1CSC(C)C(C)S1]

The reaction was carried out in the same charged amounts on the same conditions as in Example 4, except that in Example 4, 4.97 g (20.4 mol) of 5,6-dimethyl-1,4-dithiane-2-yl=chloroacetate obtained in Example 13 was used in place of 4.80 g (20.4 mol) of 1,4-oxathiane-2-yl=chloroacetate.

Distilled water 20 g was added to the reaction mixture obtained and stirred, and then it was separated into an organic layer and an aqueous layer, followed by washing the organic layer twice with 20 g of distilled water. The organic layer was concentrated, and the residue obtained was refined by silica gel chromatography to obtain 5.37 g (18.3 mol) of 2-(5,6-dimethyl-1,4-dithiane-2-yloxy)-2-oxoethyl=methacrylate (yield: 89.7%).

Example 15

Production of 6-methyl-1,4-oxathiane-2-yl=chloroacetate

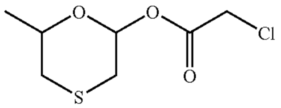

The reaction was carried out in the same charged amounts on the same conditions as in Example 3, except that in Example 3, 5.04 g (30 mol) of 6-methyl-1,4-oxathiane-2-ol obtained in Synthetic Example 8 was used in place of 3.64 g (30 mol) of 1,4-oxathiane-2-ol.

Distilled water 13 g was added to the reaction mixture obtained, and it was separated into an organic layer and an aqueous layer. The organic layer was concentrated, and the residue obtained was refined by silica gel chromatography to obtain 5.52 g (25.7 mol) of 6-methyl-1,4-oxathiane-2-yl=chloroacetate (yield: 85.7%).

Example 16

Production of 2-(6-methyl-1,4-oxathiane-2-yloxy)-2-oxoethyl=methacrylate

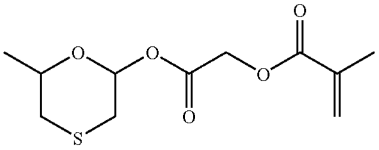 [SMILES: C=C(C)C(=O)OCC(=O)OC1CSCC(C)O1]

The reaction was carried out in the same charged amounts on the same conditions as in Example 4, except that in Example 4, 4.34 g (20.4 mol) of 6-methyl-1,4-oxathiane-2-yl=chloroacetate obtained in Example 15 was used in place of 4.80 g (20.4 mol) of 1,4-oxathiane-2-yl=chloroacetate.

Distilled water 20 g was added to the reaction mixture obtained and stirred, and then it was separated into an organic layer and an aqueous layer, followed by washing the organic layer twice with 20 g of distilled water. The organic layer was concentrated, and the residue obtained was refined by silica gel chromatography to obtain 4.34 g (16.5 mol) of 2-(6-methyl-1,4-oxathiane-2-yloxy)-2-oxoethyl=methacrylate (yield: 80.9%).

Example 17

Production of 5,6-dimethyl-1,4-dioxane-2-yl=chloroacetate

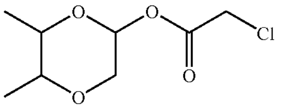

The reaction was carried out in the same charged amounts on the same conditions as in Example 3, except that in Example 3, 4.01 g (30 mol) of 5,6-dimethyl-1,4-dioxane-2-ol obtained in Synthetic Example 9 was used in place of 3.64 g (30 mol) of 1,4-oxathiane-2-ol.

Distilled water 13 g was added to the reaction mixture obtained, and it was separated into an organic layer and an aqueous layer. The organic layer was concentrated, and the residue obtained was refined by silica gel chromatography to obtain 5.47 g (26.1 mol) of 5,6-dimethyl-1,4-dioxane-2-yl=chloroacetate (yield: 87.0%).

Example 18

Production of 2-(5,6-dimethyl-1,4-dioxane-2-yloxy)-2-oxoethyl=methacrylate

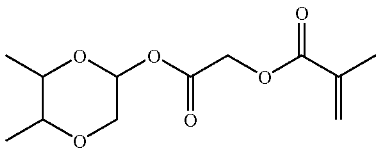 [SMILES: C=C(C)C(=O)OCC(=O)OC1COC(C)C(C)O1]

The reaction was carried out in the same charged amounts on the same conditions as in Example 4, except that in Example 4, 4.28 g (20.4 mol) of 5,6-dimethyl-1,4-dioxane-2-yl=chloroacetate obtained in Example 17 was used in place of 4.80 g (20.4 mol) of 1,4-oxathiane-2-yl=chloroacetate.

Distilled water 20 g was added to the reaction mixture obtained and stirred, and then it was separated into an organic layer and an aqueous layer, followed by washing the organic layer twice with 20 g of distilled water. The organic layer was concentrated, and the residue obtained was refined by silica gel chromatography to obtain 4.93 g (18.8 mol) of 2-(5,6-dimethyl-1,4-dioxane-2-yloxy)-2-oxoethyl=methacrylate (yield: 92.2%).

Example 19

Production of Polymer (a)

A round-bottom flask having a content volume of 200 mL equipped with a thermometer, a stirring device and a reflux condenser was charged with 13.17 g (50.2 mol) of 2-(1,4-dithiane-2-yloxy)-2-oxoethyl=methacrylate obtained in Example 2, 11.82 g (50.0 mol) of 3-hydroxy-1-adamantyl=methacrylate and 105.5 g of 1,4-dioxane, and it was subjected to bubbling of nitrogen for 10 minutes. The flask was charged with 1.24 g (7.55 mol) of 2,2'-azobisisobutyronitrile under nitrogen atmosphere to carry out polymerization reaction at 80 to 83° C. for 4 hours.

A reaction mixture obtained was dropwise added to a methanol mixed solution of about 20 times mass based on the reaction mixture at room temperature while stirring, and a precipitate produced was separated by filtering. The above precipitate was dissolved in 100.0 g of THF, and the solution prepared was dropwise added to methanol of the same mass as described above while stirring. A precipitate produced was separated by filtering and then washed with methanol of the same mass as described above, whereby a white precipitate was obtained. The above precipitate was dried at 50° C. for 10 hours under reduced pressure (26.7 Pa) to obtain 14.88 g of a polymer (a) comprising a repetitive unit shown below. The polymer (a) thus obtained had Mw of 10,900 and a dispersion degree of 1.75.

polymer (a)

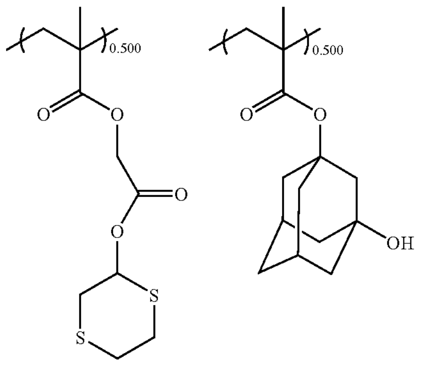

Example 20

Production of Polymer (b)

A round-bottom flask having a content volume of 200 mL equipped with a thermometer, a stirring device and a reflux condenser was charged with 12.36 g (50.2 mol) of 2-(1,4-oxathiane-2-yloxy)-2-oxoethyl=methacrylate obtained in Example 4, 11.82 g (50.0 mol) of 3-hydroxy-1-adamantyl=methacrylate and 103.4 g of 1,4-dioxane, and it was subjected to bubbling of nitrogen for 10 minutes. The flask was charged with 1.24 g (7.55 mol) of 2,2'-azobisisobutyronitrile under nitrogen atmosphere to carry out polymerization reaction at 80 to 82° C. for 4 hours.

A reaction mixture obtained was dropwise added to a methanol mixed solution of about 20 times mass based on the reaction mixture at room temperature while stirring, and a precipitate produced was separated by filtering. The above precipitate was dissolved in 100.0 g of THF, and the solution prepared was dropwise added to methanol of the same mass as described above while stirring. A precipitate produced was separated by filtering and then washed with methanol of the same mass as described above, whereby a white precipitate was obtained. The above precipitate was dried at 50° C. for 10 hours under reduced pressure (26.7 Pa) to obtain 14.35 g of a polymer (b) comprising a repetitive unit shown below. The polymer (b) thus obtained had Mw of 11,300 and a dispersion degree of 1.82.

polymer (b)

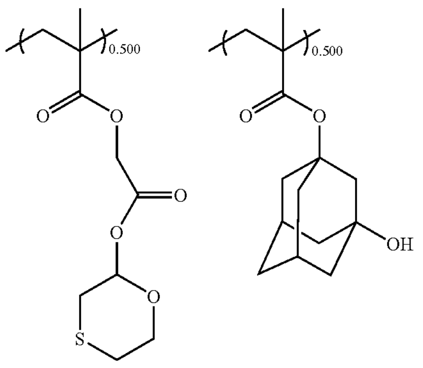

Example 21

Production of Polymer (c)

A round-bottom flask having a content volume of 100 mL equipped with a thermometer, a stirring device and a reflux condenser was charged with 4.91 g (18.7 mol) of 2-(1,4-dithiane-2-yloxy)-2-oxoethyl=methacrylate obtained in Example 2, 2.96 g (12.5 mol) of 3-hydroxy-1-adamantyl=methacrylate, 3.18 g (18.7 mol) of α-methacryloyloxy-γ-butyrolactone and 60.0 g of methyl ethyl ketone, and it was subjected to bubbling of nitrogen for 10 minutes. The flask was charged with 0.66 g (4.0 mol) of 2,2'-azobisisobutyronitrile under nitrogen atmosphere to carry out polymerization reaction at 80° C. for 4 hours.

A reaction mixture obtained was dropwise added to methanol of about 20 times mass at room temperature while stirring, whereby a white precipitate was obtained. The above precipitate was separated by filtering and dried at 50° C. for 10 hours under reduced pressure (26.7 Pa) to obtain 6.63 g of a polymer (c) comprising a repetitive unit shown below. The polymer (c) thus obtained had Mw of 8,100 and a dispersion degree of 1.80.

polymer (c)

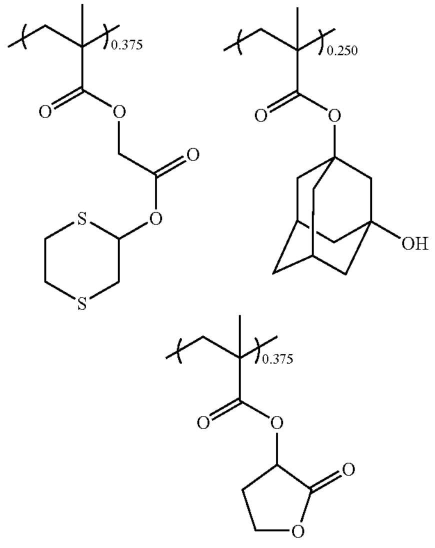

Example 22

Production of Polymer (d)

A round-bottom flask having a content volume of 100 mL equipped with a thermometer, a stirring device and a reflux condenser was charged with 4.61 g (18.7 mol) of 2-(1,4-oxothiane-2-yloxy)-2-oxoethyl=methacrylate obtained in Example 4, 2.96 g (12.5 mol) of 3-hydroxy-1-adamantyl=methacrylate, 3.18 g (18.7 mol) of α-methacryloyloxy-γ-butyrolactone and 61.0 g of methyl ethyl ketone, and it was subjected to bubbling of nitrogen for 10 minutes. The flask was charged with 0.66 g (4.0 mol) of 2,2'-azobisisobutyronitrile under nitrogen atmosphere to carry out polymerization reaction at 80° C. for 4 hours.

A reaction mixture obtained was dropwise added to methanol of about 20 times mass at room temperature while stirring, whereby a white precipitate was obtained. The above precipitate was separated by filtering and dried at 50° C. for 10 hours under reduced pressure (26.7 Pa) to obtain 6.45 g of a polymer (d) comprising a repetitive unit shown below. The polymer (d) thus obtained had Mw of 8,500 and a dispersion degree of 1.75.

polymer (d)

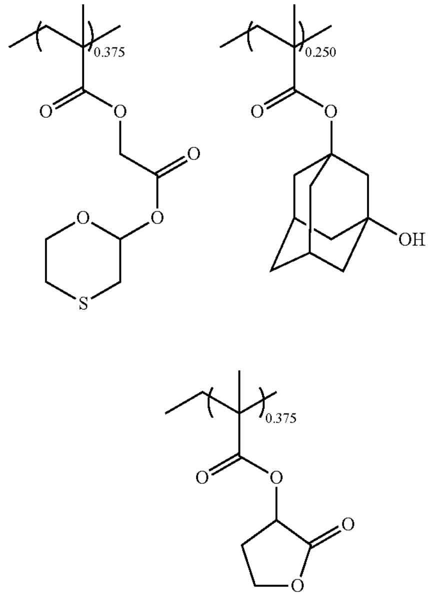

Example 23

Production of Polymer (e)

A round-bottom flask having a content volume of 100 mL equipped with a thermometer, a stirring device and a reflux condenser was charged with 2.34 g (10.0 mol) of 2-(1,4-dioxane-2-yloxy)-2-oxoethyl=methacrylate obtained in Example 6, 2.36 g (10.0 mol) of 1-hydroxy-3-methacryloyloxyadamantane and 20.0 g of 1,4-dioxane, and it was subjected to bubbling of nitrogen for 10 minutes. The flask was charged with 0.25 g (1.51 mol) of 2,2'-azobisisobutyronitrile under nitrogen atmosphere to carry out polymerization reaction at 80 to 82° C. for 4 hours.

A reaction mixture obtained was dropwise added to methanol of about 20 times mass per the reaction mixture at room temperature while stirring, and a precipitate produced was separated by filtering. The above precipitate was dissolved in 20.0 g of THF, and the solution prepared was dropwise added to methanol of the same mass as described above while stirring. A precipitate produced was separated by filtering and then washed with methanol of the same mass as described above, whereby a white precipitate was obtained. The above precipitate was dried at 50° C. for 10 hours under reduced pressure (26.7 Pa) to obtain 2.76 g of a polymer (e) comprising a repetitive unit shown below. The polymer (e) thus obtained had Mw of 13,400 and a dispersion degree of 1.69.

polymer (e)

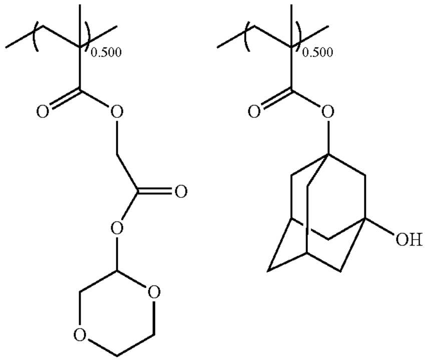

Example 24

Production of Polymer (f)

A round-bottom flask having a content volume of 100 mL equipped with a thermometer, a stirring device and a reflux condenser was charged with 4.38 g (18.7 mol) of 2-(1,4-dioxane-2-yloxy)-2-oxoethyl=methacrylate obtained in Example 6, 2.96 g (12.5 mol) of 1-hydroxy-3-methacryloyloxyadamantane, 3.18 g (18.7 mol) of α-methacryloyloxy-γ-butyrolactone and 61.0 g of methyl ethyl ketone, and it was subjected to bubbling of nitrogen for 10 minutes. The flask was charged with 0.66 g (4.0 mol) of 2,2'-azobisisobutyronitrile under nitrogen atmosphere to carry out polymerization reaction at 80° C. for 4 hours.

A reaction mixture obtained was dropwise added to methanol of about 20 times mass at room temperature while stirring, whereby a white precipitate was obtained. The above precipitate was separated by filtering and dried at 50° C. for 10 hours under reduced pressure (26.7 Pa) to obtain 6.19 g of a polymer (f) comprising a repetitive unit shown below. The polymer (f) thus obtained had Mw of 10,800 and a dispersion degree of 1.75.

polymer (f)

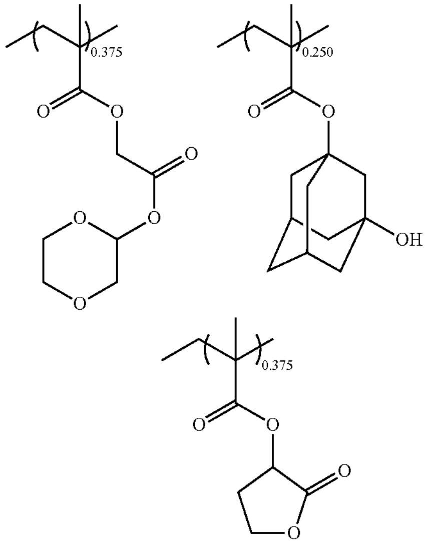

Example 25

Production of Polymer (g)

The reaction was carried out in the same charged amounts on the same conditions as in Example 23, except that in Example 23, 2.81 g (10.0 mol) of 2-(1,4-dithiepane-2-yloxy)-2-oxoethyl=methacrylate obtained in Example 8 was used in place of 2.34 g (10.0 mol) of 2-(1,4-dioxane-2-yloxy)-2-oxoethyl=methacrylate.

A reaction mixture obtained was dropwise added to methanol of about 20 times mass based on the reaction mixture at room temperature while stirring, and a precipitate produced was separated by filtering. The above precipitate was dissolved in 20.0 g of THF, and the solution prepared was dropwise added to methanol of the same mass as described above while stirring. A precipitate produced was separated by filtering and then washed with methanol of the same mass as described above, whereby a white precipitate was obtained. The above precipitate was dried at 50° C. for 10 hours under reduced pressure (26.7 Pa) to obtain 3.21 g of a polymer (g) comprising a repetitive unit shown below. The polymer (g) thus obtained had Mw of 12,800 and a dispersion degree of 1.72.

polymer (g)

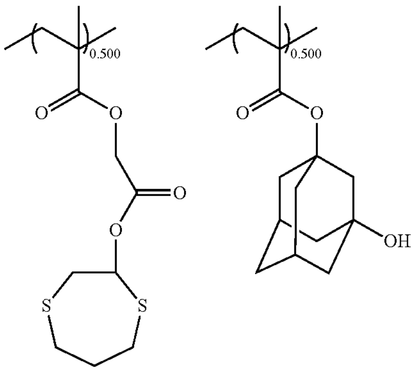

Example 26

Production of Polymer (h)

The reaction was carried out in the same charged amounts on the same conditions as in Example 23, except that in Example 23, 2.63 g (10.0 mol) of 2-(1,4-oxathiepane-2-yloxy)-2-oxoethyl=methacrylate obtained in Example 10 was used in place of 2.34 g (10.0 mol) of 2-(1,4-dioxane-2-yloxy)-2-oxoethyl=methacrylate.

A reaction mixture obtained was dropwise added to methanol of about 20 times mass based on the reaction mixture at room temperature while stirring, and a precipitate produced was separated by filtering. The above precipitate was dissolved in 20.0 g of THF, and the solution prepared was dropwise added to methanol of the same mass as described above while stirring. A precipitate produced was separated by filtering and then washed with methanol of the same mass as described above, whereby a white precipitate was obtained. The above precipitate was dried at 50° C. for 10 hours under reduced pressure (26.7 Pa) to obtain 2.88 g of a polymer (h) comprising a repetitive unit shown below. The polymer (h) thus obtained had Mw of 10,800 and a dispersion degree of 1.74.

polymer (h)

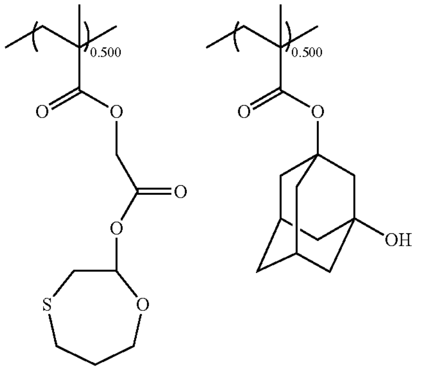

Example 27

Production of Polymer (i)

The reaction was carried out in the same charged amounts on the same conditions as in Example 23, except that in Example 23, 2.49 g (10.0 mol) of 2-(1,4-dioxepane-2-yloxy)-2-oxoethyl=methacrylate obtained in Example 12 was used in place of 2.34 g (10.0 mol) of 2-(1,4-dioxane-2-yloxy)-2-oxoethyl=methacrylate.

A reaction mixture obtained was dropwise added to methanol of about 20 times mass based on the reaction mixture at room temperature while stirring, and a precipitate produced was separated by filtering. The above precipitate was dissolved in 20.0 g of THF, and the solution prepared was dropwise added to methanol of the same mass as described above while stirring. A precipitate produced was separated by filtering and then washed with methanol of the same mass as described above, whereby a white precipitate was obtained. The above precipitate was dried at 50° C. for 10 hours under reduced pressure (26.7 Pa) to obtain 2.76 g of a polymer (i) comprising a repetitive unit shown below. The polymer (i) thus obtained had Mw of 11,500 and a dispersion degree of 1.63.

polymer (i)

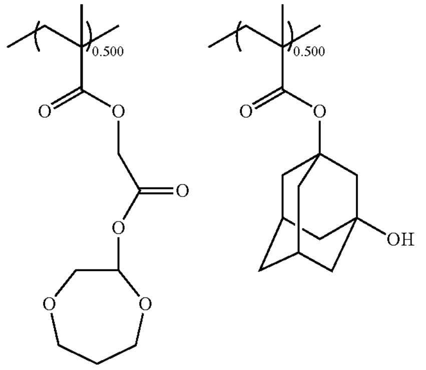

Example 28

Production of Polymer (j)

The reaction was carried out in the same charged amounts on the same conditions as in Example 23, except that in Example 23, 2.93 g (10.0 mol) of 2-(5,6-dimethyl-1,4-dithiane-2-yloxy)-2-oxoethyl=methacrylate obtained in Example 14 was used in place of 2.34 g (10.0 mol) of 2-(1,4-dioxane-2-yloxy)-2-oxoethyl=methacrylate.

A reaction mixture obtained was dropwise added to methanol of about 20 times mass based on the reaction mixture at room temperature while stirring, and a precipitate produced was separated by filtering. The above precipitate was dissolved in 20.0 g of THF, and the solution prepared was dropwise added to methanol of the same mass as described above while stirring. A precipitate produced was separated by filtering and then washed with methanol of the same mass as described above, whereby a white precipitate was obtained. The above precipitate was dried at 50° C. for 10 hours under reduced pressure (26.7 Pa) to obtain 3.39 g of a polymer (j) comprising a repetitive unit shown below. The polymer (j) thus obtained had Mw of 9,900 and a dispersion degree of 1.78.

polymer (j)

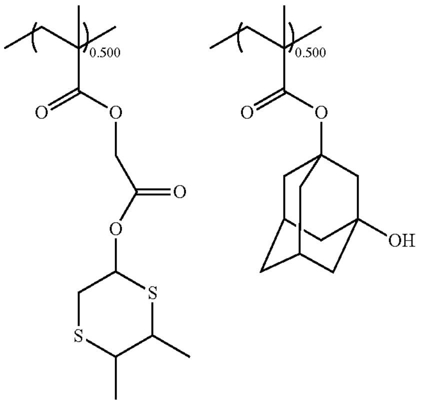

Example 29

Production of Polymer (k)

The reaction was carried out in the same charged amounts on the same conditions as in Example 23, except that in Example 23, 2.63 g (10.0 mol) of 2-(6-methyl-1,4-oxathiane-2-yloxy)-2-oxoethyl=methacrylate obtained in Example 16 was used in place of 2.34 g (10.0 mol) of 2-(1,4-dioxane-2-yloxy)-2-oxoethyl=methacrylate.

A reaction mixture obtained was dropwise added to methanol of about 20 times mass based on the reaction mixture at room temperature while stirring, and a precipitate produced was separated by filtering. The above precipitate was dissolved in 20.0 g of THF, and the solution prepared was dropwise added to methanol of the same mass as described above while stirring. A precipitate produced was separated by filtering and then washed with methanol of the same mass as described above, whereby a white precipitate was obtained. The above precipitate was dried at 50° C. for 10 hours under reduced pressure (26.7 Pa) to obtain 2.99 g of a polymer (k) comprising a repetitive unit shown below. The polymer (k) thus obtained had Mw of 12,100 and a dispersion degree of 1.60.

polymer (k)

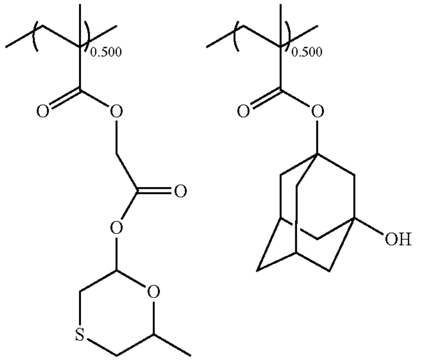

Example 30

Production of Polymer (l)

The reaction was carried out in the same charged amounts on the same conditions as in Example 23, except that in Example 23, 2.62 g (10.0 mol) of 2-(5,6-dimethyl-1,4-dioxane-2-yloxy)-2-oxoethyl=methacrylate obtained in Example 18 was used in place of 2.34 g (10.0 mol) of 2-(1,4-dioxane-2-yloxy)-2-oxoethyl=methacrylate.

A reaction mixture obtained was dropwise added to methanol of about 20 times mass based on the reaction mixture at room temperature while stirring, and a precipitate produced was separated by filtering. The above precipitate was dissolved in 20.0 g of THF, and the solution prepared was dropwise added to methanol of the same mass as described above while stirring. A precipitate produced was separated by filtering and then washed with methanol of the same mass as described above, whereby a white precipitate was obtained. The above precipitate was dried at 50° C. for 10 hours under reduced pressure (26.7 Pa) to obtain 2.89 g of a polymer (l) comprising a repetitive unit shown below. The polymer (l) thus obtained had Mw of 11,900 and a dispersion degree of 1.66, polymer (l)

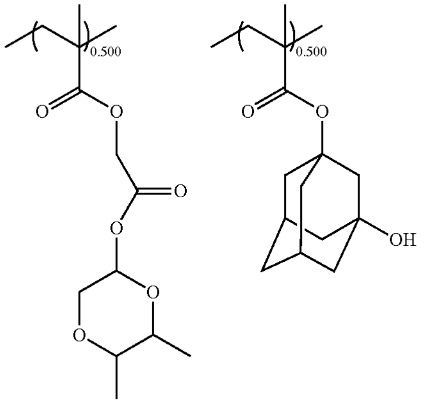

Comparative Example 1

Production of Polymer (A)

A round-bottom flask having a content volume of 200 mL equipped with a thermometer, a stirring device and a reflux condenser was charged with 10.0 g (42.3 mol) of 2-methyl-2-adamantyl=methacrylate, 10.0 g (42.7 mol) of 3-hydroxy-1-adamantyl=methacrylate and 80.0 g of propylene glycol monomethyl ether, and it was subjected to bubbling of nitrogen for 10 minutes. The flask was charged with 1.40 g (8.53 mol) of 2,2'-azobisisobutyronitrile under nitrogen atmosphere to carry out polymerization reaction at 81 to 87° C. for 2 hours.

A reaction mixture obtained was dropwise added to methanol of about 20 times mass at room temperature while stirring to thereby obtain a white precipitate. The above precipitate was dissolved in 100.0 g of THF, and the solution prepared was dropwise added to methanol of the same mass as described above while stirring. A precipitate produced was separated by filtering and then washed with methanol of the same mass as described above, whereby a white precipitate was obtained. The above precipitate was dried at 50° C. for 10 hours under reduced pressure (26.7 Pa) to obtain 13.2 g of a polymer (A) comprising a repetitive unit shown below. The polymer (A) thus obtained had Mw of 16,100 and a dispersion degree of 1.68.

polymer (A)

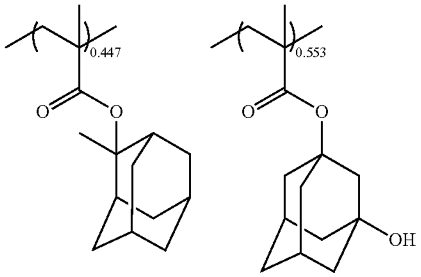

Comparative Example 2

Production of Polymer (B)

A round-bottom flask having a content volume of 200 mL equipped with a thermometer, a stirring device and a reflux condenser was charged with 7.39 g (42.7 mol) of tetrahydropyran-2-yl=methacrylate, 10.0 g (42.7 mol) of 3-hydroxy-1-adamantyl=methacrylate and 80.0 g of propylene glycol monomethyl ether, and it was subjected to bubbling of nitrogen for 10 minutes. The flask was charged with 1.40 g (8.53 mol) of 2,2'-azobisisobutyronitrile under nitrogen atmosphere to carry out polymerization reaction at 81 to 87° C. for 2 hours.

A reaction mixture obtained was dropwise added to methanol of about 20 times mass at room temperature while stirring to thereby obtain a white precipitate. The above precipitate was dissolved in 100.0 g of THF, and the solution prepared was dropwise added to methanol of the same mass as described above while stirring. A precipitate produced was separated by filtering and then washed with methanol of the same mass as described above, whereby a white precipitate was obtained. The above precipitate was dried at 5° C. for 10 hours under reduced pressure (26.7 Pa) to obtain 9.96 g of a polymer (B) comprising a repetitive unit shown below. The polymer (B) thus obtained had Mw of 13,200 and a dispersion degree of 1.71.

polymer (B)

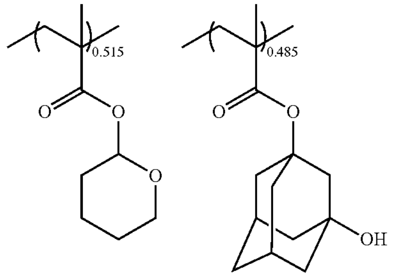

Comparative Example 3

Production of Polymer (C)

A round-bottom flask having a content volume of 200 mL equipped with a thermometer, a stirring device and a reflux condenser was charged with 12.06 g (50.2 mol) of 2-(1-methyl-1-cyclohexyl)-2-oxoethyl=methacrylate, 11.82 g (50.0 mol) of 3-hydroxy-1-adamantyl=methacrylate, 101.4 g of 1,4-dioxane and 1.24 g (7.55 mol) of 2,2'-azobisisobutyronitrile under nitrogen atmosphere to carry out polymerization reaction at 80 to 82° C. for 5 hours.

A reaction mixture obtained was dropwise added to a water-methanol mixed solution (weight ratio water:methanol=1:3) of about 20 times mass based on the reaction mixture at room temperature while stirring, and a precipitate produced was separated by filtering. The above precipitate was dissolved in 140.0 g of THF, and the solution prepared was dropwise added to the water-methanol mixed solution (weight ratio water:methanol=1:3) of the same mass as described above while stirring. A precipitate produced was separated by filtering and then washed with the water-methanol mixed solution (weight ratio water:methanol=1:3) of the same mass as described above, whereby a white precipitate was obtained. The above precipitate was dried at 50° C. for 10 hours under reduced pressure (26.7 Pa) to obtain 14.03 g of a polymer (C) comprising a repetitive unit shown below. The polymer (C) thus obtained had Mw of 11,600 and a dispersion degree of 1.73.

polymer (C)

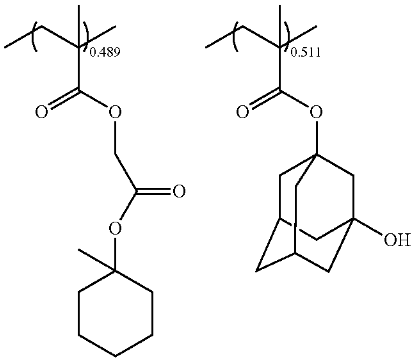

Comparative Example 4

Production of Polymer (D)

A round-bottom flask having a content volume of 100 mL equipped with a thermometer, a stirring device and a reflux condenser was charged with 4.39 g (18.7 mol) of 2-methyl-2-adamantyl=methacrylate, 2.96 g (12.5 mol) of 3-hydroxy-1-adamantyl=methacrylate, 3.18 g (18.7 mol) of α-methacryloyloxy-γ-butyrolactone and 60.5 g of methyl ethyl ketone, and it was subjected to bubbling of nitrogen for 10 minutes. The flask was charged with 0.66 g (4.0 mol) of 2,2'-azobisisobutyronitrile under nitrogen atmosphere to carry out polymerization reaction at 80° C. for 4 hours.

A reaction mixture obtained was dropwise added to methanol of about 20 times mass at room temperature while stirring to thereby obtain a white precipitate. The above precipitate was separated by filtering and dried at 50° C. for 10 hours under reduced pressure (26.7 Pa) to obtain 6.06 g of a polymer (D) comprising a repetitive unit shown below. The polymer (D) thus obtained had Mw of 10,000 and a dispersion degree of 1.50.

polymer (D)

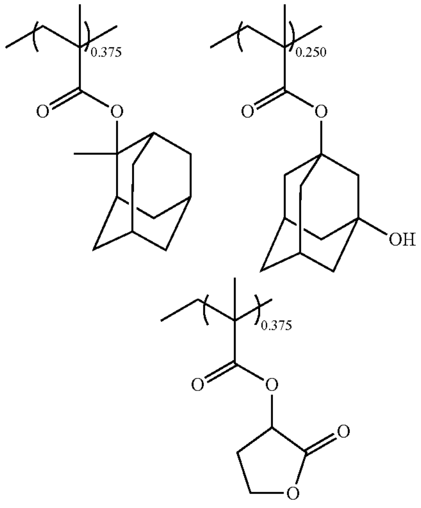

Comparative Example 5

Production of Polymer (E)

A round-bottom flask having a content volume of 100 mL equipped with a thermometer, a stirring device and a reflux condenser was charged with 3.18 g (18.7 mol) of tetrahydropyran-2-yl=methacrylate, 2.96 g (12.5 mol) of 3-hydroxy-1-adamantyl=methacrylate, 3.18 g (18.7 mol) of α-methacryloyloxy-γ-butyrolactone and 58.0 g of methyl ethyl ketone, and it was subjected to bubbling of nitrogen for 10 minutes. The flask was charged with 0.66 g (4.0 mol) of 2,2'-azobisisobutyronitrile under nitrogen atmosphere to carry out polymerization reaction at 80° C. for 4 hours.

A reaction mixture obtained was dropwise added to methanol of about 20 times mass at room temperature while stirring to thereby obtain a white precipitate. The above precipitate was separated by filtering and dried at 50° C. for 10 hours under reduced pressure (26.7 Pa) to obtain 5.82 g of a polymer (E) comprising a repetitive unit shown below. The polymer (E) thus obtained had Mw of 6,500 and a dispersion degree of 1.60.

polymer (E)

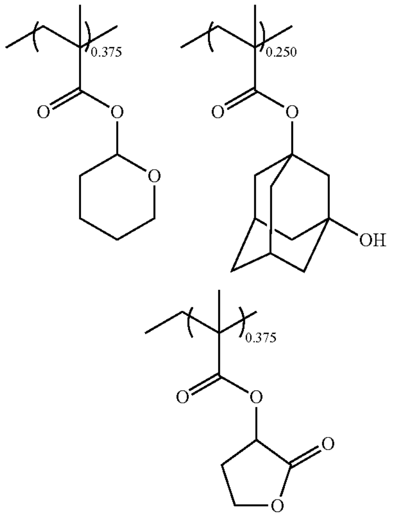

Comparative Example 6

Production of Polymer (F)

A round-bottom flask having a content volume of 100 mL equipped with a thermometer, a stirring device and a reflux condenser was charged with 4.49 g (18.7 mol) of 2-(1-methyl-1-cyclohexyl)-2-oxoethyl=methacrylate, 2.96 g (12.5 mol) of 3-hydroxy-1-adamantyl=methacrylate, 3.18 g (18.7 mol) of α-methacryloyloxy-γ-butyrolactone and 60.0 g of methyl ethyl ketone, and it was subjected to bubbling of nitrogen for 10 minutes. The flask was charged with 0.66 g (4.0 mol) of 2,2'-azobisisobutyronitrile under nitrogen atmosphere to carry out polymerization reaction at 80° C. for 4 hours.

A reaction mixture obtained was dropwise added to methanol of about 20 times mass at room temperature while stirring to thereby obtain a white precipitate. The above precipitate was separated by filtering and dried at 50° C. for 10 hours under reduced pressure (26.7 Pa) to obtain 6.16 g of a polymer (F) comprising a repetitive unit shown below. The polymer (F) thus obtained had Mw of 7,100 and a dispersion degree of 1.75.

polymer (F)

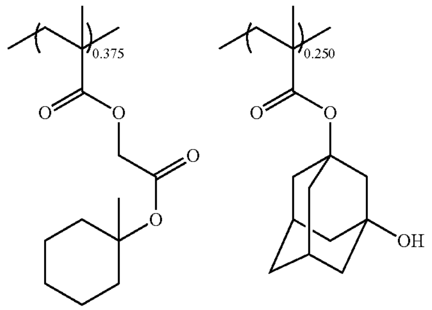

-continued

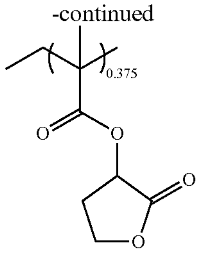

Comparative Example 7

Production of Polymer (G)

The polymerization reaction was carried out in the same charged amounts on the same conditions as in Comparative Example 1, except that in Comparative Example 1, 8.98 g (42.7 mol) of 1,3-dithiane-5-yl=methacrylate was used in place of 10.0 g (42.3 mol) of 2-methyl-2-adamantyl=methacrylate.

A reaction mixture obtained was dropwise added to methanol of about 20 times mass based on the reaction mixture at room temperature while stirring, and a precipitate produced was separated by filtering. The above precipitate was dissolved in 100.0 g of THF, and the solution prepared was dropwise added to methanol of the same mass as described above while stirring. A precipitate produced was separated by filtering and then washed with methanol of the same mass as described above, whereby a white precipitate was obtained. The above precipitate was dried at 50° C. for 10 hours under reduced pressure (26.7 Pa) to obtain 10.22 g of a polymer (G) comprising a repetitive unit shown below. The polymer (G) thus obtained had Mw of 15,200 and a dispersion degree of 1.69.

polymer (G)

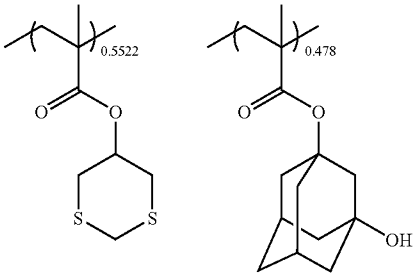

Comparative Example 8

Production of Polymer (H)

The polymerization reaction was carried out in the same charged amounts on the same conditions as in Comparative Example 1, except that in Comparative Example 1, 7.59 g (42.7 mol) of 5-methacryloyloxy-1,3-dioxane was used in place of 10.0 g (42.3 mol) of 2-methyl-2-adamantyl=methacrylate.

A reaction mixture obtained was dropwise added to diisopropyl ether of about 20 times mass based on the reaction mixture at room temperature while stirring, and a precipitate produced was separated by filtering. The above precipitate was dissolved in 100.0 g of 1,4-dioxane, and the solution prepared was dropwise added to a diisopropyl ether/methanol mixed solution (weight ratio diisopropyl ether:methanol=4:1) of the same mass as described above while stirring. A precipitate produced was separated by filtering and then washed with the diisopropyl ether/methanol mixed solution (weight ratio diisopropyl ether:methanol=4:1) of the same mass as described above, whereby a white precipitate was obtained. The above precipitate was dried at 50° C. for 10 hours under reduced pressure (26.7 Pa) to obtain 9.01 g of a polymer (H) comprising a repetitive unit shown below. The polymer (H) thus obtained had Mw of 16,700 and a dispersion degree of 1.71.

polymer (H)

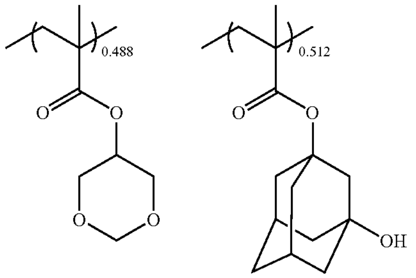

Examples 31 to 42 and Comparative Examples 1 to 8

Evaluation of Dissolution Characteristics in Developer by QCM Method

Mixed were 100 parts by mass of the polymers obtained in Examples 19 to 30 or Comparative Synthetic Examples 1 to 8, 3parts by mass of TPS-109 (trade name, component: triphenylsulfonium nonafluoro-n-butanesulfonate, manufactured by Midori Kagaku Co., Ltd.) as a photoacid generator and a mixed solvent of propylene glycol monomethyl ether acetate/ethyl lactate=1/1 (volume ratio) to prepare photoresist compositions in which a concentration of the polymer was 12% by mass.

The respective photoresist compositions thus obtained were filtrated through a filter (made of a tetrafluoroethylene resin (PTFE), pore diameter: 0.2 μm), and then they were coated respectively by a spin coating method on a quartz substrate of a 1 inch size in which a gold electrode was vacuum-deposited on a surface to form a photosensitive layer having a thickness of 300 nm. The quartz substrate having the photosensitive layer formed thereon was pre-baked at 110° C. for 90 seconds on a hot plate and then exposed at an exposure dose of 100 mJ/$cm^2$ with an ArF excimer laser (wavelength: 193 nm), and subsequently it was subjected to post-exposure baking at 110° C. for 90 seconds.

The quartz substrate described above was set in a quartz oscillator microbalance equipment "RQCM" (trade name; manufactured by Maxtek Corp.) and subjected to developing treatment by a tetramethylammonium hydroxide aqueous solution of 2.38% by mass for 120 seconds. A change in an oscillation frequency of the quartz substrate during the developing treatment was monitored with the passage of time, and then a change in the oscillation frequency was reduced to a change in the film thickness to calculate the maximum swelling amount from a change in an increase of the film thickness and calculate the dissolution rate from a change in a decrease of the film thickness. The results thereof are shown in Table 1.

TABLE 1 evaluation of dissolution characteristics in developer by QCM method

| | Polymer in photoresist composition | Dissolution rate in developing (nm/second) | Maximum swelling amount (nm) |
|---|---|---|---|
| Example 31 | (a) | 1290 | 8 |
| Example 32 | (b) | 1380 | 7 |
| Example 33 | (c) | 1270 | 8 |
| Example 34 | (d) | 1350 | 7 |
| Example 35 | (e) | 1420 | 9 |
| Example 36 | (f) | 1390 | 8 |
| Example 37 | (g) | 1280 | 9 |
| Example 38 | (h) | 1320 | 9 |
| Example 39 | (i) | 1350 | 8 |
| Example 40 | (j) | 1250 | 9 |
| Example 41 | (k) | 1320 | 7 |
| Example 42 | (l) | 1300 | 8 |
| Comparative Example 1 | (A) | 950 | 100 |
| Comparative Example 2 | (B) | 1200 | 10 |
| Comparative Example 3 | (C) | 550 | 18 |
| Comparative Example 4 | (D) | 600 | 40 |
| Comparative Example 5 | (E) | 1100 | 10 |
| Comparative Example 6 | (F) | 780 | 15 |
| Comparative Example 7 | (G) | Not dissolved | — |
| Comparative Example 8 | (H) | 90 | 150 |

Examples 43 to 54 and Comparative Examples 9 to 16

Evaluation of Exposure by Two-Beam Interference Method

Mixed were 100 parts by mass of the polymers obtained in Examples 19 to 30 or Comparative Synthetic Examples 1 to 8, 3 parts by mass of TPS-109 (trade name, component: triphenylsulfonium nonafluoro-n-butanesulfonate, manufactured by Midori Kagaku Co., Ltd.) as a photoacid generator and a mixed solvent of propylene glycol monomethyl ether acetate/ethyl lactate=1/1 (volume ratio) to prepare 12 kinds of photoresist compositions in which a concentration of the polymer was 12% by mass.

The respective photoresist compositions thus obtained were filtrated through a filter (made of a tetrafluoroethylene resin (PTFE), pore diameter: 0.2 μm). A propylene glycol monomethyl ether acetate solution of a cresol novolac resin (PS-6937, manufactured by Gunei Chemical Industry Co., Ltd.) having a concentration of 6% by mass was coated on a silicon wafer having a diameter of 10 cm by a spin coating method and baked at 200° C. for 90 seconds on a hot plate to thereby form a antireflective coat (undercoat film), and the above filtrates were coated respectively on the above silicon wafer by a spin coating method and pre-baked at 130° C. for 90 seconds on a hot plate to thereby form a resist film having a film thickness of about 300 nm.

The above resist film was exposed with an ArF excimer laser having a wavelength of 193 nm by a two-beam interference method. Subsequently, it was subjected to post-exposure baking at 130° C. for 90 seconds and then to developing treatment for 60 seconds by a 2.38 mass % tetramethylammonium hydroxide aqueous solution to thereby form a line and space pattern of 1:1. A piece obtained by cutting the wafer subjected to the development was observed under a scanning electron microscope (SEM) to observe a form of the pattern in an exposure dose in which the line and space having a line width of 100 nm was subjected to resolution by 1:1 and measure a change in the line width (hereinafter referred to as LWR). The line width was detected in plural positions in a measuring monitor, and dispersion (3σ) in variation of the detected positions was set to an index for LWR. The results thereof are shown in Table 2.

TABLE 2 evaluation of exposure by two-beam interference method

| | Polymer in photoresist composition | LWR (nm) | Pattern form |
|---|---|---|---|
| Example 43 | (a) | 7.8 | Good |
| Example 44 | (b) | 7.0 | Good |
| Example 45 | (c) | 7.1 | Good |
| Example 46 | (d) | 6.9 | Good |
| Example 47 | (e) | 7.3 | Good |
| Example 48 | (f) | 6.9 | Good |
| Example 49 | (g) | 7.9 | Good |
| Example 50 | (h) | 7.5 | Good |
| Example 51 | (i) | 7.3 | Good |
| Example 52 | (j) | 7.8 | Good |
| Example 53 | (k) | 7.0 | Good |
| Example 54 | (l) | 7.1 | Good |
| Comparative Example 9 | (A) | 13.4 | Good |
| Comparative Example 10 | (B) | 8.1 | Good |
| Comparative Example 11 | (C) | 9.7 | Good |
| Comparative Example 12 | (D) | 12.3 | Good |
| Comparative Example 13 | (E) | 8.5 | Good |
| Comparative Example 14 | (F) | 8.9 | Good |
| Comparative Example 15 | (G) | Unable to form pattern | — |
| Comparative Example 16 | (H) | Unable to form pattern | — |

It can be found from the results shown in Table 1 and Table 2 that in the case of the polymers (a) to (l) containing the (meth)acrylic ester derivative (1) of the present invention in a repetitive unit, a dissolution rate in an alkali developer used in a developing step when a photoresist is produced is very high as compared with the case of the polymers (A) to (H) containing no (meth)acrylic ester derivative (1) in a repetitive unit and that they have a very small maximum swelling amount in developing and are improved in LWR. Accordingly, they are useful as a chemically amplified resist for producing semiconductor devices.

Industrial Applicability

The polymer (6) obtained by polymerizing a raw material containing the (meth)acrylic ester derivative (1) obtained in the present invention is useful as a raw material for photoresist compositions. Further, the haloester derivative (4) obtained in the present invention is useful as a synthetic intermediate for the (meth)acrylic ester derivative (1).

The invention claimed is:

1. A process for producing a (meth)acrylic ester derivative of Formula (1):

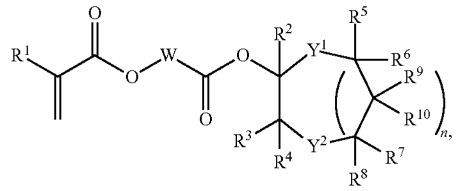

(1)

the process comprising:

reacting alcohol of Formula (2):

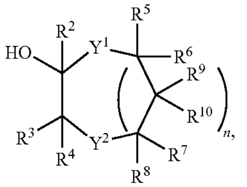

(2)

wherein a combination of $R^2$, $R^3$, and $R^4$ is at least one selected from the group consisting of:

1) $R^2$, $R^3$ and $R^4$ each independently, hydrogen atom, a linear alkyl group having 1 to 6 carbon atoms, a branched alkyl group having 3 to 6 carbon atoms, or a cyclic alkyl group having 3 to 6 carbon atoms;

2) $R^2$ and $R^3$ are combined as an alkylene group having 3 to 6 carbon atoms, and $R^4$ is a hydrogen atom, a linear alkyl group having 1 to 6 carbon atoms, a branched alkyl group having 3 to 6 carbon atoms, or a cyclic alkyl group having 3 to 6 carbon atoms;

3) $R^2$ is a hydrogen atom, a linear alkyl group having 1 to 6 carbon atoms, a branched alkyl group having 3 to 6 carbon atoms, or a cyclic alkyl group having 3 to 6 carbon atoms, and $R^3$ and $R^4$ are combined as an alkylene group having 3 to 6 carbon atoms;

$Y^1$ and $Y^2$ are each independently, an oxygen atom or a sulfur atom, with the proviso that both $Y^1$ and $Y^2$ cannot simultaneously be an oxygen atom, n is 0.1 or 2, such that 1) when n is 0, $R^5$ and $R^6$ are each independently, a hydrogen atom, a linear alkyl group having 1 to 6 carbon atoms, a branched alkyl group having 3 to 6 carbon atoms, or a cyclic alkyl group having 3 to 6 carbon atoms, $R^6$ and $R^7$ are each independently, a hydrogen atom, a linear alkyl group having 1 to 6 carbon atoms, a branched alkyl group having 3 to 6 carbon atoms, or a cyclic alkyl group having 3 to 6 carbon atoms, or $R^6$ and $R^7$ are combined as an alkylene group having 3 to 6 carbon atoms; or 2) when n is 1 or 2, $R^5$, $R^6$, $R^7$, $R^8$, $R^9$, and $R^{10}$ are each independently a hydrogen atom, a linear alkyl group having 1 to 6 carbon atoms, a branched alkyl group having 3 to 6 carbon atoms or a cyclic alkyl group having 3 to 6 carbon atoms, with halocarboxylic halide represented by Formula (3):

(3)

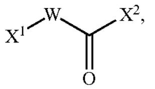

wherein W is a linear alkylene group having 1 to 10 carbon atoms, a branched alkylene group having 3 to 10 carbon atoms, or a cyclic alkylene group having 3 to 10 carbon atoms, and $X^1$ and $X^2$ are each independently a chlorine atom, a bromine atom, or an iodine atom, in the presence of a basic substance to thereby obtain a haloester derivative of Formula (4):

(4)

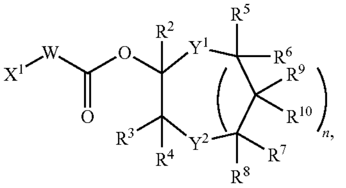

wherein n, $R^2$, $R^3$, $R^4$, $R^5$, $R^6$, $R^7$, $R^8$, $R^9$, $R^{10}$, W, $X^1$, $Y^1$, and $Y^2$, are as defined above; and reacting the haloester derivative of Formula (4) with a (meth)acrylic acid of Formula (5):

(5)

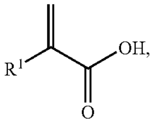

wherein $R^1$ is a hydrogen atom, methyl or trifluoromethyl, in the presence of a basic substance.

2. A process for producing a (meth)acrylic ester derivative of Formula (1):

(1)

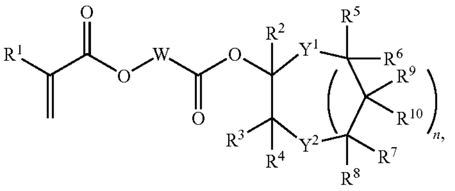

wherein $R^1$ is a hydrogen atom, methyl group or trifluoromethyl group, a combination of $R^2$, $R^3$, and $R^4$ is at least one selected from the group consisting of:

1) $R^2$, $R^3$ and $R^4$ are each, independently, a hydrogen atom, a linear alkyl group having 1 to 6 carbon atoms, a branched alkyl group having 3 to 6 carbon atoms, or a cyclic alkyl group having 3 to 6 carbon atoms;

2) $R^2$ and $R^3$ are combined as an alkylene group having 3 to 6 carbon atoms, and $R^4$ is a hydrogen atom, a linear alkyl group having 1 to 6 carbon atoms, a branched alkyl group having 3 to 6 carbon atoms, or a cyclic alkyl group having 3 to 6 carbon atoms;

3) $R^2$ is a hydrogen atom, a linear alkyl group having 1 to 6 carbon atoms, a branched alkyl group having 3 to 6 carbon atoms, or a cyclic alkyl group having 3 to 6 carbon atoms, and $R^3$ and $R^4$ are combined as an alkylene group having 3 to 6 carbon atoms, $Y^1$ and $Y^2$ are each independently, an oxygen atom or a sulfur atom, with the proviso that both $Y^1$ and $Y^2$ cannot simultaneously be an oxygen atom, W is a linear alkylene group having 1 to 10 carbon atoms, a branched alkylene group having 3 to 10 carbon atoms, or a cyclic alkylene group having 3 to 10 carbon atoms, n is 0.1 or 2, such that 1) when n is 0, $R^5$ and $R^6$ are each, independently, a hydrogen atom, a linear alkyl group having 1 to 6 carbon atoms, a branched alkyl group having 3 to 6 carbon atoms, or a cyclic alkyl group having 3 to 6 carbon atoms, $R^6$ and $R^7$ are each independently, a hydrogen atom, a linear alkyl group having 1 to 6 carbon atoms, a branched alkyl group having 3 to 6 carbon atoms, or a cyclic alkyl group having 3 to 6 carbon atoms, or $R^6$ and $R^7$ are combined as an alkylene group having 3 to 6 carbon atoms; or 2) when n is 1 or 2, $R^5$, $R^6$, $R^7$, $R^8$, $R^9$, and $R^{10}$ are each independently a hydrogen atom, a linear alkyl group having 1 to 6 carbon atoms, a branched alkyl group having 3 to 6 carbon atoms or a cyclic alkyl group having 3 to 6 carbon atoms, the process comprising reacting a haloester derivative of Formula (4):

(4)

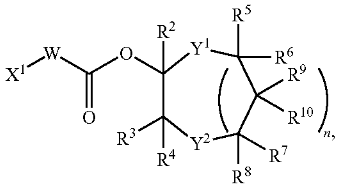

wherein n, $R^2$, $R^3$, $R^4$, $R^5$, $R^6$, $R^7$, $R^8$, $R^9$, $R^{10}$, W ,$Y^1$ and $Y^2$, are defined above, and $X^1$ is a chlorine atom, a bromine atom, or an iodine atom, with (meth)acrylic acid of Formula (5):

(5)

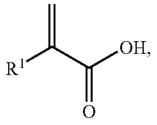

wherein $R^1$ is as defined above, in the presence of a basic substance.

3. A (meth)acrylic ester derivative of Formula (1):

(1)

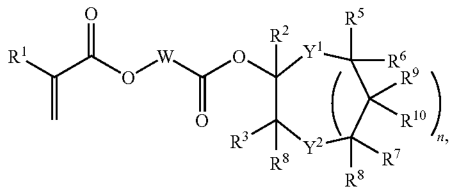

wherein $R^1$ is a hydrogen atom, methyl or trifluoromethyl group, a combination of $R^2$, $R^3$, and $R^4$ is at least one selected from the group consisting of:

1) $R^2$, $R^3$ and $R^4$ are each independently, hydrogen atom, a linear alkyl group having 1 to 6 carbon atoms, a branched alkyl group having 3 to 6 carbon atoms, or a cyclic alkyl group having 3 to 6 carbon atoms;

2) $R^2$ and $R^3$ are combined to represent an alkylene group having 3 to 6 carbon atoms, and $R^4$ is a hydrogen atom, a linear alkyl group having 1 to 6 carbon atoms, a branched alkyl group having 3 to 6 carbon atoms, or a cyclic alkyl group having 3 to 6 carbon atoms; and 3) $R^2$ is a hydrogen atom, a linear alkyl group having 1 to 6 carbon atoms, a branched alkyl group having 3 to 6 carbon atoms, or a cyclic alkyl group having 3 to 6 carbon atoms, and $R^3$ and $R^4$ are combined as an alkylene group having 3 to 6 carbon atoms, n is 0, 1 or 2, $Y^1$ and $Y^2$ are each independently, an oxygen atom or a sulfur atom, with the proviso that both $Y^1$ and $Y^2$ cannot simultaneously be an oxygen atom, and W is a linear alkylene group having 1 to 10 carbon atoms, a branched alkylene group having 3 to 10 carbon atoms, or a cyclic alkylene group having 3 to 10 carbon atoms, and wherein 1) when n is 0, $R^5$ and $R^6$ are each independently, a hydrogen atom, a linear alkyl group having 1 to 6 carbon atoms, a branched alkyl group having 3 to 6 carbon atoms, or a cyclic alkyl group having 3 to 6 carbon atoms, $R^7$ and $R^8$ are each independently, a hydrogen atom, a linear alkyl group having 1 to 6 carbon atoms, a branched alkyl group having 3 to 6 carbon atoms, or a cyclic alkyl group having 3 to 6 carbon atoms, or $R^6$ and $R^7$ are combined as an alkylene group having 3 to 6 carbon atoms;

or 2) when n is 1 or 2, $R^5$, $R^6$, $R^7$, $R^8$, $R^9$, and $R^{10}$ are each independently a hydrogen atom, a linear alkyl group having 1 to 6 carbon atoms, a branched alkyl group having 3 to 6 carbon atoms or a cyclic alkyl group having 3 to 6 carbon atoms.

4. The (meth)acrylic ester derivative according to claim 3, wherein:

W is methylene or ethane-1,1-diyl;

n is 0 or 1; and $R^2$, $R^3$, $R^4$, $R^5$, $R^6$, $R^7$, $R^8$, $R^9$, and $R^{10}$ are each, independently, a hydrogen atom or methyl.

5. A polymer obtained by polymerizing a raw material comprising the (meth)acrylic ester derivative according to claim 3.

6. A photoresist composition comprising the polymer according to claim 5.

7. A polymer obtained by polymerizing a raw material comprising the (meth)acrylic ester derivative according to claim 4.

8. A photoresist composition comprising the polymer according to claim 7.

* * * * *